US012631655B2

(12) United States Patent (10) Patent No.: US 12,631,655 B2
Peterson et al. (45) Date of Patent: May 19, 2026

(54) METHODS AND COMPOSITIONS FOR DIFFERENTIATING PROGRESSIVE CHRONIC KIDNEY DISEASE FROM STABLE CHRONIC KIDNEY DISEASE

(71) Applicant: IDEXX LABORATORIES, INC., Westbrook, ME (US)

(72) Inventors: Sarah Maier Peterson, Westbrook, ME (US); Yerramilli V.S.N. Murthy, Westbrook, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 530 days.

(21) Appl. No.: 18/160,000

(22) Filed: Jan. 26, 2023

(65) Prior Publication Data

US 2023/0243852 A1     Aug. 3, 2023

Related U.S. Application Data

(60) Provisional application No. 63/354,878, filed on Jun. 23, 2022, provisional application No. 63/267,181, filed on Jan. 26, 2022.

(51) Int. Cl.
*G01N 33/68* (2006.01)

(52) U.S. Cl.
CPC ... *G01N 33/6893* (2013.01); *G01N 2333/775* (2013.01); *G01N 2333/8139* (2013.01); *G01N 2800/347* (2013.01); *G01N 2800/56* (2013.01)

(58) Field of Classification Search
CPC ....... G01N 33/6893; G01N 2333/8139; G01N 2800/347; G01N 2800/56
See application file for complete search history.

(56) References Cited

U.S. PATENT DOCUMENTS

| | | | | | |
|---|---|---|---|---|---|
| 4,366,246 | A | 12/1982 | Riggs | | |
| 4,816,397 | A | 3/1989 | Boss et al. | | |
| 4,816,567 | A | 3/1989 | Cabilly et al. | | |
| 5,225,539 | A | 7/1993 | Winter | | |
| 5,530,101 | A | 6/1996 | Queen et al. | | |
| 5,565,332 | A | 10/1996 | Hoogenboom et al. | | |
| 5,585,089 | A | 12/1996 | Queen et al. | | |
| 5,726,010 | A | 3/1998 | Clark | | |
| 5,807,715 | A | 9/1998 | Morrison et al. | | |
| 6,197,596 | B1* | 3/2001 | Newkirk | | G01N 33/564 |
| | | | | | 530/395 |
| 6,576,741 | B1* | 6/2003 | Åkesson | | C07K 14/315 |
| | | | | | 530/350 |
| 10,436,797 | B2 | 10/2019 | Yerramilli et al. | | |
| 10,725,052 | B2 | 7/2020 | Yerramilli et al. | | |
| 12,385,927 | B2* | 8/2025 | Yerramilli | | C07K 14/8139 |
| 2002/0010125 | A1* | 1/2002 | Carson | | A61P 43/00 |
| | | | | | 435/372 |
| 2002/0015957 | A1* | 2/2002 | Hageman | | G01N 33/564 |
| | | | | | 351/200 |

| | | | | | |
|---|---|---|---|---|---|
| 2002/0136713 | A1* | 9/2002 | Laemmle | | A61K 38/4886 |
| | | | | | 424/94.63 |
| 2003/0143223 | A1* | 7/2003 | Cabezas | | A61P 9/10 |
| | | | | | 424/130.1 |
| 2004/0082534 | A1* | 4/2004 | Gleave | | A61K 31/712 |
| | | | | | 514/44 R |
| 2004/0132200 | A1 | 7/2004 | Albarella et al. | | |
| 2008/0064047 | A1* | 3/2008 | Zetter | | G01N 33/57407 |
| | | | | | 436/64 |
| 2013/0130285 | A1* | 5/2013 | Atkinson | | G01N 33/92 |
| | | | | | 435/7.92 |
| 2014/0038203 | A1 | 2/2014 | Arthur et al. | | |
| 2014/0038841 | A1* | 2/2014 | Sharif | | G01N 33/564 |
| | | | | | 530/387.9 |
| 2015/0160242 | A1 | 6/2015 | Athikomrattanakul et al. | | |
| 2016/0187348 | A1 | 6/2016 | Yerramilli et al. | | |
| 2017/0269101 | A1 | 9/2017 | Yerramilli et al. | | |
| 2017/0284954 | A1 | 10/2017 | Hughes et al. | | |
| 2018/0142009 | A1 | 5/2018 | Quinn et al. | | |
| 2018/0149612 | A1 | 5/2018 | Kumar et al. | | |
| 2020/0292558 | A1 | 9/2020 | Van Eyk et al. | | |
| 2021/0403603 | A1 | 12/2021 | Valdez et al. | | |
| 2022/0008250 | A1* | 1/2022 | Pollack | | A61F 9/0017 |
| 2022/0049270 | A1* | 2/2022 | Minassian | | C07K 14/8139 |
| 2022/0221446 | A1 | 7/2022 | Yerramilli et al. | | |

FOREIGN PATENT DOCUMENTS

| | | |
|---|---|---|
| EP | 0239400 A2 | 9/1987 |
| EP | 0519596 A1 | 12/1992 |
| EP | 0592106 A1 | 4/1994 |
| WO | WO 1991/009967 A1 | 7/1991 |

OTHER PUBLICATIONS

International Search Report and Written Opinion for PCT International Patent Application No. PCT/US2023/061371, mailed Dec. 23, 2024.
Bailey, "The Raising of a Polyclonal Antiserum to a Protein", Methods Mol. Biol., 1994, 32: 381-388.
Chen et al., "Selection and analysis of an optimized anti-VEGF antibody: crystal structure of an affinity-matured Fab in complex with antigen", J. Mol. Biol., Nov. 5, 1999, 293(3): 865-881.
Clackson et al., "Making antibody fragments using phage display libraries", Nature, Aug. 15, 1991, 352(6336): 624-628.
D'Amico et al., "Uncovering the cathepsin system in heart failure patients submitted to Left Ventricular Assist Device (LVAD) implantation", J Transl Med, Dec. 12, 2014, 12: 350.
Dean, "Preparation and characterization of monoclonal antibodies to proteins and other cellular components", Methods Mol. Biol., 1994, 32: 361-379.
Dean, "Preparation and testing of monoclonal antibodies to recombinant proteins", Methods Mol. Biol., 1998, 80: 23-37.
Dowbenko et al., "Epitope mapping of the human immunodeficiency virus type 1 gp120 with monoclonal antibodies", J. Virol., Dec. 1988, 62(12): 4703-4711.
Drenckhahn et al., "Production of polyclonal antibodies against proteins and peptides", Methods Cell. Biol., 1993, 37: 7-56.

(Continued)

*Primary Examiner* — Changhwa J Cheu

(74) *Attorney, Agent, or Firm* — Lathrop GPM LLP; Lisa Hillman

(57) ABSTRACT

The disclosure provides methods and compositions for detection and differentiation of stable CKD and progressive CKD in mammals.

16 Claims, 31 Drawing Sheets

Specification includes a Sequence Listing.

(56)                    References Cited

OTHER PUBLICATIONS

Gillies et al., "High-level expression of chimeric antibodies using adapted cDNA variable region cassettes", J. Immunol. Methods, Dec. 20, 1989, 125(1-2): 191-202.

Green et al., "Cystatin-like cysteine proteinase inhibitors from human liver", Biochem J., Mar. 15, 1984, 218(3): 939-946.

Gullick, "Production of antisera to synthetic peptides", Methods Mol. Biol., 1994, 32: 389-399.

Jarvinen et al., "Human spleen cysteineproteinase inhibitor: Purification, fractionation into isoelectric variants and some properties of the variants", Biochim Biophys Acta, Nov. 9, 1982, 708(2): 210-217.

Kohler et al., "Continuous cultures of fused cells secreting antibody of predefined specificity", Nature, 1975, 256(5517): 495-497.

Maino et al., "Rapid flow cytometric method for measuring lymphocyte subset activation", Cytometry, Jun. 1, 1995, 20(2): 127-133.

Marks et al., "By-passing immunization. Human antibodies from V-gene libraries displayed on phage", J. Mol. Biol., Dec. 5, 1991, 222(3): 581-597.

Morrison, "In vitro antibodies: strategies for production and application", Ann. Rev. Immunol., 1992, 10: 239-265.

Morrison, "Transfectomas Provide Novel Chimeric Antibodies", Science, Sep. 20, 1985, 229(4719): 1202-1207.

NCBI Reference Sequence: XP_023094432.1, CSTB cystatin B [*Felis catus* (domestic cat)], Gene ID: 102900380, updated on Mar. 10, 2024, obtained from url: <https://www.ncbi.nlm.nih.gov/gene/?term=NCBI%20Reference%20Sequence%3A%20XP_023094432.1#summary>.

Ocheing et al., "Cystatin Superfamily", Journal of Health Care for the Poor and Underserved, Feb. 2010, 21(1 Suppl): 51-70.

Ol et al., "Chimeric Antibodies", BioTechniques, 1986, 4(3): 214-221.

Padlan, "A possible procedure for reducing the immunogenicity of antibody variable domains while preserving their ligand-binding properties", Molecular Immunology, Apr.-May 1991, 28(4-5): 489-498.

Roguska et al., "Humanization of murine monoclonal antibodies through variable domain resurfacing", PNAS, Feb. 1, 1994, 91(3): 969-973.

Sato et al., "Reshaping a human antibody to inhibit the interleukin 6-dependent tumor cell growth", Cancer Res., Feb. 15, 1993, 53(4): 851-856.

Studnicka et al., "Human-engineered monoclonal antibodies retain full specific binding activity by preserving non-CDR complementarity-modulating residues", Protein Engineering, Jun. 1994, 7(6): 805-814.

uniprot.org, "M3WKP2_FELCA", *Felis catus* (Cat) (*Felis silvestris catus*), Feb. 28, 2018, UniProtKB-M3WKP2, obtained from url: <https://www.uniprot.org/uniprotkb/M3WKP2/entry>.

uniprot.org, "P25473 Clus_Canlf", *Canis lupus familiaris* (Dog) (*Canis familiaris*), May 1, 1992, UniProtKB-P25473, obtained from url: <https://www.uniprot.org/uniprotkb/P25473/entry>.

Wright et al., "Genetically engineered antibodies: progress and prospects", Crit. Rev. Immunol., 1992, 12(3-4): 125-168.

Schanstra et al., "Diagnosis and Prediction of CKD Progression by Assessment of Urinary Peptides," J Am Soc Nephrol., Aug. 2015, 26(8): 1999-2010, Epublished Jan. 14, 2015.

* cited by examiner

Fig. 11

Inverse creatinine $$\max(slope\ ^{Missou}_{CREA^{-1}}) = 0.004879631\ \frac{dL}{mg\ *week}$$

$$\min(slope\ ^{Missou}_{CREA^{-1}}) = -0.01168712\ \frac{dL}{mg\ *week}$$

Normal range for inverse creatinine - Weeks

Fig. 12

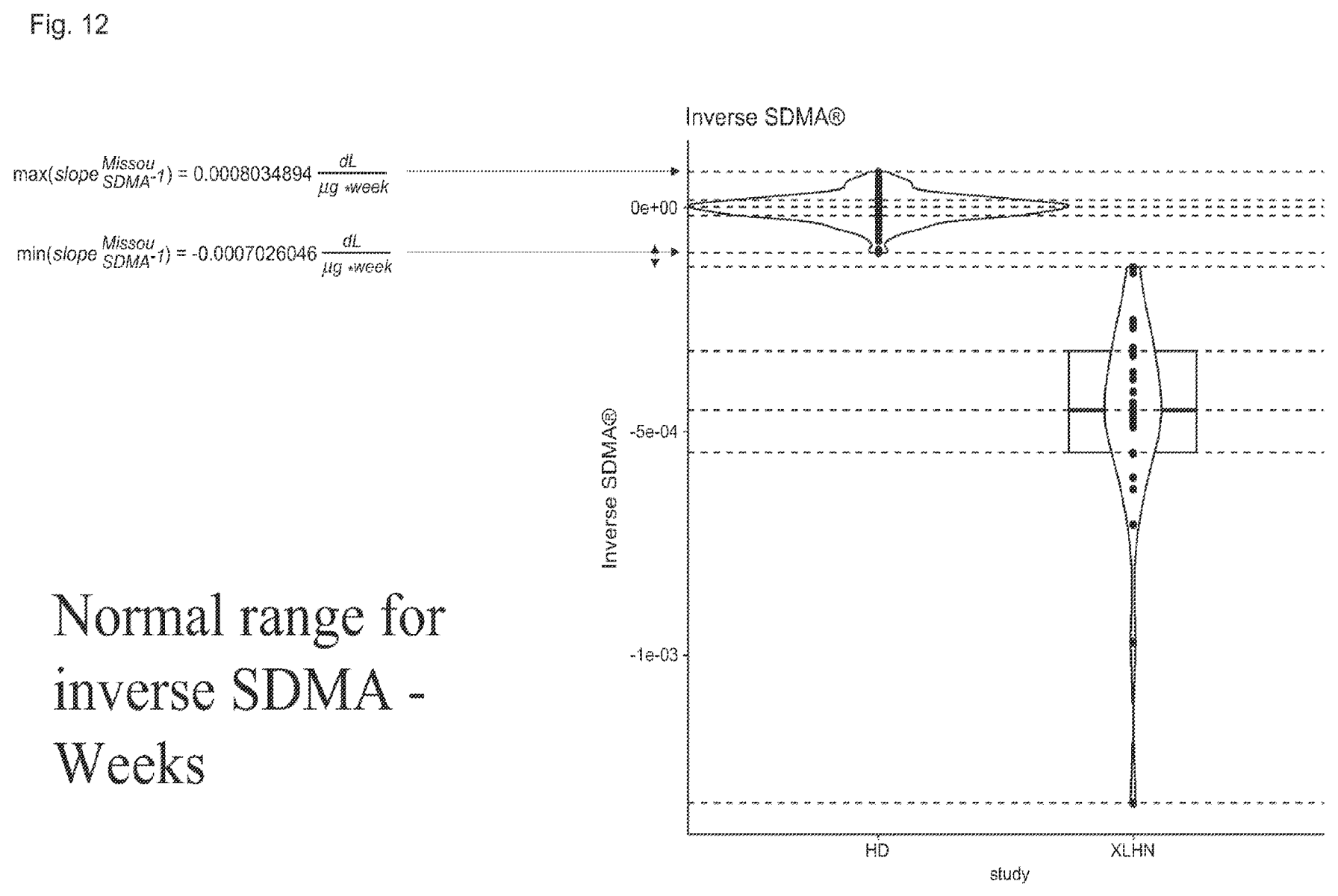

Inverse SDMA®

$\max(slope \frac{Missou}{SDMA^{-1}}) = 0.0008034894 \frac{dL}{\mu g \cdot week}$ $\min(slope \frac{Missou}{SDMA^{-1}}) = -0.0007026046 \frac{dL}{\mu g \cdot week}$ Normal range for inverse SDMA - Weeks Minimum change in inverse CREA slope: Weeks Normal to abnormal

Fig. 14

SEQUENCE LISTING

Sequence total quantity: 35
SEQ ID NO: 1              moltype = AA   length = 98
FEATURE                   Location/Qualifiers
source                    1..98
                          mol_type = protein
                          organism = Canis lupus
VARIANT                   52
                          note = Any amino acid
SEQUENCE: 1
MMCGAPSASQ PATADTQAIA DQVKAQLEER ENKKYTTFKA VTFRSQVVAG TXYFIKVQVD   60
DDEFVHLRVF QSLPHENKPL ALSSYQTNKA KHDELAYF                           98

SEQ ID NO: 2              moltype = AA   length = 98
FEATURE                   Location/Qualifiers
source                    1..98
                          mol_type = protein
                          organism = Felis catus SEQUENCE: 2
MMCGAPSATQ PATAETQAIA DQVKPQLEEQ ENKKYTTFKA VEFRSQVVAG RNYFIKVQVD   60
DDEFVHIRVF QSLPHENKPL ALSSYQTHKA RHDELAYF                           98

SEQ ID NO: 3              moltype = AA   length = 445
FEATURE                   Location/Qualifiers
source                    1..445
                          mol_type = protein
                          organism = Canis lupus
SEQUENCE: 3
MMKTLLLLVG LLLTWDNGRV LGDQAVSDTE LQEMSTEGSK YINKEIKNAL KGVKQIKTLI   60
EQTNEERKSL LSNLEEAKKK KEDALNDTKD SETKLKASQG VCNDTMMALW EECKPCLKQT   120
CMKFYARVCR SGSGLVGHQL EEFLNQSSPF YFWMNGDRID SLLENDRQQT HALDVMQDSF   180
NRASSIMDEL FQDRFFTREP QDTYHYSPFS LFQRRPFFNP KFRIARNIIP FPRFQPLNFH   240
DMFQPFFDMI HQAQQAMDVN LHRIPYHFPI EFPEEDNRTV CKEIRHNSTG CLKMKDQCEK   300
CQEILSVDCS SNNPAQVQLR QELSNSLQIA EKFTKLYDEL LQSYQEKMFN TSSLLKQLNE   360
QFSWVSQLAN LTQSEDPFYL QVTTVGSQTS DSNVPVGFTK VVVKLFDSDP ITVMIPEAVS   420
RNNPKFMETV AEKALQEYRQ KHREE                                        445

SEQ ID NO: 4              moltype = AA   length = 469
FEATURE                   Location/Qualifiers
source                    1..469
                          mol_type = protein
                          organism = Felis catus
SEQUENCE: 4
MTVSCSLQTE ACWDSRIGEP GTMKTLLLLV GLLLTCENGR VLGDKAVSDA ELQEMSTEGS   60
KYINKEIKNA LKGVKQIKTL IEQTNEERKS LLSNLEEAKK KKEDALSDTK DSEMKLKASE   120
GVCNDTMMAL WEECKPCLKQ TCMKFYARVC RSGSGLVGQQ LEEFLNQSSP FYFWINGDRI   180
DSLLENDRQQ THALDVMQDS FNRASRIMDE LFQDRFFTRE PQDTYHYSPF SSLQRRPFFF   240
NPKSRFARNV MPFPAFQPLN FHDMFQPFFD MIHQAQQAMD INLQRIPYHF PMEFTEEDNQ   300
DRMVCKEIRH NSTGCLRMKD QCDKCQEILS VDCSASNPSQ VLLRQELNNS LQMAEKFTKL   360
YDELLRSYQE KMFNTSSLLK QLNEQFSWVS QLANLTQSED PFYLQVTTVS SQTSDSNVPS   420
GFTKVVVKLF DSDPISVMVP EEVSRNNPKF METVAEKALQ EYRQKNGEK              469

SEQ ID NO: 5              moltype = AA   length = 21
FEATURE                   Location/Qualifiers
source                    1..21
                          mol_type = protein
                          organism = Canis lupus
SEQUENCE: 5
MMCGAPSASQ PATADTQAIA D                                             21

SEQ ID NO: 6              moltype = AA   length = 13
FEATURE                   Location/Qualifiers
source                    1..13
                          mol_type = protein
                          organism = Canis lupus
SEQUENCE: 6
QTNKAKHDEL AYF                                                      13

SEQ ID NO: 7              moltype = AA   length = 18
FEATURE                   Location/Qualifiers
source                    1..18
                          mol_type = protein
                          organism = Canis lupus
SEQUENCE: 7
CGAPSASQPA TADTQAIA                                                 18

SEQ ID NO: 8              moltype = AA   length = 8
FEATURE                   Location/Qualifiers -continued

```
source                    1..8
                          mol_type = protein
                          organism = Canis lupus
SEQUENCE: 8
CGAPSASQ                                                          8

SEQ ID NO: 9              moltype = AA   length = 9
FEATURE                   Location/Qualifiers
source                    1..9
                          mol_type = protein
                          organism = Canis lupus
SEQUENCE: 9
CAIADQVKA                                                         9

SEQ ID NO: 10             moltype = AA   length = 15
FEATURE                   Location/Qualifiers
source                    1..15
                          mol_type = protein
                          organism = Canis lupus
SEQUENCE: 10
FQSLPHENKP LALSS                                                  15

SEQ ID NO: 11             moltype = AA   length = 18
FEATURE                   Location/Qualifiers
source                    1..18
                          mol_type = protein
                          organism = Canis lupus
SEQUENCE: 11
SQVVAGTPYF IKVQVDDD                                               18

SEQ ID NO: 12             moltype = AA   length = 8
FEATURE                   Location/Qualifiers
source                    1..8
                          mol_type = protein
                          organism = Canis lupus
SEQUENCE: 12
KHDELAYF                                                          8

SEQ ID NO: 13             moltype = AA   length = 29
FEATURE                   Location/Qualifiers
source                    1..29
                          mol_type = protein
                          organism = Canis lupus
SEQUENCE: 13
MMCGAPSASQ PATADTQAIA DQVKAQLEE                                   29

SEQ ID NO: 14             moltype = AA   length = 8
FEATURE                   Location/Qualifiers
source                    1..8
                          mol_type = protein
                          organism = Canis lupus
SEQUENCE: 14
AIADQVKA                                                          8

SEQ ID NO: 15             moltype = AA   length = 18
FEATURE                   Location/Qualifiers
source                    1..18
                          mol_type = protein
                          organism = Canis lupus
SEQUENCE: 15
SQVVAGTNYF IKVQVDDD                                               18

SEQ ID NO: 16             moltype = AA   length = 18
FEATURE                   Location/Qualifiers
source                    1..18
                          mol_type = protein
                          organism = Canis lupus
SEQUENCE: 16
SQVVAGRNYF IKVQVDDD                                               18

SEQ ID NO: 17             moltype = AA   length = 8
FEATURE                   Location/Qualifiers
source                    1..8
                          mol_type = protein
                          organism = Canis lupus
SEQUENCE: 17
AIADQVKP                                                          8

SEQ ID NO: 18             moltype = AA   length = 29
```

-continued

```
FEATURE                Location/Qualifiers
source                 1..29
                       mol_type = protein
                       organism = Canis lupus
SEQUENCE: 18
MMCGAPSATQ PATAETQAIA DQVKPQLEE                              29

SEQ ID NO: 19          moltype = AA   length = 8
FEATURE                Location/Qualifiers
source                 1..8
                       mol_type = protein
                       organism = Canis lupus
SEQUENCE: 19
RHDELAYF                                                     8

SEQ ID NO: 20          moltype = AA   length = 18
FEATURE                Location/Qualifiers
source                 1..18
                       mol_type = protein
                       organism = Canis lupus
SEQUENCE: 20
SQVVAGRNYF IKVQVDDD                                          18

SEQ ID NO: 21          moltype = AA   length = 9
FEATURE                Location/Qualifiers
source                 1..9
                       mol_type = protein
                       organism = Canis lupus
SEQUENCE: 21
QAIADQVKP                                                    9

SEQ ID NO: 22          moltype = AA   length = 8
FEATURE                Location/Qualifiers
source                 1..8
                       mol_type = protein
                       organism = Canis lupus
SEQUENCE: 22
CGAPSATQ                                                     8

SEQ ID NO: 23          moltype = AA   length = 18
FEATURE                Location/Qualifiers
source                 1..18
                       mol_type = protein
                       organism = Canis lupus
SEQUENCE: 23
CGAPSATQPA TAETQAIA                                          18

SEQ ID NO: 24          moltype = AA   length = 13
FEATURE                Location/Qualifiers
source                 1..13
                       mol_type = protein
                       organism = Canis lupus
SEQUENCE: 24
QTHKARHDEL AYF                                               13

SEQ ID NO: 25          moltype = AA   length = 21
FEATURE                Location/Qualifiers
source                 1..21
                       mol_type = protein
                       organism = Canis lupus
SEQUENCE: 25
MMCGAPSATQ PATAETQAIA D                                      21

SEQ ID NO: 26          moltype = AA   length = 4
FEATURE                Location/Qualifiers
source                 1..4
                       mol_type = protein
                       organism = Canis lupus
SEQUENCE: 26
LAYF                                                         4

SEQ ID NO: 27          moltype = AA   length = 5
FEATURE                Location/Qualifiers
source                 1..5
                       mol_type = protein
                       organism = Canis lupus
SEQUENCE: 27
ELAYF                                                        5
```

-continued

```
SEQ ID NO: 28          moltype = AA  length = 6
FEATURE                Location/Qualifiers
source                 1..6
                       mol_type = protein
                       organism = Canis lupus
SEQUENCE: 28
DELAYF                                                          6

SEQ ID NO: 29          moltype = AA  length = 7
FEATURE                Location/Qualifiers
source                 1..7
                       mol_type = protein
                       organism = Canis lupus
SEQUENCE: 29
HDELAYF                                                         7

SEQ ID NO: 30          moltype = AA  length = 9
FEATURE                Location/Qualifiers
source                 1..9
                       mol_type = protein
                       organism = Canis lupus
SEQUENCE: 30
AKHDELAYF                                                       9

SEQ ID NO: 31          moltype = AA  length = 10
FEATURE                Location/Qualifiers
source                 1..10
                       mol_type = protein
                       organism = Canis lupus
SEQUENCE: 31
KAKHDELAYF                                                      10

SEQ ID NO: 32          moltype = AA  length = 11
FEATURE                Location/Qualifiers
source                 1..11
                       mol_type = protein
                       organism = Canis lupus
SEQUENCE: 32
NKAKHDELAY F                                                    11

SEQ ID NO: 33          moltype = AA  length = 12
FEATURE                Location/Qualifiers
source                 1..12
                       mol_type = protein
                       organism = Canis lupus
SEQUENCE: 33
TNKAKHDELA YF                                                   12

SEQ ID NO: 34          moltype = AA  length = 14
FEATURE                Location/Qualifiers
source                 1..14
                       mol_type = protein
                       organism = synthetic construct
SEQUENCE: 34
EKALQEYRKK HREE                                                 14

SEQ ID NO: 35          moltype = AA  length = 13
FEATURE                Location/Qualifiers
source                 1..13
                       mol_type = protein
                       organism = synthetic construct
SEQUENCE: 35
QTNKAKHDEL TYF                                                  13
```

METHODS AND COMPOSITIONS FOR DIFFERENTIATING PROGRESSIVE CHRONIC KIDNEY DISEASE FROM STABLE CHRONIC KIDNEY DISEASE

PRIORITY

This application claims the benefit of U.S. Ser. No. 63/267,181 filed on Jan. 26, 2022, and U.S. Ser. No. 63/354,878, filed on Jun. 23, 2022, which are incorporated by reference in their entireties.

This application incorporates by reference a Sequence Listing entitled 741954_IDX_006_SL.xml, created on Apr. 19, 2023, which is 32,000 bytes in size.

BACKGROUND

Chronic Kidney Disease (CKD) may be associated with increased water consumption, frequent urination, diminished appetite, weight loss and muscle atrophy. Generally, by the time clinical symptoms of CKD develop, irreparable kidney damage has occurred. Early detection permits earlier treatment and in turn slows disease progression. Current treatment includes, for example, dialysis, resolution of any inciting factors, and a diet low in phosphorous and protein. Early detection is crucial for improved life span and quality of life.

In humans, CKD progression is divided into five stages. In companion animals, e.g., canines and felines, CKD progression is divided into four stages described by the International Renal Interest Society. Current methods for detecting CKD in mammals, e.g., canines, felines, and humans, include kidney ultrasound, biopsy, measurement of serum creatinine and symmetric dimethylarginine (SDMA), and measurement of urine protein and creatinine. Biopsy is invasive and thus limited in its capacity as an early screening or diagnostic test. Serum creatinine levels increase only after a substantial decline in glomerular function and have poor sensitivity for early, mild, or moderate CKD. Urine and serum creatinine are also affected by muscle mass, diet, and tubular secretion. Presently available methods of detecting and diagnosing CKD cannot differentiate stable CKD from progressive CKD in a timely manner.

SUMMARY

An embodiment provides a method for differentiating stable chronic kidney disease ("CKD") from progressive CKD in a subject diagnosed with CKD by: (a) determining the amount of Cystatin B polypeptides, clusterin polypeptides, or both, in a sample from the subject at a single time point, (b) comparing the amount of the Cystatin B polypeptides, clusterin polypeptides, or both in the sample to a control sample or control standard, wherein increased levels of Cystatin B polypeptides or clusterin polypeptides, or both in the sample as compared to the control sample or control standard is an indication of progressive CKD.

In some embodiments, the subject can be, prior to step (a), diagnosed with International Renal Interest Society CKD Stage I or CKD with a symmetric dimethyl-arginine (SDMA) value of up to 20 µg/dl. In some embodiments, the method can further include administering one or more treatments comprising: surgery for obstructed ureters, obstructive nephroliths or uroliths, dietary management, administration of enteric phosphate binders, antiproteinurics, administration of antihypertensives, fluid therapy to correct dehydration, management of acidosis, administration of diuretics, dialysis, correction of electrolyte abnormalities, administration of antiemetics, administration of antacids, administration of recombinant erythropoietin, holistic treatment, or combinations thereof to the subject. In some embodiments, the method can further include determining the amount of Cystatin B polypeptides, clusterin polypeptides, or both, in a sample from the subject at 2, 3, 4, 5, or more additional time points. In some embodiments, the amount of the Cystatin B polypeptides can be determined using one or more antibodies or specific binding fragments that specifically bind a Cystatin B polypeptide or one or more polypeptides set forth in SEQ ID NOs:1-2, 5-32, fragments thereof, or combinations thereof. In some embodiments, the clusterin polypeptides can be determined using one or more antibodies or specific binding fragments that specifically bind a clusterin polypeptide or one or more polypeptides set forth in SEQ ID NOs:3-4, fragments thereof, or combinations thereof. In some embodiments, determining the amount of Cystatin B polypeptides or clusterin polypeptides in a sample from the subject can include contacting the sample with one or more antibodies or specific binding fragments thereof that specifically bind a Cystatin B polypeptide, a clusterin polypeptide, or one or more polypeptides set forth in SEQ ID NOs:1-32 under conditions suitable for formation of complexes of the Cystatin B polypeptides or clusterin polypeptides and the one or more antibodies or specific binding fragments thereof, and detecting the complexes of Cystatin B polypeptides or clusterin polypeptides and the one or more antibodies or specific binding fragments thereof. In some embodiments, the antibodies or specific binding fragments thereof can be immobilized to a solid support. In some embodiments, the antibodies or specific binding fragments thereof can be conjugated to one or more labels. In some embodiments, the method can further include contacting the complexes of the Cystatin B polypeptides or the clusterin polypeptides and the one or more antibodies or specific binding fragments thereof with an indicator agent. In some embodiments, the subject can be a non-human mammal. In some embodiments, the non-human mammal can be a canine or a feline. In some embodiments, the sample can be blood, serum, plasma, or urine. In some embodiments, the amount of Cystatin B or clusterin polypeptides can be determined by an immunoassay, a competitive immunoassay, a sandwich immunoassay, an enzyme-linked immunosorbent assay (ELISA), a turbidimetric immunoassay, a particle-enhanced turbidimetric immunoassay, a radioimmunoassay (RIA), or a western blot assay. In some embodiments, determining the amount of Cystatin B or clusterin polypeptides can include subjecting the sample to mass spectrometry, LC-MS, quantitative nuclear magnetic resonance (qNMR), amino acid analysis (AAA), chromatographic (HPLC) mass balance assay, or combinations thereof. In some embodiments, the control sample or control standard can be derived from normal, healthy subjects. In some embodiments, the control sample can be derived from subjects having stable CKD.

Specific embodiments will become evident from the following more detailed description of certain preferred embodiments and the claims.

BRIEF DESCRIPTION OF THE DRAWINGS

FIG. 11 shows how normal biomarker range for inverse creatinine is determined.

FIG. 12 shows how normal biomarker range for inverse SDMA is determined.

FIG. 14 shows how minimum change in inverse SDMA slope from normal to abnormal is determined.

Figure 1:
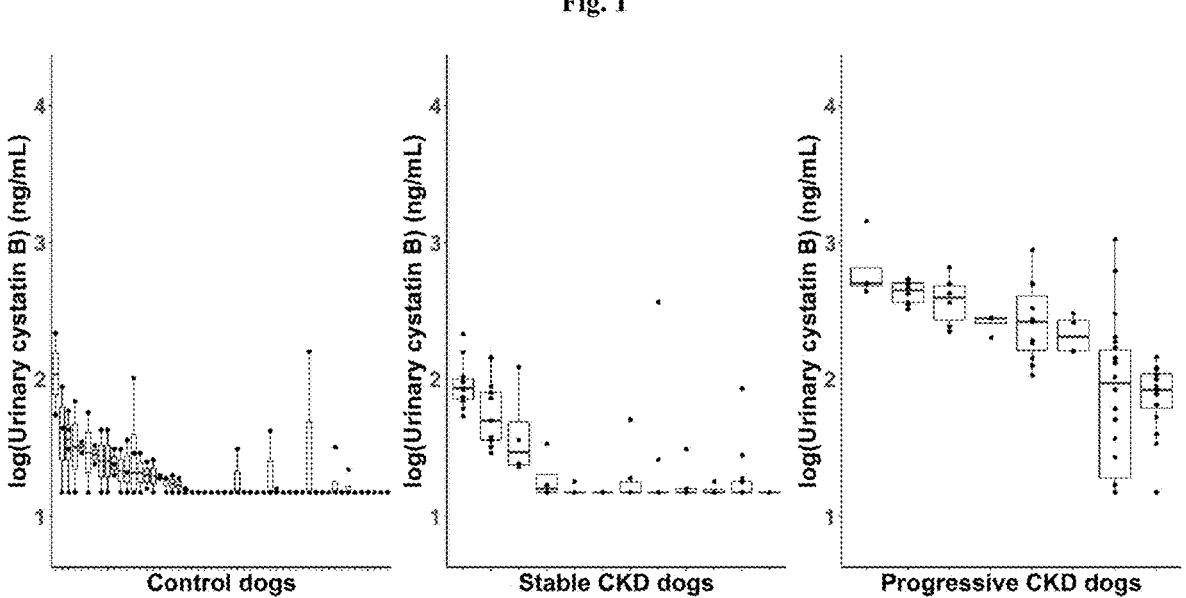
FIG. 1 shows uCysB values of each dog, grouped by disease status. Control and stable CKD dogs appear to have similar uCysB values. Progressive CKD dogs tend to have larger uCysB values compared to control and stable CKD dogs. Serial measurements for a given dog do not appear to be independent.

These and other objects and features will be better understood from the following detailed description taken in conjunction with the drawings.

DETAILED DESCRIPTION

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

Overview

Chronic kidney disease (CKD) is defined as presence of structural or functional abnormalities in the kidney for >3 months. Changes such as fibrosis and degeneration of the kidney parenchyma predominate. CKD is irreversible and tends to be progressive in nature. CKD is typically diagnosed based on changes in functional markers, such as serum creatinine and symmetric dimethylarginine (SDMA) concentration, which are also used to monitor the disease progression. Yet these functional markers can be insensitive in early CKD due to the nonlinear relationship with glomerular filtration rate (GFR) and due to a relatively wide reference range for both creatinine and SDMA. Markers of active ongoing injury (Acute Kidney Injury; AKI) can also be increased in some dogs with CKD, indicating that active ongoing injury is also present in dogs with CKD, even when the disease seems to be stable based on functional markers. Therefore, CKD and AKI may not be completely separate processes and may share some common characteristics.

Although CKD tends to be progressive in all dogs, the degree of progression varies substantially among dogs. Such differences in progression can be observed in the rate of change, or slope, of functional renal biomarkers (e.g. creatinine, SDMA). When assessing progression of CKD functional renal biomarker values can be converted to their reciprocals ("inverse biomarker"), from which slopes ("inverse slopes") can be calculated. Several risk factors for CKD progression have been identified, including the degree of renal proteinuria as reflected by urine protein:creatinine (UPC) ratio, hypertension, and hyperphosphatemia. It is possible that the degree of active injury in dogs with CKD might serve as a surrogate marker for the progression rate, regardless of the underlying cause.

Stage 1 chronic kidney disease (CKD) based on IRIS guidelines is typically associated with being more stable than CKD in advanced stages. However, some IRIS Stage 1 CKD dogs, specifically those with progressive CKD, may have active, ongoing injury as reflected by elevated uCysB values throughout the follow-up period. Further, uCysB can provide an earlier indicator of such injury compared to traditional biomarkers.

CKD in dogs and cats is a multifactorial disorder with multiple implicated etiologies. In the majority of animals with CKD, an underlying cause cannot be identified or eliminated. In the absence of an identifiable cause that can be eliminated, therapy is focused on dietary intervention, which has been shown to slow down progression rate, and controlling risk factors for rapid progression (e.g., hypertension, proteinuria). Once the disease has progressed to more advanced stages, treatment transitions to a more symptomatic focus. Therefore, a major therapeutic goal is to identify the disease early in its course and to slow down the progression rate before substantial irrecoverable damage occurs.

Diagnosis of CKD stage 1 is challenging and additional methods of kidney injury detection are needed. At present, the diagnosis of CKD often cannot rely on functional markers. As such, early diagnosis is based on presence of persistently non-concentrated urine (after exclusion of all other potential causes), presence of renal proteinuria, and ultrasonographic changes (which are often subtle and inconclusive at this stage of the disease). Many of these techniques require multiple visits to the veterinarian. Further diagnostics include measurement of the GFR and kidney biopsy, neither of which are routinely obtained in the clinical setting. As described herein 75% of progressive CKD dogs had elevated uCysB at first visit compared to only eight percent of stable dogs. Further, 67% of progressive CKD dogs with elevated uCysB progressed beyond IRIS stage 1. As demonstrated here, uCysB can be applied as an early biomarker differentiating stable and progressive CKD in IRIS stage 1.

In this study, the concentration of uCysB during the follow up period was higher in dogs with rapid progression compared with stable dogs. This implies that the degree of active ongoing injury, regardless of the cause and underlying etiology, might be used as a surrogate marker for intra-renal active injury resulting in loss kidney function, which is likely irreversible (i.e., fibrosis). It is yet to be determined if therapeutic intervention might be able slow down this progression, however the fact that that a real time marker of kidney injury is available will facilitate real time assessment of various therapeutic interventions in animals with CKD.

To date, therapeutic interventions are typically monitored using functional markers, which are very slow to change. Thus a very long follow up time is required to assess these interventions during which other factors, some of which are possible to identify and control while others are not, might have also influenced the progression rate. Due to the very long period of time required to assess the effect of therapeutic interventions in dogs with early kidney disease, such studies are difficult and cost prohibitive to conduct. Yet these interventions are likely more relevant at the early stages of the disease before most of the kidney has undergone substantial irreversible changes. In this context, real time markers such as uCysB are valuable and will allow better understanding of the intrarenal processes governing CKD and the potential interventions to ameliorate these processes.

Herein the slope of SDMA is used to assess the disease progression rate. Despite the high prevalence of CKD in dogs and cats, there are no definitions or guidelines established to differentiate animals with slow versus moderate or high progression rate. Percent change or absolute change in creatinine or SDMA concentration might be used to define the progression, however the time during which these changes occur is critical to determine the progression rate (i.e., an increase in creatinine of 0.5 mg/dL might define a dog as rapidly progressive if occurring over 2 months and slowly progressive if occurring over 3 years). For this study, the slope of at least 3 time points over at least 3 months was used to take into consideration the time effect and to assess the progression rate.

uCysB and clusterin (as described below) are biomarkers for detection of intrarenal injury in animals with CKD and a potential surrogate marker for the progression rate. In Stage I CKD, uCysB and clusterin can differentiate stable versus progressive CKD thus creating opportunities for arrest of progression and improved patient management.

Stable Chronic Kidney Disease and Progressive Kidney Disease

Compositions and methods described herein can be used to differentiate progressive CKD from stable CKD in mammals such as canines, felines, and humans that have been diagnosed with CKD. The advancement of progressive CKD and stable CKD can also be monitored. Progressive CKD and stable CKD can result in (1) decreased kidney function as compared to healthy subjects; or (2) physical damage to the kidneys; or (3) both. In some embodiments CKD (both progressive and stable) does not include cancer or does not include renal cancer. Markers for cancer including renal cancer can be different from those for stable or progressive CKD. In some embodiments the stable or progressive CKD does not encompass cancer, e.g., renal cancer or bladder cancer.

CKD is a condition characterized by a gradual loss of kidney function over time. CKD can be present in a stable form or a progressive form. Progressive or stable CKD can be glomerular or tubular. As CKD worsens, wastes can build to high levels in the blood and high blood pressure, anemia, weak bones, poor nutritional health and nerve damage can occur. CKD increases the risk of heart and blood vessel disease and can eventually lead to kidney failure. CKD can be caused by, e.g., diabetes, high blood pressure, and other disorders. Early detection and treatment can often keep the disease from getting worse.

The stages of CKD in canines as established by the International Renal Interest Society ("IRIS") are shown in Table 1.

TABLE 1

| | | Stage I Nonazotemic CKD | Stage II Mild renal azotemia | Stage III Moderate renal azotemia | Stage IV Severe renal azotemia |
|---|---|---|---|---|---|
| Serum Creatinine Concentration | mg/dL | <1.4 | 1.4-2.8 | 2.9-5.0 | >5.0 |
| | Mmol/L | <125 | 125-250 | 251-440 | >440 |

TABLE 1-continued

| | | Stage I Nonazotemic CKD | Stage II Mild renal azotemia | Stage III Moderate renal azotemia | Stage IV Severe renal azotemia |
|---|---|---|---|---|---|
| symmetric dimethyl-arginine (SDMA) | µg/dl | <18 | 18-35 | 36-54 | >54 |

The stages of CKD in felines as established by the International Renal Interest Society are shown in Table 2.

TABLE 2

| | | Stage I Nonazotemic CKD | Stage II Mild renal azotemia | Stage III Moderate renal azotemia | Stage IV Severe renal azotemia |
|---|---|---|---|---|---|
| Serum Creatinine Concentration | mg/dL | <1.6 | 1.6-2.8 | 2.9-5.0 | >5.0 |
| | Mmol/L | <140 | 140-250 | 251-440 | >440 |
| symmetric dimethyl-arginine (SDMA) | µg/dl | <18 | 18-25 | 26-38 | >38 |

A change in functional kidney markers (e.g., creatinine or SDMA) over time can be used to detect CKD. There are, however, several problems with using these markers to determine if a subject has stable or progressive CKD. Most notably, these markers must be observed over time to determine if the CKD is stable or progressive. Irreversible kidney damage can occur during the time required to observe any trend in the level of markers. Additionally, the use of blood creatinine is relatively insensitive as an early indicator of CKD. Levels of creatinine in healthy dogs and cats can overlap with values of creatinine in dogs and cats with mild to moderate kidney disease. Furthermore, other problems with the use of creatinine as a marker include that creatinine can vary based on muscle mass, there is no standardization of blood creatinine measurements across veterinary diagnostic laboratories, consumption of meat based diets can lead to absorption of creatinine post-prandially requiring the use of fasted samples (ideally 12 hours of fasting), and a large proportion of kidney tissue has to be damaged before a rise in blood creatinine concentration is detectable. The use of SDMA as a marker for CKD also has drawbacks including an increase of SDMA in dogs and cats with diseases other than CKD (e.g., hyperthyroidism or hypoadrenocorticism), significant differences in SDMA levels in different breeds of dogs and cats, and hemolysis of samples can cause interference in measuring SDMA. Therefore, a reliable marker that does not need to be measured over time to determine if a CKD patient has stable or progressive CKD can be instrumental in preventing kidney disease.

Surprisingly, it has been discovered that the use of Cystatin B ("CysB") and/or clusterin markers can determine, without the use of two or more tests over time, if a CKD patient has stable or progressive CKD. It was unknown, prior to the instant disclosure whether a marker existed that could be used to differentiate stable CKD from progressive CKD at a single time point.

Though referred to as "stable CKD," stable CKD can progress through IRIS CKD stages I-IV. However, stable CKD that progresses through the four stages can be contrasted with progressive CKD, where symptoms can progress or worsen at a faster rate over time than symptoms of stable CKD.

A patient with stable CKD will have no substantial change in functional kidney markers such as creatinine or SDMA over time (e.g., over 1, 2, 3, 4, 5, 6, 7, 8, 9, 10, 11, 12, 18, 24, 36, months or more (and any range between about 1 and about 36 months, e.g., about 1 to about 3, about 2 to about 4, about 3 to about 6, about 6 to about 12, or about 1-36 months). No substantial change in functional kidney markers means less than about 2, 5, 10, 20, or 25 percent increase in the amount of functional kidney markers in a CKD patient. An increase in the amount of functional kidney markers in progressive CKD can be an increase of about 21, 25, 30, 35, 40% or more over time (e.g., over 5 days, 1, week, 2 weeks, 3 weeks, 1, 2, 3, 4, 5, 6, 7, 8, 9, 10, 11, 12, 18, 24, 36 months or more (and any range between about 5 days and about 36 months, e.g., about 1 to about 3, about 2 to about 4, about 3 to about 6, about 6 to about 12, or about 1-36 months).

Provided herein are methods of determining if a patient diagnosed with CKD has stable CKD or progressive CKD by determining levels of Cystatin B, clusterin, or both at, for example, a single time point. In some embodiments, the mammalian CKD patient is in IRIS Stage I or has an SDMA value of up to 20. Where a mammal CKD patient has a urine Cystatin B level of above about 50, 60, 70, 80, 90, 100 ng/mL or more of Cystatin B (or any range between about 50 and 100 ng/mL or more (e.g., about 50-100 ng/mL or more, about 50-80 ng/mL or more, about 70-100 ng/mL or more)), then the patient is diagnosed with progressive CKD. These are considered "elevated amounts" of Cystatin B. Where a mammalian CKD patient has a urine level of above about 250, 260, 270, 280, 290, 300, 310, 320, 330, 340, 350 ng/mL or more of clusterin (or any range between about 250 and 350 ng/mL or more (e.g., about 250-300 ng/mL or more, about 275-325 ng/mL or more, about 325-350 ng/mL or more)), then the patient is diagnosed with progressive CKD. These are considered "elevated amounts" of clusterin.

Also provided herein are methods of determining if a patient diagnosed with CKD has stable CKD by determining levels of Cystatin B, clusterin, or both at, for example, a single time point. In some embodiments, the mammalian CKD patient is in IRIS Stage I or has an SDMA value of up to 20. Where a mammalian CKD patient has a urine Cystatin B level of about 20, 30, 40, 50, 60, 70, 80, 90, 100 ng/mL or more of Cystatin B (or any range between about 20 and 100 ng/mL) then the patient is diagnosed with stable CKD. Where a mammalian CKD patient has a urine Cystatin B level of about 100, 90, 80, 70, 60, 50, 40, 30, 20 ng/mL or less of Cystatin B (or any range between about 100 and 20 ng/mL) then the patient is diagnosed with stable CKD.

The use of SDMA or creatinine at a single time point does not provide the same results as the use of Cystatin B or clusterin markers as described herein.

Polypeptides

Prior discovery and work by IDEXX Laboratories, Inc. related to cystatin B and clusterin has been described in U.S. Pat. No. 10,725,052; (Methods and compositions for the detection and diagnosis of renal disease and periodontal disease); U.S. Pat. No. 10,436,797, (Markers for renal disease); and U.S. Pat. Publ. 2018/0142009 (Specific Detection of Clusterin isoforms). Prior IDEXX work validating cystatin B and clusterin in canine kidney injury also included development of an in vitro cellular model of cultured canine kidney cells treated with nephrotoxic gentamicin. The clusterin isoform present in the cultured cellular supernatant had a unique glycosylation pattern in comparison to the clusterin isoform isolated from plasma, enabling antibody generation specifically targeted to the kidney-specific isoform. Purification of canine cystatin B from cultured canine kidney cells was determined by tryptic digestion followed by LC-MS, allowing for recombinant protein creation matching the native protein extracted from canine kidney cells using LC-MS. Clinical validation of cystatin B was previously confirmed in dogs presenting with kidney injury.

Cystatin B (CysB) is an intracellular protein belonging to the family of cysteine protease inhibitors. CysB is an intracellular protein and thus is not circulating at high serum concentrations. Cystatins A & B are members of family 1 of the cystatin superfamily and are relatively small proteins with around 11 kDa in size. In humans, these proteins are monomeric and about 11 kDa in size. They are not glycosylated and do not have the disulfide bridges seen in other cystatin superfamilies. They also lack signal sequences and are generally intra-cellular proteins confined to the cell. See, Ochieng & Chaudhuri, J Health Care Poor Underserved 2010, 21(1 Suppl):51. Some amount of Cystatin B is present in extracellular fluids including human urine. Cystatin B has been shown to inhibit members of the lysosomal cysteine proteinases, cathepsin family, specifically cathepsin B, H, and L. See Green et al., Biochem J 1984 218:939; D'Amico et al., J Transl Med 2014, 12:350; Jarvinen & Rinne, Biochim Biophys Acta 1982, 708:210-217.

Canine Cystatin B (SEQ ID NO:1) is:

```
    MMCGAPSASQPATADTQAIADQVKAQLEERENKKYTTFKAVTF

RSQVVAGTXYFIKVQVDDDEFVHLRVFQSLPHENKPLALSSYQ

TNKAKHDELAYF
```

(wherein the X can be any amino acid or wherein X can be P or N).

SEQ ID NO:1 can be used to detect feline or canine Cystatin B.

Fragments of canine Cystatin B can include:

```
                                       (SEQ ID NO: 5)
    MMCGAPSASQPATADTQAIAD (SEQ ID NO: 6)
    QTNKAKHDELAYF
    Cystatin B C Terminal "Peptide 9"

(SEQ ID NO: 7)
    CGAPSASQPATADTQAIA
    Cystatin B N-terminal "Peptide 3-20"

(SEQ ID NO: 8)
    CGAPSASQ
    Cystatin B N-terminal "Peptide 3-10"

(SEQ ID NO: 9)
    CAIADQVKA
    Cystatin B N-terminal "Peptide 18-25"

(SEQ ID NO: 10)
    FQSLPHENKPLALSS
    Cystatin B "Peptide 2"

(SEQ ID NO: 11)
    SQVVAGTPYFIKVQVDDD
    Cystatin B "Peptide 1"
```

-continued

```
                                       (SEQ ID NO: 12)
    KHDELAYF (SEQ ID NO: 13)
    MMCGAPSASQPATADTQAIADQVKAQLEE (SEQ ID NO: 14)
    AIADQVKA (SEQ ID NO: 15)
    SQVVAGTNYFIKVQVDDD
```

Feline Cystatin B is shown below (NCBI Reference Sequence: XP_023094432.1)

```
                                       (SEQ ID NO: 2)
    MMCGAPSATQ PATAETQAIA DQVKPQLEEQ

ENKKYTTFKA VEFRSQVVAG RNYFIKVQVD

DDEFVHIRVF QSLPHENKPL ALSSYQTHKA

RHDELAYF
```

Fragments of canine Cystatin B can include:

```
                                       (SEQ ID NO: 16)
    SQVVAGRNYFIKVQVDDD (SEQ ID NO: 17)
    AIADQVKP (SEQ ID NO: 18)
    MMCGAPSATQPATAETQAIADQVKPQLEE

SEQ ID NO: 19
    RHDELAYF

SEQ ID NO: 20
    SQVVAGRNYFIKVQVDDD

SEQ ID NO: 10
    FQSLPHENKPLALSS

SEQ ID NO: 21
    QAIADQVKP

SEQ ID NO: 22
    CGAPSATQ

SEQ ID NO: 23
    CGAPSATQPATAETQAIA

SEQ ID NO: 24
    QTHKARHDELAYF

SEQ ID NO: 25
    MMCGAPSATQPATAETQAIAD
```

Clusterin or Apolipoprotein J is a 75-80 kDa disulfide linked heterodimeric protein. Clusterin is part of many physiological processes including sperm maturation, lipid transportation, complement inhibition, tissue remodeling, membrane recycling, stabilization of stressed proteins, and promotion of inhibition of apoptosis. Clusterin polypeptides can be detected using any suitable method, including for example immunoassays. In some embodiments a combination of lectins and anti-clusterin antibodies and lectins can be used to detect clusterin. See e.g., US Pat. Publ. 20180142009. Lectins can be used that specifically bind to carbohydrates on human, canine, feline, equine, bovine, ovine, or simian clusterin isoforms. Lectins can also be used that specifically bind one or more plasma, serum, or kidney clusterin isoforms and that do not bind other clusterin isoforms.

Lectins are proteins that recognize and bind specific monosaccharide or oligosaccharide structures (carbohydrates). A lectin usually contains two or more binding sites for carbohydrate units. The carbohydrate-binding specificity of a certain lectin is determined by the amino acid residues that bind the carbohydrate. The binding strength of lectins to carbohydrates can increase with the number of molecular interactions. The dissociation constant for binding of lectins to carbohydrates is about $K_d$ of $10^{-5}$ to $10^{-7}$.

Lectins can be labeled with any type of label known in the art, including, for example, fluorescent, chemiluminescent, radioactive, enzyme, colloidal metal, radioisotope and bioluminescent labels.

In some embodiments, lectins can be used that specifically bind kidney specific clusterin and that do not specifically bind plasma or serum clusterin. In some embodiments, lectins that specifically bind N-acetylglucosamine are useful in the methods. Such lectins include, for example, WGA (wheat germ agglutinin), WGA1, WGA2, WGA3, sWGA, DSL lectin (*Datura stramonium* lectin), mannose binding lectin, PHA-L (*Phaseolus vulgaris* leucoagglutanin), PHA-E (*Phaseolus vulgaris* erythoagglutanin), and LEL (*Lycopersicon esculentum* (Tomato) lectin). Other lectins that can be used include, for example jacalin, STL lectin (*Solanum tuberosum*), LCA lectin (*Lens culinaris*), PSA lectin (*Pisum sativum* agglutinin), ECL lectin (*Erythina cristagalli*), RCA lectin (*Ricin communis*), DBA lectin (*Dolichos biflorus*), SBA lectin (soybean), and CONA lectin (concanavlin). Lectins are commercially available from, e.g., Vector Laboratories.

In some embodiments clusterin can be detected with a combination of an anti-clusterin antibody or specific binding fragment thereof and a one or more lectins that specifically bind clusterin, e.g., a kidney specific clusterin isoform. See, e.g., US Pat. Publ. 20180142009. Some non-limiting examples of anti-clusterin antibodies are Clusterin Canine, Sheep Polyclonal Antibody from BioVendor Laboratory Medicine, Inc. Commercial feline antibodies for clusterin can be, for example, but not limited to Clusterin/APOJ Mouse anti-Human, Bovine, Canine, Feline, Porcine, DyLight™ 650, Clone: Hs-3, Novus Biologicals™. In some embodiments, clusterin can be detected by contacting a sample with one or more antibodies or antigen binding fragments thereof that specifically bind clusterin and one or more lectins that specifically bind to carbohydrate moieties of kidney specific clusterin and that do not specifically bind to carbohydrate moieties of other clusterin isoforms (e.g., plasma clusterin, serum clusterin, or bloodborne, non-kidney specific clusterin). Complexes of kidney specific clusterin, the one or more antibodies or antigen binding fragments thereof that specifically bind clusterin, and the one or more lectins can be detected. The lectins can specifically bind N-acetylglucosamine. Lectins can be, for example, *Phaseolus vulgaris* leucoagglutanin (PHA-L), wheat germ agglutinin (WGA), WGA1, WGA2, WGA3, sWGA, *Phaseolus vulgaris* agglutinin-E (PHA-E), *Lycopersicon esculentum* lectin (LEL), *Datura stramonium* lectin (DSL), *Pisum sativum* agglutinin (PSA), or *Dolichos biflorus* lectin (DBA), for example. The one or more antibodies or antigen binding fragments thereof can be immobilized to a support. The sample and detectably labeled one or more lectins can be added to the support. The lectins can be immobilized to a support. The sample and detectably labeled one or more antibodies or antigen binding fragments thereof can be added to the support. The one or more antibodies or antigen binding fragments thereof, the one or more lectins (e.g., plasma clusterin, serum clusterin, or bloodborne, non-kidney specific clusterin), or both can be labeled with a detectable label.

Canine clusterin precursor polypeptide UniProtKB—P25473. is shown below:

(SEQ ID NO: 3)

```
MMKTLLLLVG LLLTWDNGRV LGDQAVSDTE

LQEMSTEGSK YINKEIKNAL KGVKQIKTLI

EQTNEERKSL LSNLEEAKKK KEDALNDTKD

SETKLKASQG VCNDTMMALW EECKPCLKQT

CMKFYARVCR SGSGLVGHQL EEFLNQSSPF

YFWMNGDRID SLLENDRQQT HALDVMQDSF

NRASSIMDEL FQDRFFTREP QDTYHYSPFS

LFQRRPFFNP KFRIARNIIP FPRFQPLNFH

DMFQPFFDMI HQAQQAMDVN LHRIPYHFPI

EFPEEDNRTV CKEIRHNSTG CLKMKDQCEK

CQEILSVDCS SNNPAQVQLR QELSNSLQIA

EKFTKLYDEL LQSYQEKMFN TSSLLKQLNE

QFSWVSQLAN LTQSEDPFYL QVTTVGSQTS

DSNVPVGFTK VVVKLFDSDP ITVMIPEAVS

RNNPKFMETV AEKALQEYRQ KHREE
```

The precursor polypeptide chain is cleaved proteolytically to remove the 22-mer secretory signal peptide and subsequently between residues 227/228 to generate the α and β chains. These are assembled in anti-parallel to give a heterodimeric molecule in which the cysteine-rich centers are linked by five disulfide bridges and are flanked by two predicted coiled-coil a-helices and three predicted amphipathic a-helices.

Feline clusterin precursor is shown below UniProtKB-M3WKP2:

(SEQ ID NO: 4)

```
MTVSCSLQTEACWDSRIGEPGTMKTLLLLVGLLLTC

ENGRVLGDKAVSDAELQEMSTEGSKYINKEIKNAL

KGVKQIKTLIEQTNEERKSLLSNLEEAKKKKEDAL

SDTKDSEMKLKASEGVCNDTMMALWEECKPCLKQT

CMKFYARVCRSGSGLVGQQLEEFLNQSSPFYFWIN

GDRIDSLLENDRQQTHALDVMQDSFNRASRIMDEL

FQDRFFTREPQDTYHYSPFSSLQRRPFFFNPKSRF

ARNVMPFPAFQPLNFHDMFQPFFDMIHQAQQAMDI

NLQRIPYHFPMEFTEEDNQDRMVCKEIRHNSTGCL

RMKDQCDKCQEILSVDCSASNPSQVLLRQELNNSL

QMAEKFTKLYDELLRSYQEKMFNTSSLLKQLNEQF

SWVSQLANLTQSEDPFYLQVTTVSSQTSDSNVPSG

FTKVWKLFDSDPISVMVPEEVSRNNPKFMETVAEK

ALQEYRQKNGEK
```

The precursor polypeptide chain is cleaved proteolytically to remove the 43-mer secretory signal peptide.

An antibody or specific binding fragment thereof that specifically binds one or more polypeptide of SEQ ID NOs:1-32, can be used to detect these polypeptides in a sample.

Methods are provided herein for the detection and quantification of Cystatin B and clusterin polypeptides (e.g., SEQ ID NOs:1-4) and fragments thereof (e.g., SEQ ID NOs:5-32). One embodiment provides a purified polypeptide comprising SEQ ID NOS:1-32 or a fragment thereof. A polypeptide fragment of SEQ ID NOs:1-32 can consist of less than about 95, 90, 80, 70, 60, 50, 40, 35, 30, 25, 20, 15, 10 (or any range between about 10 and about 95) contiguous amino acids. In one embodiment a polypeptide fragment consists of more than about 10, 15, 20, 25, 30, 35, 40, 50, 60, 70, 80, 90, or 95 contiguous amino acids of SEQ ID NOs:1-32. In one embodiment, a polypeptide or fragment thereof is non-naturally occurring.

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

The term "polypeptides" can refer to one or more of one type of polypeptide (a set of polypeptides). "Polypeptides" can also refer to mixtures of two or more different types of polypeptides (i.e., a mixture of polypeptides that includes but is not limited to full-length protein, truncated polypeptides, or polypeptide fragments). The terms "polypeptides" or "polypeptide" can each also mean "one or more polypeptides."

A polypeptide variant or differs by about, for example, 1, 2, 3, 4, 5, 6, 7, 8, 9, 10, or more amino acid residues (e.g., amino acid additions, substitutions or deletions) from a polypeptide shown in SEQ ID NOs:1-32 or a fragment thereof. Where this comparison requires alignment, the sequences are aligned for maximum homology. The site of variation can occur anywhere in the polypeptide.

Variant polypeptides can generally be identified by modifying one of the polypeptide sequences described herein, and evaluating the properties of the modified polypeptide to determine if it is a biological equivalent. A variant is a biological equivalent if it reacts substantially the same as a polypeptide described herein in an assay such as an immunohistochemical assay, an enzyme-linked immunosorbent Assay (ELISA), a turbidimetric immunoassay, a particle-enhanced turbidimetric immunoassay, a radioimmunoassay (RIA), immunoenzyme assay or a western blot assay, e.g., has 90-110% of the activity of the original polypeptide. In one embodiment, the assay is a competition assay wherein the biologically equivalent polypeptide is capable of reducing binding of the polypeptide described herein to a corresponding reactive antigen or antibody by about 80, 95, 99, or 100%. An antibody that specifically binds a corresponding polypeptide also specifically binds the variant polypeptide.

Variant polypeptides are at least about 80%, or about 81, 82, 83, 84, 85, 86, 87, 88, 89, 90, 91, 92, 93, 94, 95, 96, 97, 98, or 99% identical to the polypeptide sequences shown in SEQ ID NOs:1-32. For example, a variant polypeptide of SEQ ID NOs:1-32 can be about at least 99.5%, 99%, 98%, 97%, 96%, 95%, 94%, 90%, 87%, 84%, or 81% identical to SEQ ID NOs:1-32. Variant polypeptides have one or more conservative amino acid variations or other minor modifications and retain biological activity, i.e., are biologically functional equivalents to SEQ ID NOs1-32. A biologically active equivalent has substantially equivalent function when compared to the corresponding polypeptide.

Methods of introducing a mutation into an amino acid sequence are well known to those skilled in the art. See, e.g., Ausubel (ed.), Current Protocols in Molecular Biology, John Wiley and Sons, Inc. (1994); Maniatis et al., Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a functionally active variant polypeptide by replacing an amino acid that does not influence the function of a polypeptide can be accomplished by one skilled in the art.

The variant polypeptides can have conservative amino acid substitutions at one or more predicted non-essential amino acid residues. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. In one embodiment a polypeptide has about 1, 2, 3, 4, 5, 10, 20 or less conservative amino acid substitutions.

The terms "sequence identity" or "percent identity" are used interchangeably herein. To determine the percent identity of two polypeptide molecules or two polynucleotide sequences, the sequences are aligned for optimal comparison purposes (e.g., gaps can be introduced in the sequence of a first polypeptide or polynucleotide for optimal alignment with a second polypeptide or polynucleotide sequence). The amino acids or nucleotides at corresponding amino acid or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). In some embodiments the length of a reference sequence (e.g., SEQ ID NO:1) aligned for comparison purposes is at least 80% of the length of the comparison sequence, and in some embodiments is at least 90% or 100%. In an embodiment, the two sequences are the same length.

Ranges of desired degrees of sequence identity are approximately 80% to 100% and integer values in between. Percent identities between a disclosed sequence and a claimed sequence can be at least 80%, at least 83%, at least 85%, at least 90%, at least 95%, at least 98%, at least 99%, at least 99.5%, or at least 99.9%. In general, an exact match indicates 100% identity over the length of the reference sequence (e.g., SEQ ID NO:1).

Polypeptides and polynucleotides that are sufficiently similar to polypeptides and polynucleotides described herein (e.g., Cystatin B or clusterin polypeptides) can be used herein. Polypeptides and polynucleotides that are about 90, 91, 92, 93, 94 95, 96, 97, 98, 99 99.5% or more identical to polypeptides and polynucleotides described herein can also be used herein.

For example, a polynucleotide can have 80% 85%, 90%, 91%, 92%, 93%, 94%, 95%, 96%, 97%, 98%, 99% or more identity to SEQ ID NOs:1-32.

A polypeptide or antibody can be covalently or non-covalently linked to an amino acid sequence to which the polypeptide or antibody is not normally associated with in nature. Additionally, a polypeptide or antibody can be covalently or non-covalently linked to compounds or molecules other than amino acids. For example, a polypeptide or antibody can be linked to an indicator reagent, an amino acid spacer, an amino acid linker, a signal sequence, a stop transfer sequence, a transmembrane domain, a protein purification ligand, or a combination thereof. In one embodiment a protein purification ligand can be one or more C amino acid residues at, for example, the amino terminus or carboxy terminus of a polypeptide. An amino acid spacer is a sequence of amino acids that are not usually associated with a polypeptide or antibody in nature. An amino acid spacer can comprise about 1, 5, 10, 20, 100, or 1,000 amino acids.

A polypeptide can be produced recombinantly. A polynucleotide encoding a polypeptide can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. Polypeptides can be lyophilized, desiccated, or dried, for example freeze-dried.

Polynucleotides

An embodiment includes an isolated polynucleotide that encodes the one or more of the polypeptides disclosed herein. Polynucleotides contain less than an entire genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. In one embodiment the polynucleotides encode a polypeptide shown in SEQ ID NOs:1-32 or fragments thereof.

Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

Degenerate nucleotide sequences encoding polypeptides are also contemplated herein. Degenerate nucleotide sequences are polynucleotides that encode a polypeptide as described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also contemplated herein.

Polynucleotides can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide is operably linked when it is positioned adjacent to or close to one or more expression control elements, which direct transcription and/or translation of the polynucleotide.

Polynucleotides can be used, for example, as probes or primers, for example, PCR primers, to detect the presence of polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 6, 7, 8, 9, 10, 11, 12, 13, 14, 15, 16, 17, 18, 19, 20, 25, 30, 40, 50, 60, 70, 80, 90, 100, 125, 150, 175, 200 or more contiguous nucleotides that encode polypeptides described herein.

Antibodies

Antibodies and specific binding fragments thereof include antibody molecules that specifically bind to Cystatin B and clusterin polypeptides described herein, variant Cystatin B polypeptides and variant clusterin polypeptides described herein, or fragments thereof. An antibody can specifically bind multiple polypeptides. The term "antibodies" also includes any type of antibody molecule or specific binding fragment or molecule that specifically binds one or more Cystatin B polypeptides or fragments thereof or one or more clusterin polypeptides or fragments thereof, e.g., SEQ ID NO:1-32. The term "antibodies" also includes any type of antibody molecule or specific binding fragment that specifically binds one or more Cystatin B polypeptides or clusterin polypeptides (e.g., SEQ ID NOs:1-32). An antibody can be naturally occurring, non-naturally occurring, synthetic, or genetically engineered. The terms "antigen-binding portion"

of an antibody, "antigen-binding fragment" of an antibody, and the like, as used herein, include any naturally occurring, enzymatically obtainable, synthetic, or genetically engineered polypeptide, glycoprotein or immunoglobulin that specifically binds Cystatin B polypeptides (e.g., SEQ ID NOs:1-32) to form a complex.

An antibody or specific binding fragment thereof binds to an epitope of a polypeptide described herein. An antibody can be made in vivo in suitable laboratory animals or in vitro using recombinant DNA techniques. Means for preparing and characterizing antibodies are well known in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide described herein to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

An antibody can be any isotype including IgG (IgG1, IgG2, IgG2a, Ig2b, IgG3, IgG4), IgM, IgA (IgA1 and IgA2), IgD, and IgE.

An antibody can be a monoclonal antibody, a polyclonal antibody, a chimeric antibody, or specific binding fragments thereof. A monoclonal antibody is an antibody obtained from a group of substantially homogeneous antibodies. A group of substantially homogeneous antibodies can contain a small amount of mutants or variants. Monoclonal antibodies are highly specific and interact with a single antigenic site. Each monoclonal antibody typically targets a single epitope, while polyclonal antibody populations typically contain various antibodies that target a group of diverse epitopes. Monoclonal antibodies can be produced by many methods including, for example, hybridoma methods (Kohler and Milstein, Nature 256:495, 1975), recombination methods (U.S. Pat. No. 4,816,567), and isolation from phage antibody libraries (Clackson et al., Nature 352:624-628, 1991; Marks et al., J. Mol. Biol. 222:581-597, 1991).

Antibodies that specifically bind mammalian (e.g., human, canine, and feline) Cystatin B and clusterin are known in the art. In some embodiments, commercial antibodies that bind to canine or feline clusterin or Cystatin B can be used. Commercial canine antibodies for clusterin can be, for example but not limited to, Anti-Clusterin/APOJ Antibody (STJ70776) from St John's Laboratory (EKA-LQEYRKKHREE SEQ ID NO:34) or Clusterin Canine, Sheep Polyclonal Antibody from BioVendor Laboratory Medicine, Inc. Commercial feline antibodies for clusterin can be, for example, but not limited to Clusterin/APOJ Mouse anti-Human, Bovine, Canine, Feline, Porcine, DyLight™ 650, Clone: Hs-3, Novus Biologicals™. Commercial antibodies for canine Cystatin B can be, for example, but not limited to, Goat anti-Cystatin B/Stefin B Antibody from MyBioSource.com (QTNKAKHDELTYF SEQ ID NO:35) or Goat Anti-Human Cystatin B/Stefin B, (C Terminus) from RayBiotech.

Chimeric antibodies or antigen-binding portions thereof have a part of a heavy chain and/or light chain that is derived from a specific species or a specific antibody class or subclass, and the remaining portion of the chain is derived from another species, or another antibody class or subclass. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397.

Chimeric antibodies can be produced using a variety of techniques including, for example, CDR-grafting (EP 239, 400; PCT publication WO 91/09967; U.S. Pat. Nos. 5,225, 539; 5,530,101; and 5,585,089), veneering or resurfacing (EP 592,106; EP 519,596; Padlan, Molecular Immunology 28:489-498 (1991); Studnicka et al., Protein Engineering 7(6):805-814 (1994); Roguska et al., PNAS 96:969-973 (1994)), and chain shuffling (U.S. Pat. No. 5,565,332).

In one embodiment, a chimeric antibody can comprise variable and constant regions of species that are different from each other, for example, an antibody can comprise the heavy chain and light chain variable regions of one mammal, and the heavy chain and light chain constant regions from a different animal (such as mouse, rabbit, canine, feline, or human). The chimeric antibody can comprise additional amino acid acids that are not included in the CDRs introduced into the recipient antibody, nor in the framework sequences. These amino acids can be introduced to more accurately optimize the antibody's ability to recognize and bind to an antigen. For example, as necessary, amino acids in the framework region of an antibody variable region can be substituted such that the CDR of a reshaped antibody forms an appropriate antigen-binding site. See Sato et al., Cancer Res. (1993) 53:851-856.

Non-limiting examples of specific binding portions or fragments of antibodies include: Fab fragments; Fab' fragments, Fab'-SH fragments, F(ab')$_2$ fragments; Fd fragments; Fv fragments; single-chain Fv (scFv) molecules; sdAb fragments (nanobodies); Fab-like antibodies (an antigen-binding fragment containing variable regions of a heavy chain and light chain that is equivalent to Fab fragments that are obtained by papain digestion); F(ab')$_2$-like antibodies (an antigen-binding fragment containing two antigen-binding domains that is equivalent to F(ab')$_2$ fragments that are obtained by pepsin digestion), multispecific antibodies prepared from antibody fragments, diabody, bispecific antibody, multifunctional antibody, humanized antibody, caninized antibody, human antibody, canine antibody, feline antibody, murine antibody, rabbit antibody, synthetic antibody, CDR-grafted antibody, and minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, CDR-grafted antibodies, diabodies, triabodies, tetrabodies, minibodies, nanobodies (e.g., monovalent nanobodies, bivalent nanobodies), single-chain (Fv)$_2$ (sc(Fv)$_2$); divalent (sc(Fv)$_2$); tetravalent ([sc(Fv)$_2$]$_2$) scFV antibodies, and small modular immunopharmaceuticals (SMIPs), and shark variable IgNAR domains, are also considered "antigen-binding fragments or portions," as used herein.

"Specifically binds," "specifically bind," or "specific for" means that a first antigen, e.g., a polypeptide of SEQ ID NOs:1-32, recognizes and binds to an antibody described herein with greater affinity than to other, non-specific molecules. "Specifically binds," "specifically bind" or "specific for" also means a first antibody, e.g., an antibody raised against SEQ ID NOs:1-32, recognizes and binds to SEQ ID NOs:1-32, with greater affinity than to other non-specific molecules. A non-specific molecule is an antigen that shares no common epitope with the first antigen. Specific binding can be tested using, for example, an enzyme-linked immunosorbent assay (ELISA), a radioimmunoassay (RIA), a turbidimetric immunoassay, a particle-enhanced turbidimetric immunoassay, or a western blot assay, or other suitable assay.

In an embodiment an antibody or antigen binding fragment thereof specifically binds to an epitope on a clusterin polypeptide set forth as SEQ ID NO:1, 2, 3, 4, 5, 6, 7, 8, 9, 10, 11, 12, 13, 14, 15, 16, 17, 18, 19, 20, 21, 22, 23, 24, or 25. In an embodiment the epitope is AYF, LAYF (SEQ ID NO:26), ELAYF (SEQ ID NO:27), DELAYF (SEQ ID NO:28), HDELAYF (SEQ ID NO:29), KHDELAYF (SEQ ID NO:12), AKHDELAYF (SEQ ID NO:30), KAKHDELAYF (SEQ ID NO:31), NKAKHDELAYF (SEQ ID NO:32), TNKAKHDELAYF (SEQ ID NO:33), or QTNKAKHDELAYF (SEQ ID NO:6).

In one embodiment an antibody or antigen binding fragment thereof competes for binding with a second or reference antibody to SEQ ID NO:1-32 or fragments thereof. Any competitive binding assays can be used to measure competition between two antibodies to the same antigen. For example, a sandwich ELISA assay can be used for this purpose. Means of assaying for cross-reactivity are well known to those of skill in the art (see, e.g., Dowbenko et al. (1988) J. Virol. 62: 4703-4711).

A first antibody is considered to competitively inhibit binding of a second antibody, if binding of the second antibody to the antigen is reduced by at least about 30%, 40%, 50%, 60%, 75%, 90% or more, in the presence of the first antibody using any of the assays used to assess competitive binding.

Competitive binding can be ascertained by providing one or more isolated polypeptides shown in SEQ ID NOs:1-32 attached to a solid support and assaying the ability of an antibody to bind to the polypeptides or to compete with an antibody described herein for binding to the polypeptides.

Antibodies include antibodies and antigen binding fragments thereof that (a) compete for binding with a reference antibody for binding to SEQ ID NOs:1-32 or antigen binding fragments thereof; (b) binds to the same epitope of SEQ ID NOs:1-32 or antigen binding fragments thereof as a reference antibody; (c) binds to SEQ ID NOs:1-32 or antigen binding fragments thereof with substantially the same $K_d$ as a reference antibody; and/or (d) binds to SEQ ID NOs:1-32 or fragments thereof with substantially the same off rate as a reference antibody, wherein the reference antibody is an antibody or antigen-binding fragment thereof that specifically binds to a polypeptide of SEQ ID NOs:1-32 or antigen binding fragments thereof with a binding affinity $K_a$ of $10^7$ l/mol or more.

The affinity of an antibody or antigen-binding fragment thereof for its polypeptide partner can be represented by a dissociation constant (Kd). The equilibrium dissociation constant (Kd) is calculated at the ration of $k_{off}/k_{on}$. See Chen, Y. et al., 1999, J. Mol. Biol. 293: 865-881. A variety of methods are known in the art for measuring affinity constants. In a particular embodiment, the reference antibody is an antibody or antigen-binding fragment thereof that has a binding affinity to a polypeptide of SEQ ID NOs:1-32 with a particular $K_{on}$ rate/association rate or $K_{off}$ rate. In one embodiment, the antibodies specifically bind with a $K_{on}$ of $6\times10^5$ $M^{-1}s^{-1}$ or better; antibodies specifically bind with a $K_{off}$ rate of $5\times10^{-6}$ $s^{-1}$ or better; or antibodies specifically binds with a binding affinity of 500 pM, 400 pM, 300 pM, 200 pM, 100 pM, 50 pM, 40 pM, 30 pM, 20 pM or better.

Antibodies that specifically bind SEQ ID NOs:1-32 or SEQ ID NOs:26-32 are particularly useful for detecting the presence of Cystatin B and clusterin polypeptides and fragments thereof present in a sample, such as a serum, blood, plasma, cells, tissue, saliva, plaque, crevicular fluid, gingival biopsy, tongue swab, or urine sample from an animal. An immunoassay can utilize one antibody or several antibodies. An immunoassay can use, for example, a monoclonal antibody specific for one epitope, a combination of monoclonal antibodies specific for epitopes of one polypeptide, monoclonal antibodies specific for epitopes of different polypeptides, polyclonal antibodies specific for the same antigen, polyclonal antibodies specific for different antigens, or a combination of monoclonal and polyclonal antibodies. Immunoassay protocols can be based upon, for example, competition, direct reaction, or sandwich type assays using, for example, labeled antibody. Antibodies can be labeled with any type of label known in the art, including, for example, fluorescent, chemiluminescent, radioactive, enzyme, colloidal metal, radioisotope and bioluminescent labels.

Antibodies or antigen-binding fragments thereof can be bound to a support and used to detect the presence or amount of polypeptides present in samples in certain diseases and conditions. Supports include, for example, glass, polystyrene, polypropylene, polyethylene, dextran, nylon, amylases, natural and modified celluloses, polyacrylamides, agaroses and maglelite. Antibodies or antigen-binding fragments thereof can be lyophilized, desiccated, or dried, for example, freeze-dried.

Antibodies can further be used to isolate polypeptides by immunoaffinity columns. The antibodies can be affixed to a solid support by, for example, absorption or by covalent linkage so that the antibodies retain their immunoselective activity. Optionally, spacer groups can be included so that the antigen binding site of the antibody remains accessible. The immobilized antibodies can then be used to specifically bind SEQ ID NOs:1-32 or fragments thereof from a biological sample, including but not limited to saliva, plaque, crevicular fluid, gingival biopsy, tongue swab, serum, blood, and urine.

Antibodies can also be used in immunolocalization studies to analyze the presence and distribution of a polypeptide described herein during various cellular events or physiological conditions. Antibodies can also be used to identify molecules involved in passive immunization and to identify molecules involved in the biosynthesis of non-protein antigens. Identification of such molecules can be useful in vaccine development. Antibodies, including, for example, monoclonal antibodies and single chain antibodies, can be used to monitor the course of amelioration of certain diseases or conditions. By measuring the increase or decrease in the amount of SEQ ID NOs:1-32 or SEQ ID NO:26-32 or fragments thereof in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection and Quantification of Polypeptides

One embodiment provides methods for detecting and quantifying Cystatin B, clusterin, SDMA, or creatinine polypeptides in a sample, for example, a mammalian urine sample. Methods for detecting and quantifying polypeptides include, for example, quantitative nuclear magnetic resonance (qNMR), amino acid analysis (AAA), chromatographic (HPLC) mass balance assay, liquid chromatography-mass spectrometry (LC-MS), and mass spectrometry.

qNMR utilizes its unique ability to achieve equal magnitude of response from magnetic nuclei, such as $^1$H, independent of chemical structure. AAA is based on quantifying stable amino acids following peptide hydrolysis. HPLC selectively quantifies an analyte of interest against a reference standard of the same analyte. In LC-MS, liquid chromatography (LC) separates the sample components and then introduces them to the mass spectrometer (MS). The MS creates and detects charged ions. The LC/MS data may be used to provide information about the molecular weight, structure, identity, and quantity of specific sample components. A mass spectrum obtained by mass spectrometry is a plot of the ion signal as a function of the mass-to-charge ratio. These spectra are used to determine the elemental or isotopic signature of a sample, the masses of polypeptides, and to elucidate the chemical identity or structure of polypeptides. Immunoassays (IAs) and competitive IAs can also be used to quantify polypeptides.

Polypeptides can also be detected and quantified using, e.g., antibodies or specific binding fragments thereof (e.g., polyclonal antibodies, monoclonal antibodies, and specific binding fragments thereof or a combination) in immunoassays. Such methods can comprise contacting a sample with one or more antibodies or specific binding fragments thereof specific for, e.g., SEQ ID NOs:1-32 or fragments thereof under conditions suitable for formation of complexes of the Cystatin B polypeptides or clusterin polypeptides and the one or more antibodies or specific binding fragments thereof. The complexes of Cystatin B polypeptides or clusterin polypeptides and the one or more antibodies or specific binding fragments specific for SEQ ID NOs:1-32 are detected and quantified.

SDMA and creatinine can be detected using, e.g., antibodies and/or ELISA kits. Example of ELISA kits include CREA ELISA kit product number MBS748495 MyBioSource (San Diego CA) and Canine Creatinine ELISA kit product number CNEB0472 AssayGenie (Dublin IE). Creatinine can also be detected using, e.g., electrochemical methods (US Pat. Publ. 20170284954; US Pat. Publ. 20180149612), polymer matrices (US Pat. Publ. 20150160242), and fluorescent methods (US Pat. Publ. 20040132200). SDMA can be detected with, for example, antibodies (US Pat. Publ. 20160187348); product number AB1N7845543 (Antibodies Online, Pottstown, PA); product number ABIN870728 (Antibodies Online, Pottstown, PA); see also US Pat. Publ. 20210403603 for detection of SDMA.

In an embodiment, methods for detecting and quantifying polypeptides comprising Cystatin B, clusterin, SDMA, creatinine, SEQ ID NOs:1-32 and fragments thereof are provided. The relative amounts of the polypeptides can be used to differentiate mammals with stable CKD from those with progressive CKD. Any method known in the art for detecting polypeptides can be used in the methods described herein.

Assay methods used in conjunction with the antibodies described herein can include direct and indirect labeling techniques, immunoaffinity columns, immunomagnetic beads, fluorescence activated cell sorting (FACS), enzyme-linked immunosorbent assays (ELISA), radioimmune assay (RIA), agglutination assays nephelometric assays, quantitative nephelometric assays, western blot, IFA, hemagglutination (HA), turbidimetric immunoassay, particle-enhanced turbidimetric immunoassay, fluorescence polarization immunoassay (FPIA), and microtiter plate assays (any assay done in one or more wells of a microtiter plate). One assay comprises a reversible flow chromatographic binding assay, for example a SNAP® assay. See e.g., U.S. Pat. No. 5,726,010.

Antibodies or specific binding fragments thereof can be detectably-labeled with, for example, fluorescent labels that have excitation and emission wavelengths adapted for detection using commercially-available instruments such as fluorescence activated cell sorters. Examples of fluorescent labels include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to antibodies using standard techniques (Maino et al., 1995, *Cytometry* 20: 127-133).

The methods described herein can be used to detect Cystatin B, clusterin, SDMA, creatinine, SEQ ID NOs:1-32 or fragments thereof wherein antibodies or antigen-binding antibody fragments specifically bind Cystatin B, clusterin, SDMA, creatinine, SEQ ID NOs:1-32.

As used herein, a "patient" or "subject" can mean a human or non-human animal including feline, bovine, porcine, equine, or canine.

The term "sample," "test sample," "patient sample," or "subject sample" as used herein includes but is not limited to a blood, serum, plasma, saliva, plaque, crevicular fluid, gingival biopsy, tongue swab, or urine sample obtained from a subject. The test sample can be untreated, precipitated, fractionated, separated, diluted, concentrated, or purified.

Assays can comprise solid phases or substrates or can be performed by immunoprecipitation or any other methods that do not utilize solid phases. Where a solid phase or substrate is used, one or more polypeptides or antibodies (or specific binding fragments thereof) are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment a substrate is sintered, fine particles of polyethylene, commonly known as porous polyethylene, for example, 10-15 micron porous polyethylene from Chromex Corporation (Albuquerque, NM). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing antibodies on solid phases include ionic, hydrophobic, covalent interactions and the like.

In one embodiment methods comprise contacting a test sample with one or a plurality of antibodies that specifically bind to Cystatin B, clusterin, SDMA, creatinine, SEQ ID NOs:1-32 or fragments thereof under conditions that allow polypeptide/antibody complexes, i.e., immunocomplexes, to form. That is, antibodies specifically bind to one or a plurality of polypeptides of Cystatin B, clusterin, SDMA, creatinine, SEQ ID NOs:1-32 or fragments thereof located in the sample. One of skill in the art is familiar with assays and conditions that are used to detect antibody/polypeptide complex binding. The formation of a complex between polypeptides and antibodies in the sample is detected. The formation of antibody/polypeptide complexes is an indication that polypeptides are present in the CKD patient sample at a certain amount.

In one embodiment, a polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The methods can optionally comprise a positive or negative control. A positive control can contain one or more polypeptides, which will specifically bind to antibodies specific for Cystatin B, clusterin, SDMA, or creatinine, and provide a positive result. A negative control does not contain any Cystatin B, clusterin, SDMA, or creatinine, polypeptides or any polypeptides or other components that would specifically bind or cross-react with antibodies specific for Cystatin B, clusterin, SDMA, or creatinine.

In one embodiment, one or more antibodies are covalently or non-covalently immobilized to a solid phase or substrate. A sample potentially comprising a Cystatin B, clusterin, SDMA, or creatinine, polypeptide is added to the substrate. One or more antibodies (or specific binding fragments) specific for Cystatin B, clusterin, SDMA, or creatinine, are added to the substrate. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment, one or more antibodies are immobilized to a solid phase or substrate. A test sample potentially containing Cystatin B, clusterin, SDMA, or creatinine, polypeptides is added to the substrate. Second anti-species antibodies that specifically bind Cystatin B, clusterin, SDMA, or creatinine, polypeptides are added. These second anti-species antibodies are from a different species than the antibodies immobilized to the solid phase. Third anti-species antibodies are added that specifically bind the second anti-species antibodies and that do not specifically bind the antibodies immobilized to the solid phase are added. The third anti-species antibodies can comprise an indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

In one embodiment, one or more capture antibodies can specifically bind to one or more epitopes of a polypeptide described herein. The capture antibody or antibodies can be used to immobilize one or a plurality of polypeptides of Cystatin B, clusterin, SDMA, creatinine, SEQ ID NOs:1-32 or fragments thereof to, for example, a solid support. One or more detection antibodies can specifically bind to the same one or more epitopes or different one or more epitopes of the polypeptides. The detection antibody can be used to detect or visualize the immobilization of the polypeptide to a solid support. This embodiment is advantageous because it is more specific and more sensitive than assays using only one antibody for both capture and detection functions.

In one type of assay format, one or more antibodies can be coated onto a solid phase or substrate. A test sample suspected of containing polypeptides comprising Cystatin B, clusterin, SDMA, creatinine, SEQ ID NO:1-32, or fragments thereof is incubated with an indicator reagent comprising a signal generating compound conjugated to an antibodies or antibody fragments specific for said polypeptides for a time and under conditions sufficient to form antigen/antibody complexes of either antibodies of the solid phase to the test sample polypeptides or the indicator reagent compound conjugated to an antibody specific for the polypeptides. The binding of the indicator reagent conjugated to anti-polypeptide antibodies to the solid phase can be quantitatively measured. A measurable alteration in the signal compared to the signal generated from a control sample or control standard indicates the presence of polypeptides comprising Cystatin B, clusterin, SDMA, or creatinine, SEQ ID NOs: 1-32 or fragments thereof. This type of assay can quantitate the amount of polypeptide in a test sample.

In another type of assay format, one or more antibodies are coated onto a support or substrate. An antibody is conjugated to an indicator reagent and added to a test sample. This mixture is applied to the support or substrate. If Cystatin B, clusterin, SDMA, or creatinine polypeptides are present in the test sample, they will bind the one or more antibodies conjugated to an indicator reagent and to the one or more antibodies immobilized on the support. The polypeptide/antibody/indicator complex can then be detected. This type of assay can quantitate the amount of polypeptide in a test sample.

In another type of assay format, one or more antibodies are coated onto a support or substrate. The test sample is applied to the support or substrate and incubated. Unbound components from the sample are washed away by washing the solid support with a wash solution. If polypeptides comprising Cystatin B, clusterin, SDMA, creatinine, SEQ ID NOs:1-32 or fragments thereof are present in the test sample, they will bind to the antibody coated on the solid phase. This polypeptide/antibody complex can be detected using a second anti-species specific antibody that is conjugated to an indicator reagent. The polypeptide/antibody/anti-species antibody indicator complex can then be detected. This type of assay can quantitate the amount of polypeptides in a test sample.

The formation of a polypeptide/antibody complex or a polypeptide/antibody/indicator complex can be detected by, for example, radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

The phrase "determining the amounts" as used herein refers to measuring or identifying the levels of one or more polypeptides in a sample. This can be accomplished by methodology well known in the art for the detection of polypeptides including using antibodies including, for example enzyme-linked immunosorbent assay (ELISA), a radioimmunoassay (RIA), a turbidimetric immunoassay, a particle-enhanced turbidimetric immunoassay, or a western blot assay, or immunohistochemistry assay. Alternatively, polypeptides of Cystatin B, clusterin, SDMA, creatinine, SEQ ID NOs:1-32 or fragments thereof, can be determined by mass spectrometry, LC-MS, quantitative nuclear magnetic resonance (qNMR), amino acid analysis (AAA), chromatographic (HPLC) mass balance assay, or similar methods known by one of skill in the art. Determining the amount of polypeptide present in a sample is accomplished by such in vitro analysis and experimental manipulation.

Methods of Diagnosis

One embodiment provides methods for diagnosing stable CKD or progressive CKD renal disease in a subject. A subject is first diagnosed with CKD and then the amount of Cystatin B or clusterin polypeptides in a sample from the CKD diagnosed subject is determined. The methods can comprise determining the amount of Cystatin B polypeptides, clusterin polypeptides, or both in a sample from the subject, wherein the amount of the Cystatin B or clusterin polypeptides is determined using, for example, one or more antibodies specifically bind Cystatin B, clusterin, SEQ ID NOs:1-32 or fragments thereof or other methods as described herein. The amount of Cystatin B or clusterin polypeptides in the sample is compared to a control sample or control standard, wherein certain levels of Cystatin B or clusterin polypeptides in the sample compared to the control sample or control standard is an indication of either stable CKD or progressive CKD renal disease in a subject.

Some embodiments provide a method for diagnosing or detecting stable or progressive CKD. The method comprises determining the amount of Cystatin B or clusterin polypeptides in a sample from the subject, wherein the amount of the Cystatin B polypeptides or clusterin is determined using one or more antibodies (or specific binding fragments) that specifically bind one or more polypeptides as set forth in SEQ ID NOs: 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32 or fragments thereof. The amount of the Cystatin B or clusterin polypeptides in the sample is compared to a control sample or control standard, wherein elevated levels of Cystatin B or clusterin polypeptides in the sample compared to the control sample or control standard is an indication of stable CKD or progressive CKD.

In some embodiments, antibody-independent methods can be used to diagnose or detect stable or progressive CKD. The method can comprise determining the amount of Cystatin B or clusterin polypeptides in a sample from the subject, wherein the amount of Cystatin B or clusterin is determined using LC-MS assay or other assays described herein. The amount of the Cystatin B or clusterin polypeptides in the sample is compared to a control sample or control standard, wherein elevated levels of Cystatin B or clusterin polypeptides in the sample compared to the control sample or control standard is an indication of stable CKD or progressive CKD.

Elevated levels of Cystatin B polypeptides can be levels that are about 10, 20, 30, 40, 50, 60, 70, 80, 90, 100, 200, 300, 400, 500% or more greater than control samples or control standards. Elevated levels of Cystatin B polypeptides can be levels that are about 10 to 500% or more; about 20 to 500% or more; about 30 to 500% or more; about 40 to 500% or more; about 50 to 500% or more; about 60 to 500% or more; about 100 to 500% or more than control samples or control standards.

Elevated levels of Cystatin B or clusterin polypeptides can also be levels that are statistically significantly increased amounts when compared to control samples or control standards.

As described above, elevated levels of Cystatin B polypeptides can also be above about 50, 60, 70, 80, 90, 100 ng/mL or more of Cystatin B (or any range between about 50 and 100 ng/mL or more (e.g., about 50-100 ng/mL or more, about 50-80 ng/mL or more, about 70-100 ng/mL or more)), Control levels or control standards of Cystatin B polypeptides can be about 49, 40, 30, 25, 20, 15, 10, 5, 1 or less ng/mL.

As described above, elevated levels of clusterin polypeptides can also be above about 250, 260, 270, 280, 290, 300, 310, 320, 330, 340, 350 ng/mL or more of clusterin (or any range between about 250 and 350 ng/mL or more (e.g., about 250-300 ng/mL or more, about 275-325 ng/mL or more, about 325-350 ng/mL or more). Control levels or control standards of Cystatin B polypeptides can be about 249, 240, 230, 225, 200, 150, 100, 50 or less ng/mL.

Elevated levels of Cystatin B or clusterin polypeptides can be compared to control samples or control standards that are determined using normal control subjects who do not have any type of kidney disease or condition, or bacterial infection.

Surprisingly, the use of inverse SDMA (1/SDMA) slope or inverse creatinine (1/creatinine) slope can also be used to differentiate if a CKD patient has stable or progressive CKD. No substantial change in functional kidney markers means less than 200% change from the inverse SDMA or inverse creatinine slope of a healthy population over the specified time period, respectively. The period of time can be e.g., over 1 week, 2 weeks, 3 weeks, four weeks, 1, 2, 3, 4, 5, 6, 7, 8, 9, 10, 11, 12, 18, 24, 36, months or more (or any range between about 1 week and about 36 months, e.g., about 1 to about 3, about 2 to about 4, about 3 to about 6, about 6 to about 12, or about 1-36 months). In these cases, a subject has stable chronic kidney disease.

Figure 13:
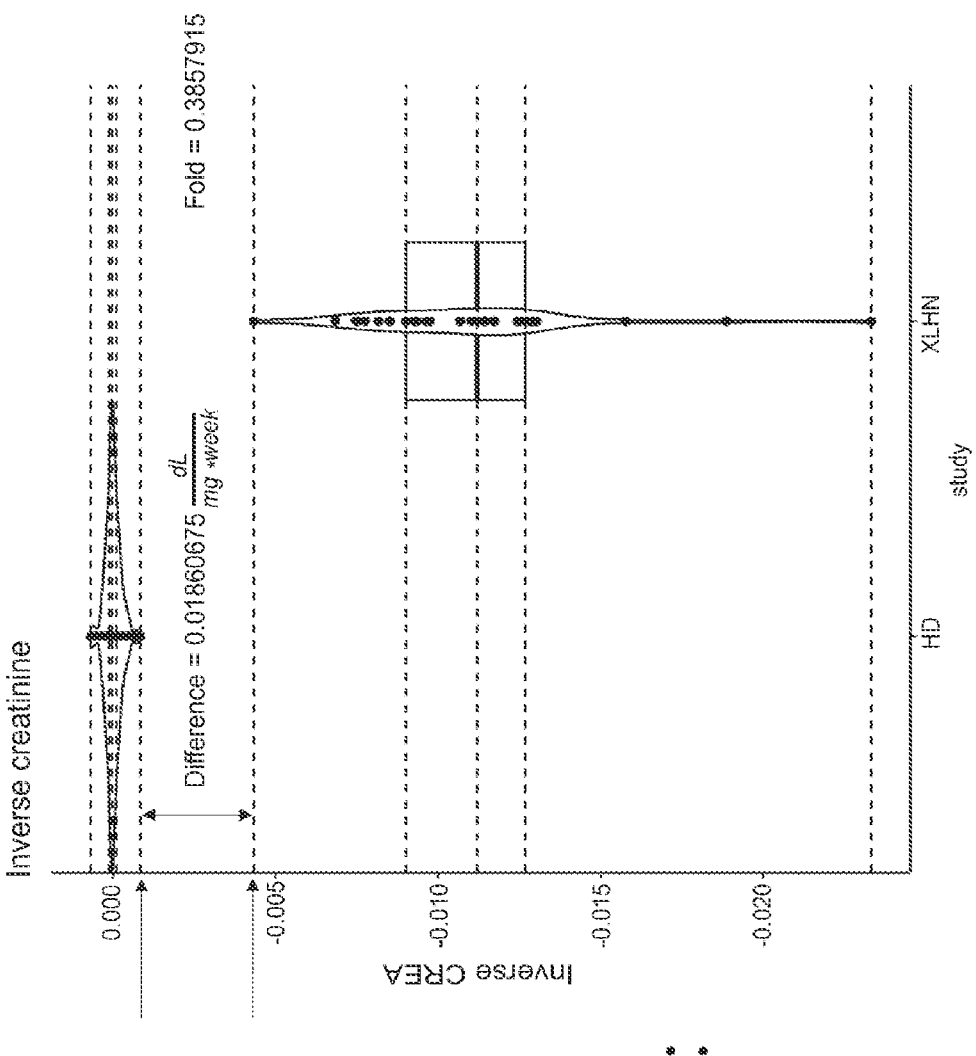
FIG. 13 shows how minimum change in inverse creatinine slope from normal to abnormal is determined.
Figure 14:
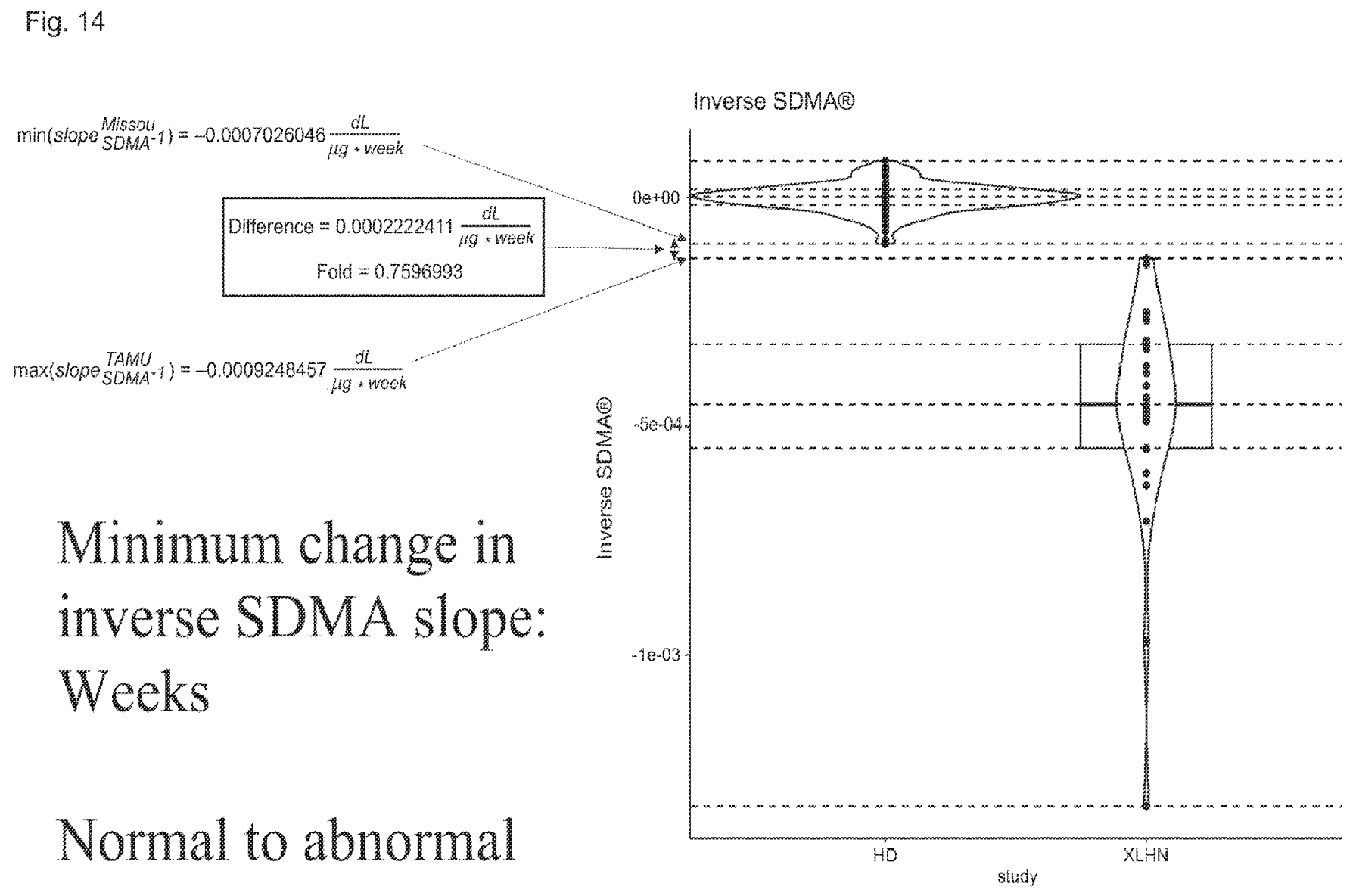

In contrast, a CKD patient with progressive CKD will exhibit a decrease of about 0.0002222411 (µg/dL)$^{-1}$/week or more (e.g. about 0.0001, 0.00015, 0.0002, 0.00025 or more) in inverse SDMA (1/SDMA) slope (FIG. 14) or a decrease of about 0.01860675 (mg/dL)$^{-1}$/week or more (e.g., about 0.010, 0.015, 0.018, 0.020, 0.025 or more) in inverse creatinine (1/creatinine) slope (FIG. 13) over time (e.g., over 1 week, 2 weeks, 3 weeks, 1, 2, 3, 4, 5, 6, 7, 8, 9, 10, 11, 12, 18, 24, 36, months or more; and any range between about 5 days and about 36 months, e.g. about 1 to about 3, about 2 to about 4, about 3 to about 6, about 6 to about 12, or about 1-36 months).

The stable versus progressive slope cutoff can be about −0.0117 (mg/dL)$^{-1}$/week (e.g., about −0.010, −0.012, −0.015, or −0.02 (mg/dL)$^{-1}$/week) for 1/creatinine and about −0.0007 (µg/dL)$^{-1}$/week (e.g., about −0.0005, −0.0006, −0.0007, or −0.0008 (µg/dL)$^{-1}$/week) for 1/SDMA.

Therefore, provided herein are methods for differentiating stable chronic kidney disease ("CKD") from progressive CKD in a subject diagnosed with CKD by:

(a) determining an inverse SDMA (1/SDMA) slope in a sample from the subject at two or more time points (e.g., at a first time point and then 1 week later, 2 weeks later, 3 weeks later, 4 weeks later or more);

(b) comparing the inverse SDMA (1/SDMA) slopes in the samples to each other, wherein a decrease of about 0.0002222411 (µg/dL)$^{-1}$/week or more over time (e.g., about 0.0001, 0.00015, 0.0002, 0.00025 (µg/dL)$^{-1}$/week or more) is an indication of progressive CKD.

The subject can be, prior to step (a), diagnosed with International Renal Interest Society CKD Stage I or CKD with a symmetric dimethyl-arginine (SDMA) value of up to 20 μg/dl. One or more treatments for CKD disease can be administered to the subject.

The methods for differentiating stable chronic kidney disease ("CKD") from progressive CKD in a subject diagnosed with CKD can comprise:

(a) measuring a concentration of SDMA in samples obtained from a subject at three or more time points (e.g., at a first time point and then 1 week later, 2 weeks later, 3 weeks later, 4 weeks later or more);

(b) determining an inverse SDMA (1/SDMA) slope in a sample from the subject at three or more time points; and (c) comparing the inverse SDMA (1/SDMA) slope to a minimum slope of a cohort of healthy control animals, wherein the inverse SDMA (1/SDMA) slope is less than the minimum slope of the cohort of healthy control animals indicates that the subject has progressive CKD and wherein the inverse SDMA (1/SDMA) slope is greater than the minimum slope of the cohort of healthy control animals indicates that the subject has stable CKD.

The minimum slope of the cohort of healthy control animals can be about $-0.0007$ $(\mu g/dL)^{-1}$/week (e.g., about $-0.0005$, $-0.0006$, $-0.0007$, or $-0.0008$ $(\mu g/dL)^{-1}$/week) for 1/SDMA.

Also provided herein are methods for differentiating stable chronic kidney disease ("CKD") from progressive CKD in a subject diagnosed with CKD by:

(a) determining an inverse creatinine (1/creatinine) slope in a sample from the subject at two or more time points (e.g., at a first time point and then 1 week later, 2 weeks later, 3 weeks later, 4 weeks later or more);

(b) comparing the inverse creatinine (1/creatinine) slopes in the samples to each other, decrease of about 0.01860675 $(mg/dL)^{-1}$/week or more (e.g., about 0.010, 0.015, 0.018, 0.020, 0.025 $(mg/dL)^{-1}$/week or more) in inverse creatinine (1/creatinine) slope over time is an indication of progressive CKD.

The subject can be, prior to step (a), diagnosed with International Renal Interest Society CKD Stage I or CKD with a symmetric dimethyl-arginine (SDMA) value of up to 20 μg/dl. One or more treatments for CKD disease can be administered to the subject.

The methods for differentiating stable chronic kidney disease ("CKD") from progressive CKD in a subject diagnosed with CKD can comprise:

a) measuring a concentration of creatinine in samples obtained from a subject at three or more time points (e.g., at a first time point and then 1 week later, 2 weeks later, 3 weeks later, 4 weeks later or more);

b) determining an inverse creatinine (1/creatinine) slope in a sample from the subject at three or more time points; and c) comparing the inverse creatinine (1/creatinine) slope to a minimum slope of a cohort of healthy control animals, wherein the inverse creatinine (1/creatinine) slope is less than the minimum slope of the cohort of healthy control animals indicates that the subject has progressive CKD and wherein the inverse creatinine (1/creatinine) slope is greater than the minimum slope of the cohort of healthy control animals indicates that the subject has stable CKD.

The minimum slope of the cohort of healthy control animals can be about $-0.0117$ $(mg/dL)^{-1}$/week (e.g., about $-0.010$, $-0.012$, $-0.015$, or $-0.02$ $(mg/dL)^{-1}$/week) for 1/creatinine.

In some embodiments, the level of Cystatin B, clusterin, SDMA, or creatinine in a test sample is compared the level of Cystatin B or clusterin (or both) in a control sample from one or more normal control subjects. Typically, the measured control level in the control sample is then compared with the Cystatin B, clusterin, SDMA, or creatinine level measured in the test sample. Alternatively, the level of Cystatin B, clusterin, SDMA, or creatinine, polypeptides in the test sample is compared to a previously determined or predefined control level (a "control standard"). For example, the control standard for Cystatin B, clusterin, SDMA, or creatinine polypeptides can be calculated from data, such as data including the levels of Cystatin B, clusterin, SDMA, or creatinine, in control samples from a plurality of normal or healthy control subjects. The normal or healthy control subjects and the test subject under assessment can be of the same species.

In some embodiments, the level of Cystatin B, clusterin, SDMA, or creatinine polypeptides in a test sample is compared the level of Cystatin B, clusterin, SDMA, or creatinine polypeptides in a control sample from one or more control subjects, wherein the control subjects have stable CKD. Typically, the measured control level in the control sample is then compared with the Cystatin B, clusterin, SDMA, or creatinine polypeptide level measured in the test sample. Alternatively, the level of Cystatin B, clusterin, SDMA, or creatinine polypeptides in the test sample is compared to a previously determined or predefined control level (a "control standard"). For example, the control standard for Cystatin B, clusterin, SDMA, or creatinine, polypeptides can be calculated from data, such as data including the levels of Cystatin B, clusterin, SDMA, or creatinine polypeptides in control samples from a plurality of control subjects that have stable CKD. The stable CKD control subjects and the test subject under assessment can be of the same species.

Particular embodiments provide reagents and methods for identifying certain diseases or conditions in mammals, e.g., in dogs, cats, and humans. Certain embodiments provide methods for providing a diagnosis and prognosis for CKD patients. Identifying and quantifying Cystatin B polypeptides in subject samples can be an independent predictor of progressive CKD. The methods advantageously permit diagnosis and identification of progressive CKD and is not influenced or confounded by CKD patient age or body mass. Accordingly, additional embodiments are directed to using a progressive CKD diagnosis determined by the methods described herein to select appropriate therapies.

Embodiments further include methods for prognosing CKD patient health, monitoring disease progression, and/or assessing/monitoring treatment efficacy by identifying levels of specific polypeptides in a CKD patient sample. In some aspects, the methods can be performed at a single time point. In other aspects, the methods can be performed in multiple time points (e.g., about 2, 3, 4, 5, or more time points) to, for example, evaluate disease progression or treatment efficacy. In a particular embodiment, the methods may be performed at diagnosis and then at specific time points post-treatment wherein a specific therapy should result in a reduction or amelioration of disease progression.

For example, a method for monitoring disease progression can comprise:

(a) determining the amount of Cystatin B, clusterin, SDMA, or creatinine, polypeptides, or combinations thereof, in a sample from a subject diagnosed with CKD at a first time point;

(b) treating the subject for CKD with one or more of the CKD treatments described herein;

(c) determining the amount of Cystatin B, clusterin, SDMA, or creatinine, polypeptides, or combinations thereof, in a sample from the subject diagnosed with CKD at a second time point;

(d) comparing the amounts of Cystatin B, clusterin, SDMA, or creatinine, polypeptides, or combinations there at the first time point and second time point.

A lower level of Cystatin B or clusterin polypeptides, or both at the second time point indicates that the treatment is slowing the progression of the progressive or stable CKD. The slopes would become less steep in this situation. Additional treatments and time points (e.g., 3, 4, 5, 6 or more time points) can be provided for.

The methods described herein can also indicate the amount or quantity of polypeptides comprising Cystatin B, clusterin, SDMA, or creatinine, SEQ ID NOs:1-32 or fragments thereof. With many indicator reagents, such as an enzyme conjugates, the amount of polypeptide present is proportional to the signal generated. Depending upon the type of test sample, it can be diluted with a suitable buffer reagent, concentrated, or contacted with a solid phase without any manipulation. For example, urine, serum, or plasma samples that previously have been diluted, or concentrated specimens such as urine, can be used to determine the presence and/or amount of polypeptide present.

Polypeptides and assays described herein can be combined with other polypeptides or assays to detect the presence of renal disease. For example, polypeptides and assays can be combined with reagents suitable for the detection or measurement of creatinine, SDMA, or general protein levels.

Methods of Treatment

Certain embodiments provide methods for treating a disease condition in a subject. The methods comprise requesting a test providing the results of an analysis to determine the amount of Cystatin B polypeptides in a sample from the subject. Treatment is administered to the subject for the disease condition if the sample contains an elevated amount of Cystatin B or clusterin polypeptides (or both) as described herein as compared to a control sample or control standard for the disease condition.

Disease conditions include stable CKD and progressive CKD. In one embodiment, a disease condition is not cancer or renal caner.

Treatments for progressive CKD include, for example, surgery for obstructed ureters, obstructive nephroliths or uroliths, dietary management (a diet reduced in amounts of protein, phosphorous, salt, or combinations thereof), administration of enteric phosphate binders, antiproteinurics (e.g., angiotensin-converting enzyme inhibitors (ACEI), administration of omega-3 fatty acids), administration of antihypertensives (e.g. ACEI, calcium channel antagonists (CCA)), fluid therapy to correct dehydration, management of acidosis, administration of diuretics, dialysis, correction of electrolyte abnormalities, administration of antiemetics, administration of antacids, and administration of recombinant erythropoietin.

Treatment using dietary management can be though a number of diets including reduced protein, reduced phosphorous, and reduced salt diets. Specialty pet food formulations are customarily recommended by veterinarians. Specialty pet food formulations include Hill's® Prescription Diet® k/d®, Royal Canin® Veterinary Diet Canine Renal Support, Purina® ProPlan® Veterinary Diet NF Kidney Function®, and Rayne Clinical Nutrition™ Adult Health-RSS™. Decreased dietary protein appears to slow the progression of CKD by decreasing the workload on the kidneys to excrete protein waste products. Less protein also means less need for the excretion of protein itself through the filtration mechanism of the kidney, which helps preserve kidney function. The recommended range of protein on a dry matter basis for dogs with CKD is less than or equal to, for example, about 14-20%. The recommended range of protein on a dry matter basis for cats with CKD is less than or equal to, for example 28-35%. Limiting dietary phosphorus in dogs and cats with CKD appears to help delay the progression of CKD, although the precise mechanism is unknown. The recommended phosphorus range on a dry matter basis for dogs with CKD is, for example, about 0.2-0.5%. The recommended phosphorus range on a dry matter basis for cats with CKD is, for example, 0.3-0.6%. Since phosphorus content is related to protein content, lower levels of phosphorus usually require limiting protein content. Dietary sodium levels are mildly restricted (about 0.3% for dogs and 0.4% for cats on a dry matter basis, for example) to reduce the workload on the kidneys. This in turn helps to maintain a reasonable blood pressure. Dietary omega-3 fatty acids help reduce the production of inflammatory compounds that create oxidative stress to the tissue of the diseased kidneys, thus contributing to slowed progression of CKD. This works by reducing protein 'leaking' through the kidneys. The recommended omega-3 fatty acids range on a dry matter basis for dogs and cats with CKD is, for example, 0.4-2.5%.

Management of acidosis can involve monitoring CKD patients for metabolic acidosis by measuring serum bicarbonate or total $CO_2$. If necessary, renal dietary therapy may be supplemented with oral sodium bicarbonate or potassium bicarbonate in order to maintain serum bicarbonate concentrations in about the 18 to 24 mmol/L range.

Correction of electrolyte abnormalities can involve correcting serum sodium concentration that may be normal, increased, or decreased with renal failure. Hypernatremia before fluid therapy indicates excessive free water loss. Administration of sodium bicarbonate or hypertonic saline may contribute to hypernatremia. Hyponatremia may indicate excessive sodium loss associated with vomiting or may represent transient dilutional hyponatremia after administration of mannitol, hypertonic dextrose, or colloid solutions. Sodium-poor solutions (e.g., about 5% dextrose, total parenteral nutrition, enteral formulations) may contribute to hyponatremia. In many situations, dehydration initially is caused by isonatremic fluid loss, and the CKD patient's serum sodium concentration is normal. The initial fluid deficit can be replaced by an isonatremic solution such as lactated Ringer's solution, 0.9% saline, or Plasmalyte-148. Continued administration of these solutions over several days may lead to hypernatremia. A sodium-poor fluid, such as half-strength lactated Ringer's solution or 0.45% saline with 2.5% dextrose, may be a more appropriate fluid choice after the initial rehydration phase. The serum sodium concentration can be monitored regularly and the fluid choice adjusted as needed. Hypokalemia can also occur but is more common in cats. Between 20% and 30% of cats with CKD have hypokalemia. Because excretion of potassium may be impaired with renal failure, treatment in this setting requires judicious supplementation with careful monitoring. In hospitalized CKD patients unable to tolerate orally administered medications, potassium chloride may be added to the IV fluids. The rate of potassium supplementation can be about 0.5 mEq/kg/h or less. Serum potassium concentration may decrease during initial fluid therapy despite supplementation because of extracellular fluid volume expansion, increased distal renal tubular flow, and cellular uptake, especially if potassium is administered with dextrose-containing fluids. Furthermore, metabolic acidosis increases the ionized calcium fraction, but more than 50% of dogs with CKD and metabolic acidosis are hypocalcemic Hypercalcemia may respond to fluid therapy. Normal saline (0.9% NaCl) is a good fluid choice because its high sodium content facilitates calciuresis. Furosemide also promotes urinary calcium loss. Sodium bicarbonate therapy decreases serum ionized calcium concentration as more calcium ions bind to serum proteins.

Holistic treatment can include, for example, administration of fish oil, B vitamins, iron, pet-friendly multivitamins, fresh parsley, kali chloricum, arsenicum album, silicea, mastica, aluminum hydroxide, or glandular therapy.

In an alternative embodiment, the methods described herein can be used to assess the efficacy of a composition or treatment regime (whether a composition or diet) for the amelioration of disease progression. Similarly, the methods described herein can be used for assessing a composition or treatment regimens activity on CKD patient levels of the clusterin or Cystatin B polypeptides.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

The Examples that follow are illustrative of specific embodiments of the disclosure, and various uses thereof. They set forth for explanatory purposes only and are not to be taken as limiting.

Example 1: Methods

Study Population

Data for control patients were pulled from an archived longitudinal study of common vector-borne diseases in pets of students, faculty and staff from the University Health Center at the University of Missouri. All pets were enrolled with owner consent, and Institutional Animal Care and Use Committee approval for the study was obtained through University of Missouri. Dogs were between one and ten years of age and were owner-reported as healthy at time of enrollment. The follow-up period was three years. The frequency of evaluation ranged from every four to six months. Patients with data available for at least three visits were included in the current study.

Since CysB is present not only in the urinary system and because it is a small 11 kD solute that could be freely filtered in the glomerulus when detectable in the circulation, it cannot be excluded that in some dogs the origin of uCysB may be from active cellular injury elsewhere in the body rather than from renal tubular epithelial cell injury. To decrease this chance, dogs with concurrent inflammatory conditions or concurrent systemic diseases that might have contributed to active cellular damage in other organs were not included in this study, further decreasing the likelihood that the origin of uCysB in this study is from extrarenal cellular damage.

Data for Stage 1 CKD dogs were collected prospectively from four additional academic institutions: University of Minnesota, North Carolina State University, Hebrew University, and University of California Veterinary Medical Center, San Diego. Dogs greater than 6 months of age presenting for evaluation of IRIS stage 1 CKD were eligible for inclusion. Owners of all patients were provided with information regarding the goals, protocol and responsibilities for the study. Owner consent was required for enrolment, and Institutional Animal Care and Use Committee approval for the study was obtained through each academic institution, respectively. Dogs with primary adrenal or pancreatic exocrine diseases, concurrent hepatic or cardiac diseases or other systemic diseases expected to promote progression of CKD were excluded. Evaluation of enrolled dogs included physical examination, CBC, comprehensive biochemical profile, urinalysis, urine culture, and UPC ratio. Each dog was reassessed and IRIS CKD staged at monthly intervals for six months.

Stage 1 Stable Vs. Progressive CKD Classification

Classification of Stage 1 IRIS CKD patients into stable or progressive CKD was based on the slopes calculated from linear regressions with inverse SDMA as the dependent variable and follow-up time as the independent variable for each patient. A slope cutoff of $-0.0007$ $(\mu g/dL)^{-1}$/week was used. Patients with slopes greater than or equal to the cutoff were classified as stable CKD. Patients with slopes less than the cutoff were classified as progressive CKD.

uCysB Technique uCysB was measured using a research sandwich-format ELISA at IDEXX Headquarters (Westbrook, ME) as previously described. Urine sample aliquots for uCysB measurement were frozen at $-80°$ C., shipped frozen in batches to IDEXX, and stored at $-80°$ C. until testing in batch as the study progressed.

Descriptive Analysis

Descriptive analyses were performed to understand the relationships between serial uCysB values within dogs and their CKD status (control, stable, progressive). This also provided insight into the dependence of serial samples of each dog as well as the effect of CKD group on uCysB values. Kruskal-Wallis ANOVAs were used to provide insight into whether differences existed in uCysB expression of dogs within a CKD group as well as between CKD groups. Least square regressions between uCysB (dependent) and follow-up day (independent) were performed for each dog to understand the effect of CKD group on y-intercepts and slopes. Post-hoc descriptive analyses were conducted to understand the potential utility of uCysB as an early biomarker of progressive CKD.

Statistical Analysis

A linear mixed-effects model with random slope and coefficient was used to assess the relationship between follow-up time and uCysB. A random intercept was used to account for the non-independence of serial uCysB measurements within each individual. A random coefficient was used to account for non-independence within each CKD group. An unstructured covariance structure was used to allow for unique variation patterns for each individual. Plots of the regressions lines and standard error bars for each CKD group were produced based on predicted uCysB values for each day of follow-up (day 0 to day 851). All statistical analyses were performed in R (version 4.1.0).

Example 2. Demographics

Demographics of enrolled dogs are provided in 3. There were 55 (73%) controls, 12 (16%) stable CKD dogs and 8 (11%) progressive CKD dogs. Over half (56%; 42/75) of the enrolled dogs were between five and ten years of age. Most dogs were spayed females or castrated males. The top five breeds are listed in 3.

TABLE 3

| Demographic | Control (n = 55) (73%) | Stable CKD (n = 12) (16%) | Progressive CKD (n = 8) (11%) |
|---|---|---|---|
| Age (years) | | | |
| <1 year old (n = 1) (1%) | 0 (0) | 1 (8) | 0 (0) |
| 1 to <5 years old (n = 23) (31%) | 16 (29) | 5 (42) | 2 (25) |
| 5 to <10 years old (n = 42) (56%) | 36 (65) | 5 (42) | 1 (12) |
| At least 10 years old (n = 9) (12%) | 3 (5) | 1 (8) | 5 (62) |
| Sex | | | |
| Female (n = 2 3%) | 1 (2) | 1 (8) | 0 (0) |
| Spayed female (n = 36) (48%) | 27 (49) | 5 (42) | 4 (50) |
| Male (n = 1) (1%) | 1 (2) | 0 (0) | 0 (0) |
| Castrated male (n = 34) (45%) | 26 (47) | 5 (42) | 3 (38) |
| Unknown (n = 2) (3%) | 0 (0) | 1 (8) | 1 (12) |
| Breed | | | |
| Mixed (n = 20) (27%) | 16 (29) | 1 (8) | 3 (38) |
| Labrador retriever (n = 8) (11%) | 4 (7) | 2 (17) | 2 (25) |
| Dachshund (n = 6) (8%) | 6 (11) | 0 (0) | 0 (0) |
| Golden retriever (n = 6) (8%) | 3 (5) | 3 (25) | 0 (0) |
| German shorthaired pointer (n = 3) (4%) | 2 (4) | 1 (8) | 0 (0) |
| Other (n = 32) (43%) | 24 (44) | 5 (42) | 3 (38) |

Example 3. Descriptive Analysis

Figure 2:
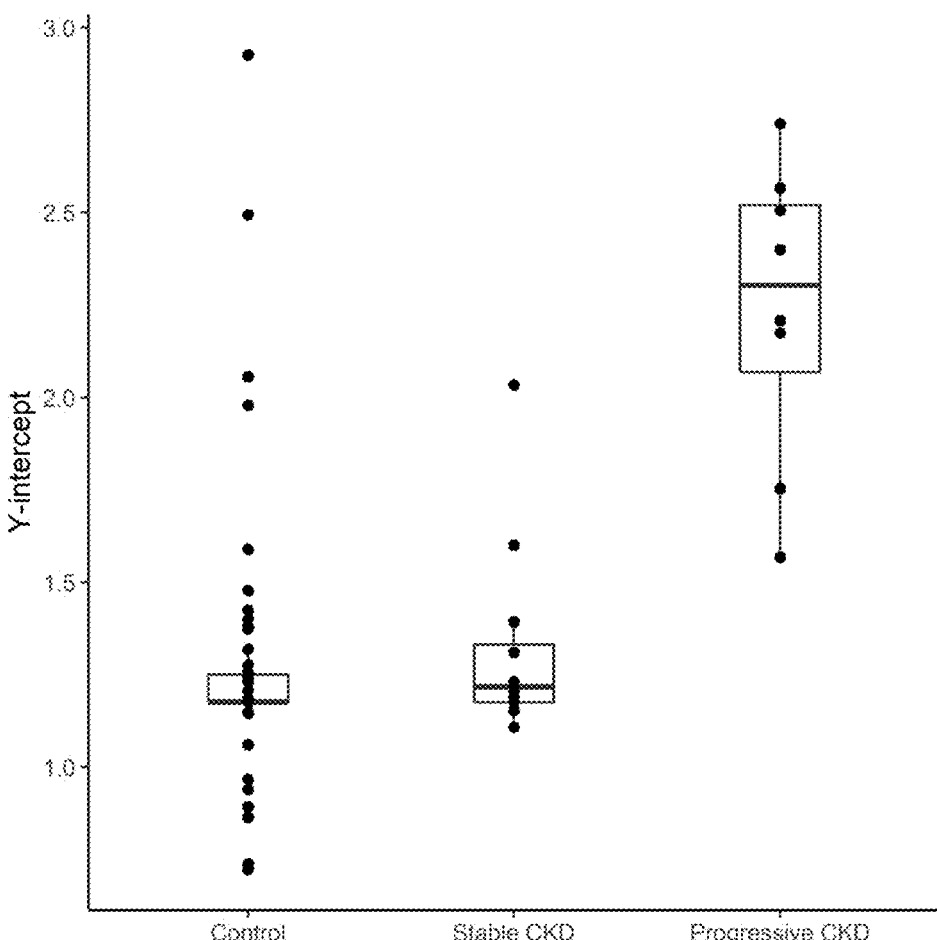
FIG. 2 shows Y-intercepts calculated from per-dog linear regression with urinary cystatin B as the dependent variable and follow-up time as the independent variable. While the y-intercepts for control dogs and stable CKD dogs were relatively comparable, the y-intercepts for progressive CKD dogs were consistently higher. Differences in y-intercepts between groups were detected with Kruskal-Wallis ANOVA ($p<10^{-4}$).
Figure 3:
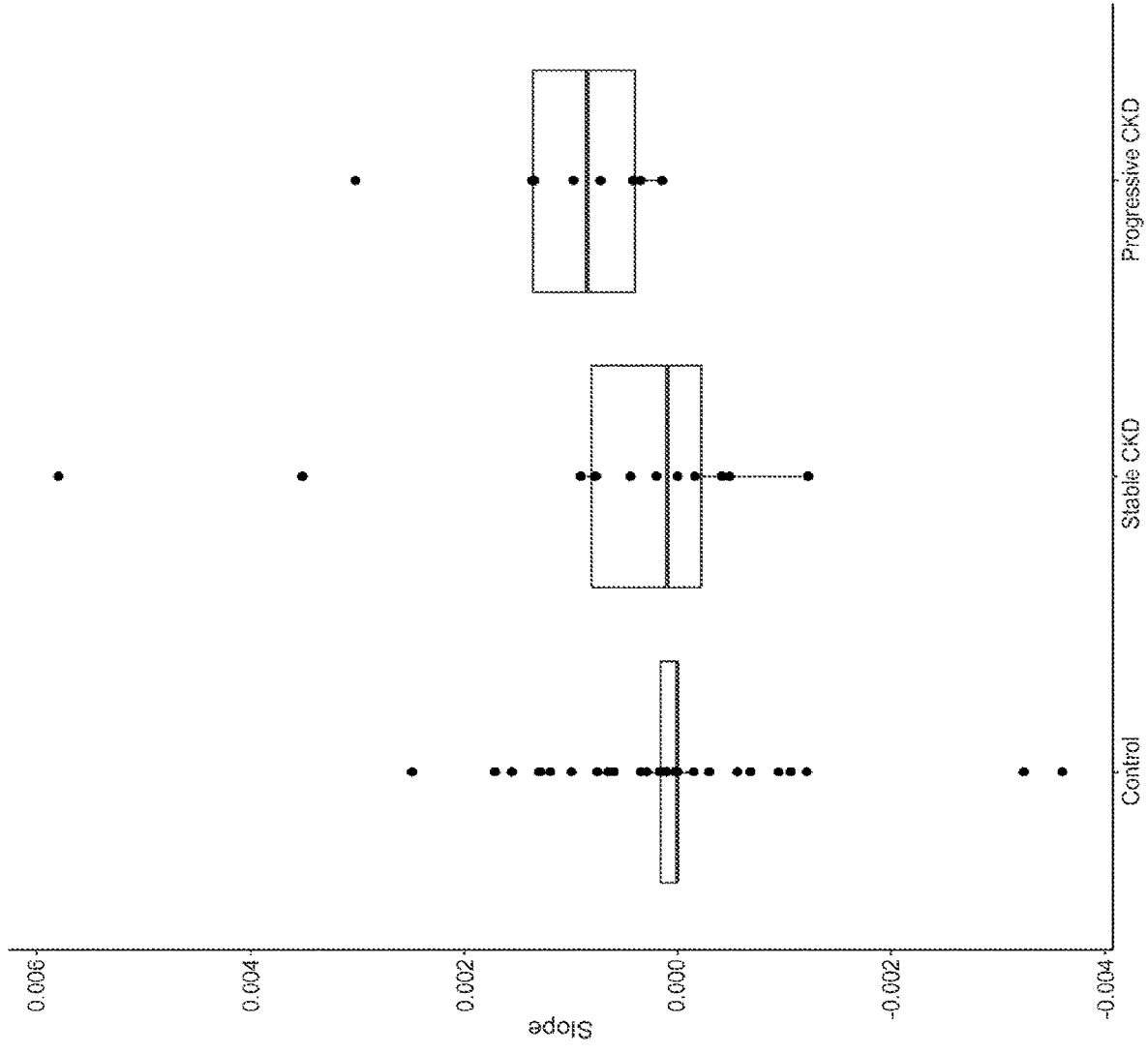
FIG. 3 shows slopes calculated from per dog linear regression with log(uCysB) as the dependent variable and follow-up time as the independent variable. Difference between slopes of control, stable CKD and progressive CKD dogs was detected on Kruskal-Wallis ANOVA (p=0.006).
Figure 4:
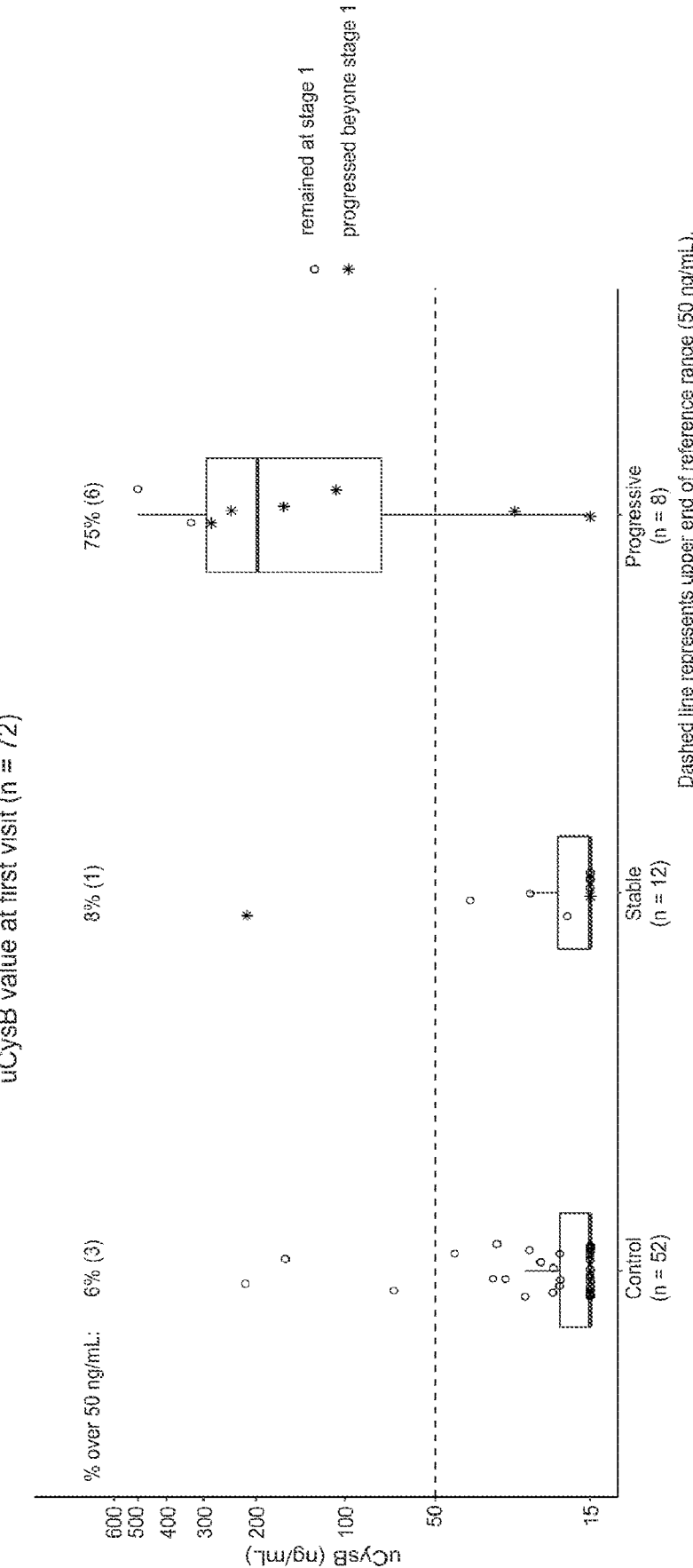
FIG. 4 shows first uCysB measurements by CKD group. Although only eight dogs had progressive IRIS stage 1 CKD at first visit, six (75%) had first uCysB values over the reference range (RR) of 50, four (67%) of which progressed beyond IRIS stage 1 CKD.

Differences in log(uCysB) expression existed among dogs of the same study group ($p_{control}$<0.02; $p_{stable}$<$10^{-7}$; $p_{progressive}$<$10^{-6}$) (FIG. 1). Log(uCysB) values of progressive CKD dogs appeared to be higher than those of control and stable CKD dogs. Y-intercepts calculated based on per-dog linear regressions also differed by CKD group ($p<10^{-4}$) (FIG. 2). The y-intercepts of progressive CKD dogs tended to be higher than those of the control dogs and stable CKD dogs. A difference (p=0.006) (FIG. 3) in slopes between control, stable CKD and progressive CKD dogs was detected. Post-hoc analysis (FIG. 4) showed that 75% (6/8) of dogs with progressive CKD had elevated uCysB values at first visit. In contrast, only six (3/52) and eight (1/12) percent of control and stable dogs had elevated uCysB values at first visit.

The results of the linear mixed effects model are shown in Table 4.

TABLE 4

Results of linear mixed effects model. A random intercept was used to account for the non-independence of repeated measures within an individual. Urinary cystatin B was the dependent variable. Follow-up day was the independent variable. The effect of CKD group was allowed to vary randomly.

| Fixed effects | Coefficient | 95% CI | Random effect (SD) |
|---|---|---|---|
| Follow-up day | 0.00041 | 0.00011-0.00041 | — |
| CKD group | | | |
| Control | — | — | — |

35

TABLE 4-continued

Results of linear mixed effects model. A random intercept
was used to account for the non-independence of repeated
measures within an individual. Urinary cystatin B was the
dependent variable. Follow-up day was the independent variable.
The effect of CKD group was allowed to vary randomly.

| Fixed effects | Coefficient | 95% CI | Random effect (SD) |
|---|---|---|---|
| Stable | 0.33 | −0.022-0.33 | 0.54 |
| Progressive | 2.53 | 1.95-2.53 | 0.79 |

Figure 5:
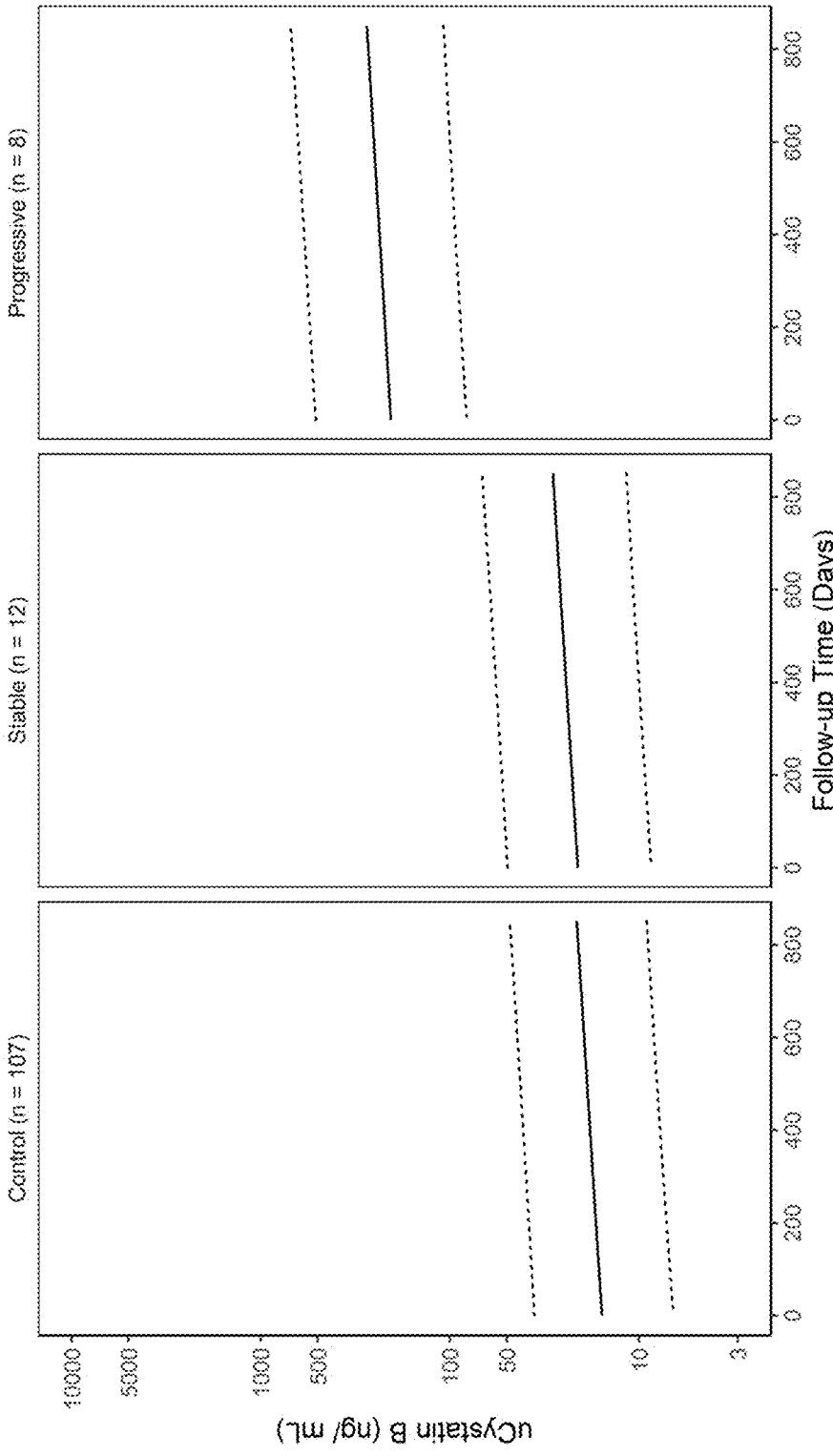
FIG. 5 shows the differentiation of stable CKD from progressive CKD using cystatin B levels in canine International Renal Interest Society Stage I CKD patients.

Progressive CKD dogs have significantly higher uCysB values than stable CKD and control dogs. A plot of the linear mixed effects model is shown in FIG. 5.

Example 4: Cystatin B and Clusterin Differentiation

Urinary cystatin B (uCysB), a novel kidney injury biomarker, has potential to predict progression of early CKD.

Early identification of dogs with progressive versus stable chronic kidney disease (CKD) might afford opportunity for interventions that would slow progression. However, currently there is no surrogate biomarker to reliably predict CKD progression. A high urinary Cystatin B ("uCystatin B" or "uCysB") level in a canine patient not diagnosed with CKD could be indicative of acute kidney injury (AKI). Thus, Cystatin B and clusterin differentiation of stable versus progressive CKD was studied in patients with diagnosed CKD.

Animals: 20 dogs presenting for evaluation of International Renal Interest Society Stage (IRIS) I CKD (Stage I), with IDEXX SDMA® up to 17 μg/dL and no systemic comorbidities, and 107 clinically healthy dogs (controls).

Methods: A prospective longitudinal study was conducted between 2016 and 2021 to assess the pattern of expression of uCysB in Stage I CKD and control dogs. Dogs were followed to a maximum of 3 years. Stage I was subgrouped as stable or progressive CKD by 1/IDEXX SDMA® slope, calculated from a minimum of three monthly timepoints during the initial 120-day period. Dogs with slope above or below −0.0007 (μg/dL)$^{-1}$/week were classified as stable or progressive, respectively. Mixed effects modeling was used to assess the association between uCysB and progression rate.

Results: Estimated uCysB was 16 ng/mL for control, 23 ng/mL for stable CKD, and 204 ng/mL for progressive CKD predicting active ongoing injury (FIG. 5, p<0.05, dashed lines represent 95% confidence intervals). Thus, uCysB differentiated stable versus progressive Stage I CKD. Early discrimination of dogs with progressive CKD creates an opportunity for interventions to arrest progression and improve patient management.

The levels of Cystatin B and clusterin were determined by ELISA in the urine of the canine patients. The minimum inverse SDMA slope observed in the population of healthy canines over a maximum period of three years was −0.0007 (μg/dL)$^{-1}$/week, and this was assigned as the slope cutoff for stable kidney function. Minimum slope refers to the slope of the individual dog with the most negative slope. In other words, the minimum slope is the slope with the lowest numerical value. As mentioned above, in the group of patients with diagnosed CKD, patients with slope above or below −0.0007 (μg/dL)$^{-1}$/week were classified as stable or progressive, respectively.

Mixed effects modeling was also used to assess the association between clusterin and progression rate. The IRIS stage I subgroup analysis included CKD patients with an initial SDMA up to 17. Findings of the study were then found to hold true up to an initial SDMA of up to 20, which extends into the early phase of IRIS stage II. In other words, Cystatin B can differentiate stable vs. progressive disease in CKD patients with SDMA values up to 20, which covers stage I (<18 μg/dl) and part of stage II (18-35 μg/dl).

Figure 6:
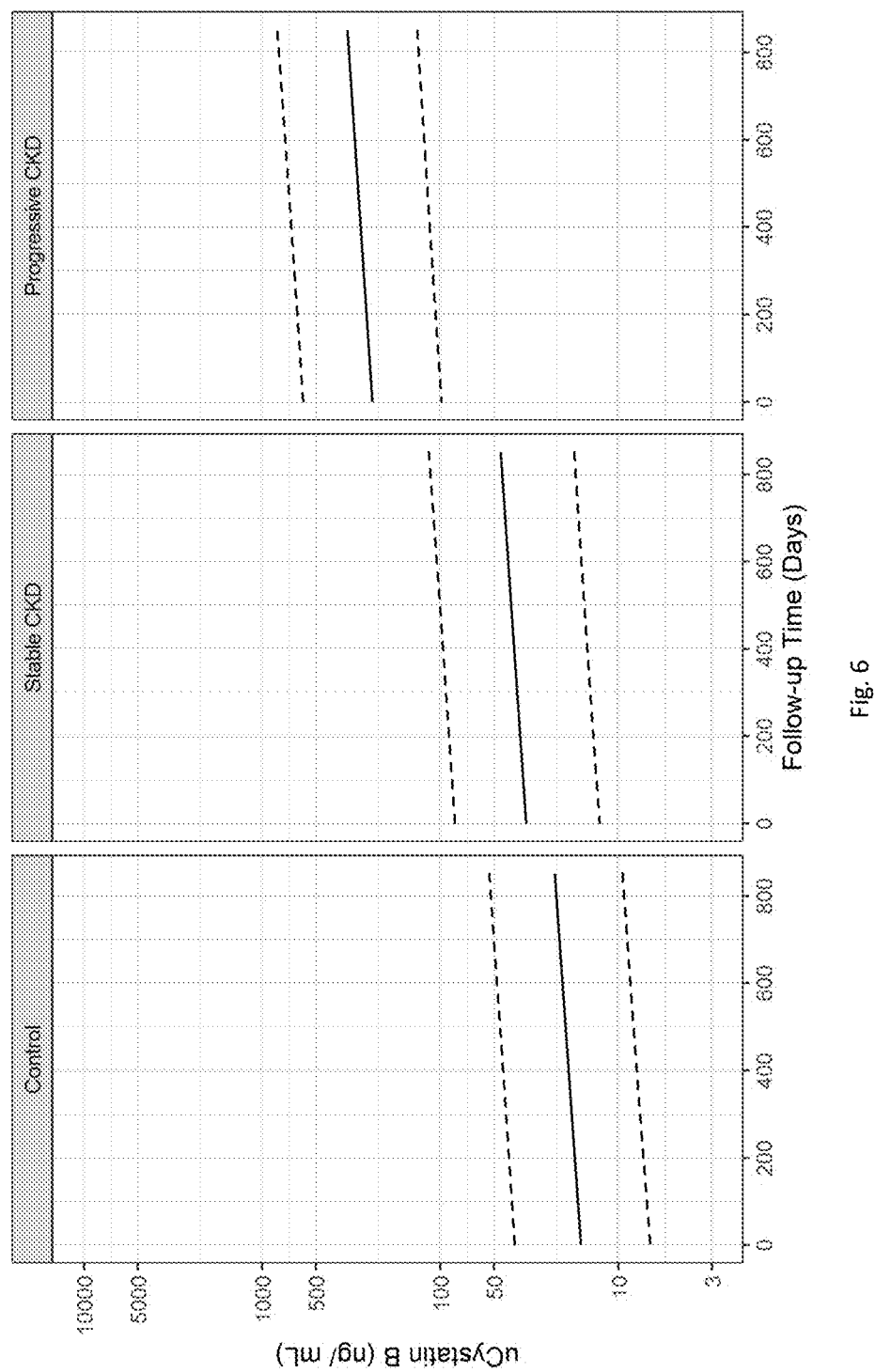
FIG. 6 shows the differentiation of stable CKD from progressive CKD using cystatin B levels in canine CKD patients with SDMA values up to 20.

Cystatin B differentiates stable from progressive CKD in International Renal Interest Society Stage I CKD patients as shown in FIG. 5. Cystatin B differentiates stable from progressive CKD in patients with SDMA values up to 20 as shown in FIG. 6.

Figure 7:
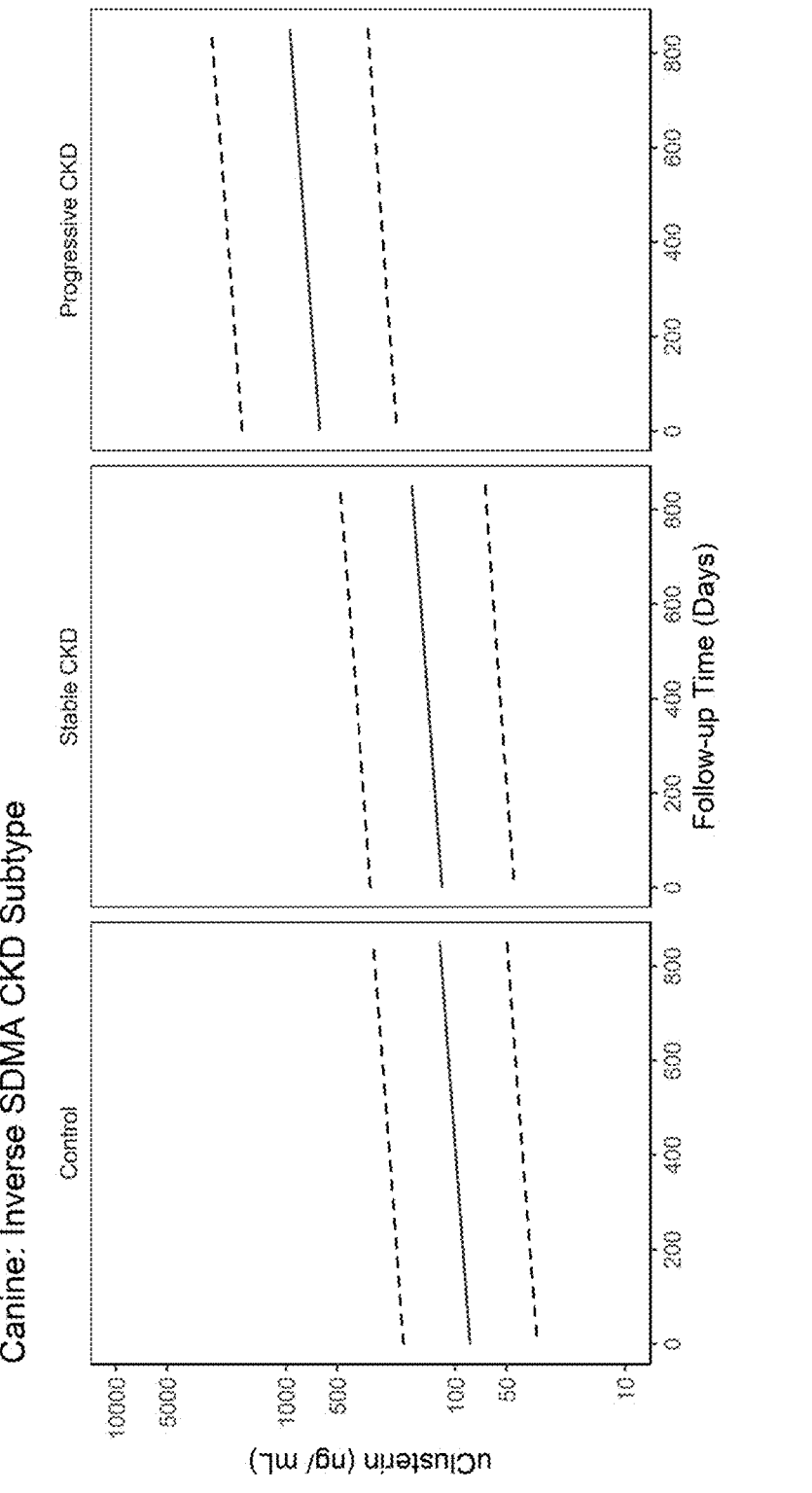
FIG. 7 shows the differentiation of stable CKD from progressive CKD using clusterin levels in canine International Renal Interest Society Stage I CKD patients.

Clusterin differentiates stable from progressive CKD in International Renal Interest Society Stage I CKD patients as shown in FIG. 7.

Figure 8:
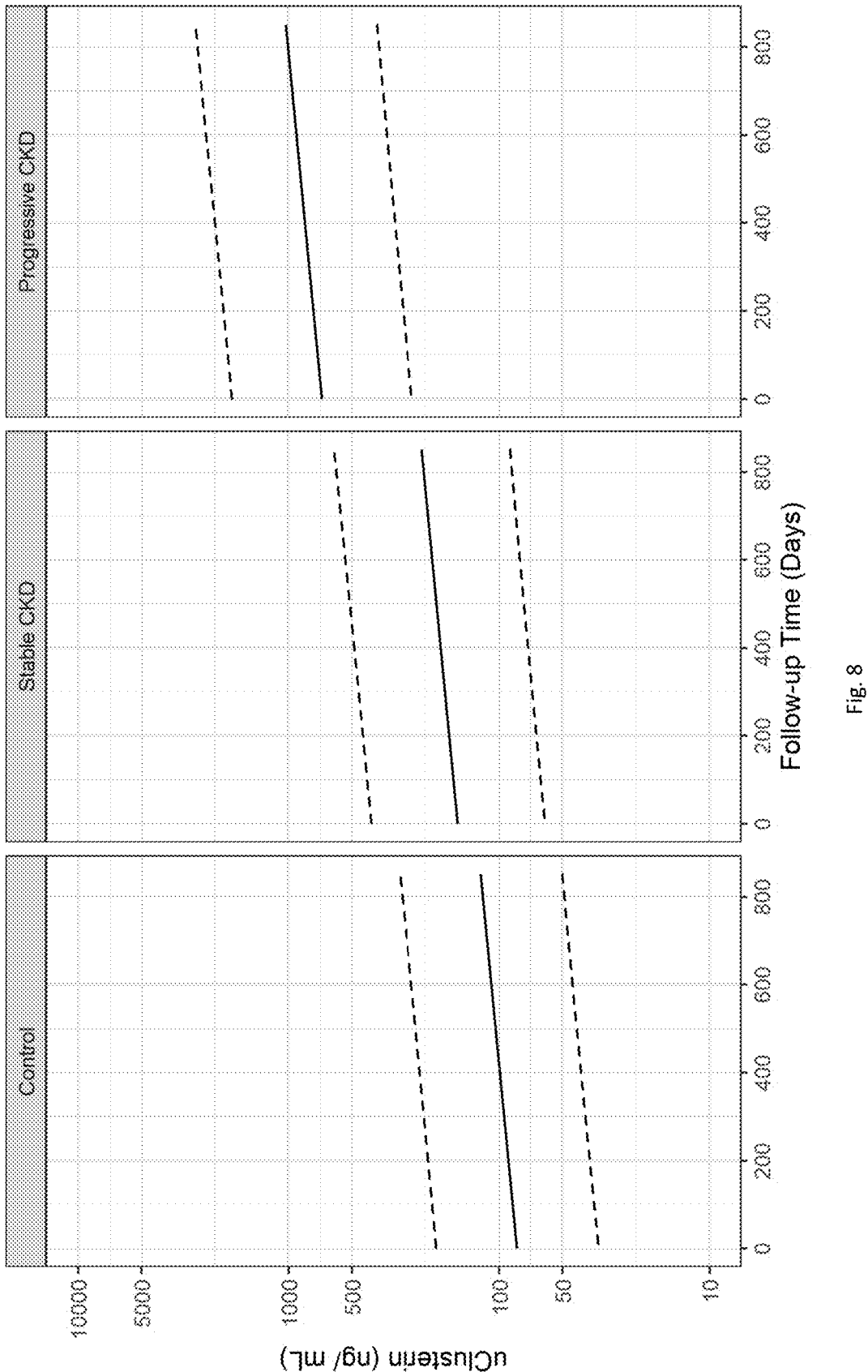
FIG. 8 shows the differentiation of stable CKD from progressive CKD using clusterin levels in canine CKD patients with SDMA values up to 20.

Clusterin differentiates stable from progressive CKD in patients with SDMA values up to 20 as shown in FIG. 8).

Example 5: Differentiation of Stable Kidney Function Versus Progressive Dysfunction in Dogs Markers of kidney function have been used variably to define stable versus progressive chronic kidney disease (CKD), but quantitative criteria to distinguish these populations are lacking. Here, 1/creatinine and 1/IDEXX SDMA® slope cutoffs were assessed to distinguish stable versus progressive CKD.

Animals: 113 clinically healthy dogs and 29 male colony dogs with progressive X-linked hereditary nephropathy (XLHN). Healthy Dogs Cohort (HD) had archived samples from dogs enrolled in a prospective study assessing the serologic status of clinically healthy dogs for Lyme, *Ehrlichia*, and *Anaplasma*. The HD cohort was made up of student- or staff-owned dogs between 1 and 10 years of age at the University of Missouri. Health status assessed at each sample collection by clinical history, CBC, serum chemistry profile, urinalysis, and serology. Both seropositive and seronegative healthy dogs were included and sampled every 4-6 months for >2 years. XLHN cohort had archived samples from dogs enrolled in a prospective study assessing the progressive profile of XLHN. XLHN is a rapidly progressive glomerulopathy caused by genetic mutation of the α5 chain of type IV collagen. Intact male puppies (homozygous affected) from a single family of purpose-bred colony dogs maintained at Texas A&M University. Blood samples were obtained monthly until succumbing to CKD.

Analyses: archived serum samples were stored at −80° C. from 2012-2014 for the HD (clinically healthy dogs) cohort and 2002-2012 for the XLHN cohort. Functional marker sCreatinine was analyzed by modified Jaffe method at IDEXX Columbus, OH (HD) and by enzymatic method at Texas A&M (XLHN). Functional marker sSDMA was analyzed by LC-MS (IDEXX Westbrook, ME).

TABLE 5

Characteristics of HD Cohort
HD (n = 113)

| Age | n (%) |
|---|---|
| ≤15 weeks | 3 (3%) |
| 15 weeks-1 year | 6 (5%) |
| 1-5 years | 60 (53%) |
| 5-10 years | 42 (37%) |
| >10 years | 2 (2%) |

TABLE 5-continued

| Characteristics of HD Cohort HD (n = 113) | |
| --- | --- |
| Weight | <5 kg to >35 kg |
| Sex | n (%) |
| F | 12 (11%) |
| FS | 47 (42%) |
| M | 9 (8%) |
| MC | 45 (40%) |

TABLE 6

| Characteristics of XLHN Cohort XLHN (n = 29) | |
| --- | --- |
| Age: | Enrolled at 15 weeks of age |
| Weight: | <5 kg (at study initiation) |
| Sex: | All male homozygous for the α5 chain mutation |

Methods: Retrospective analysis combining two prospective observational studies, one tracking kidney function markers in healthy dogs (HD) to a maximum of 3 years, and one tracking kidney function markers in male colony dogs with progressive from HD was assigned as the slope cutoff for stable kidney function. Sequential 1/Creatinine and 1/SDMA transformations for each dog were plotted vs follow-up time.

Slope of the 1/Creatinine and 1/SDMA transformations (dependent variable) vs follow-up time (independent variable) for each dog was calculated using simple linear regression. The minimum slope value for HD was set as the cutoff value for stable kidney function vs progressive kidney dysfunction. Relative 1/Creatinine and 1/SDMA slopes were plotted with assigned cohort-specific intercepts for visual comparison.

Figure 9:
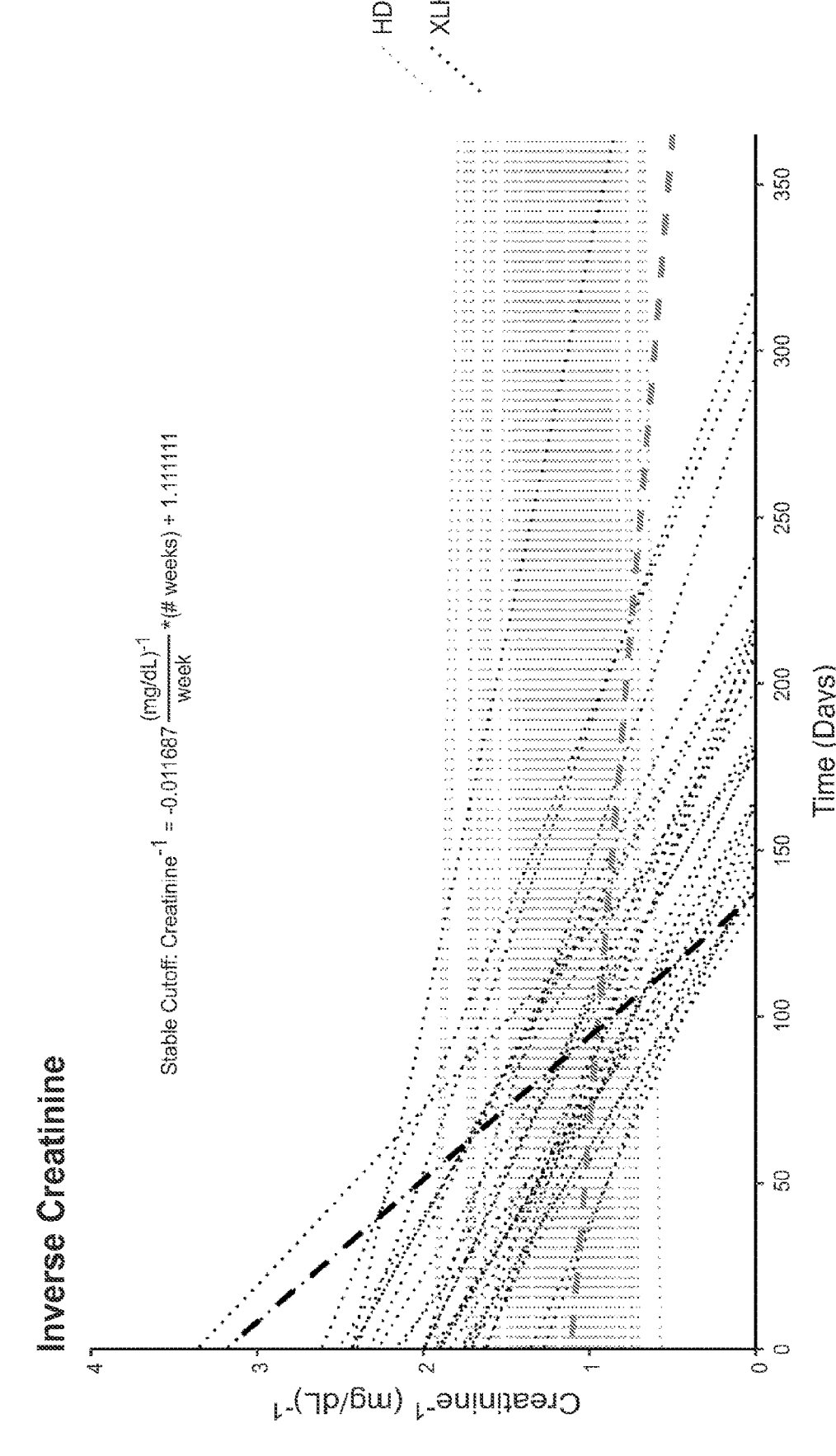
FIG. 9 shows inverse creatinine slope cutoff to distinguish stable kidney function in healthy dogs (HD) versus kidney dysfunction in progressive CKD resulting from X-linked hereditary nephropathy (XLHN). Slope cutoff shown as dashed gray line.
Figure 10:
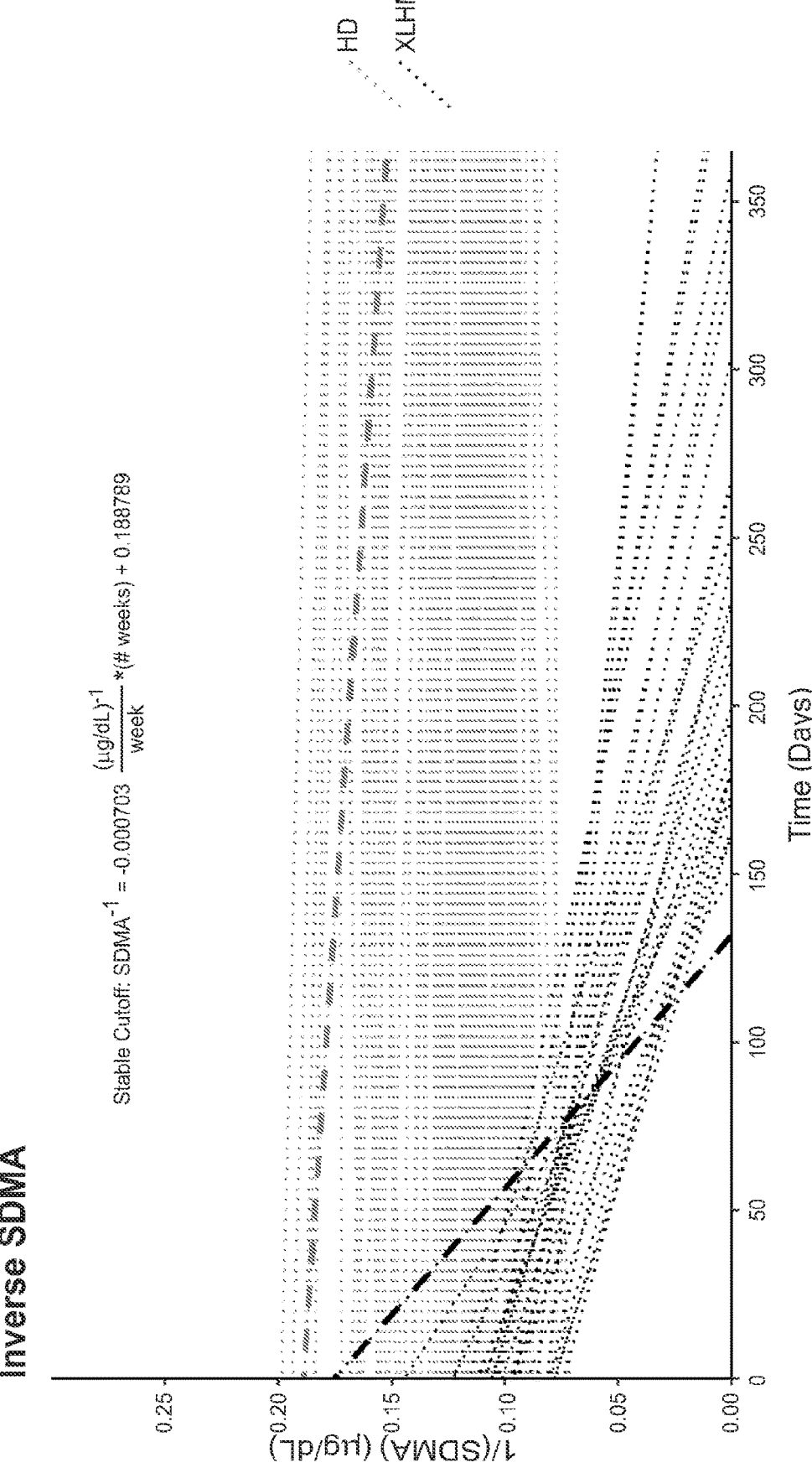
FIG. 10 shows inverse SDMA slope cutoff to distinguish stable kidney function in healthy dogs (HD) versus kidney dysfunction in progressive CKD resulting from XLHN. Slope cutoff shown as dashed gray line.

Results: The stable versus progressive slope cutoff was $-0.0117$ (mg/dL)$^{-1}$/week for 1/creatinine and $-0.0007$ (µg/dL)$^{-1}$/week for 1/IDEXX SDMA® (FIG. 9 and FIG. 10, dashed gray lines).

In the studied CKD population, progressive dysfunction can be distinguished from stable kidney function by using the slope of 1/creatinine or 1/IDEXX SDMA®. These criteria may serve to characterize CKD in other cohorts of dogs and to establish guidelines for progression rate in dogs with naturally acquired CKD.

Figure 15:
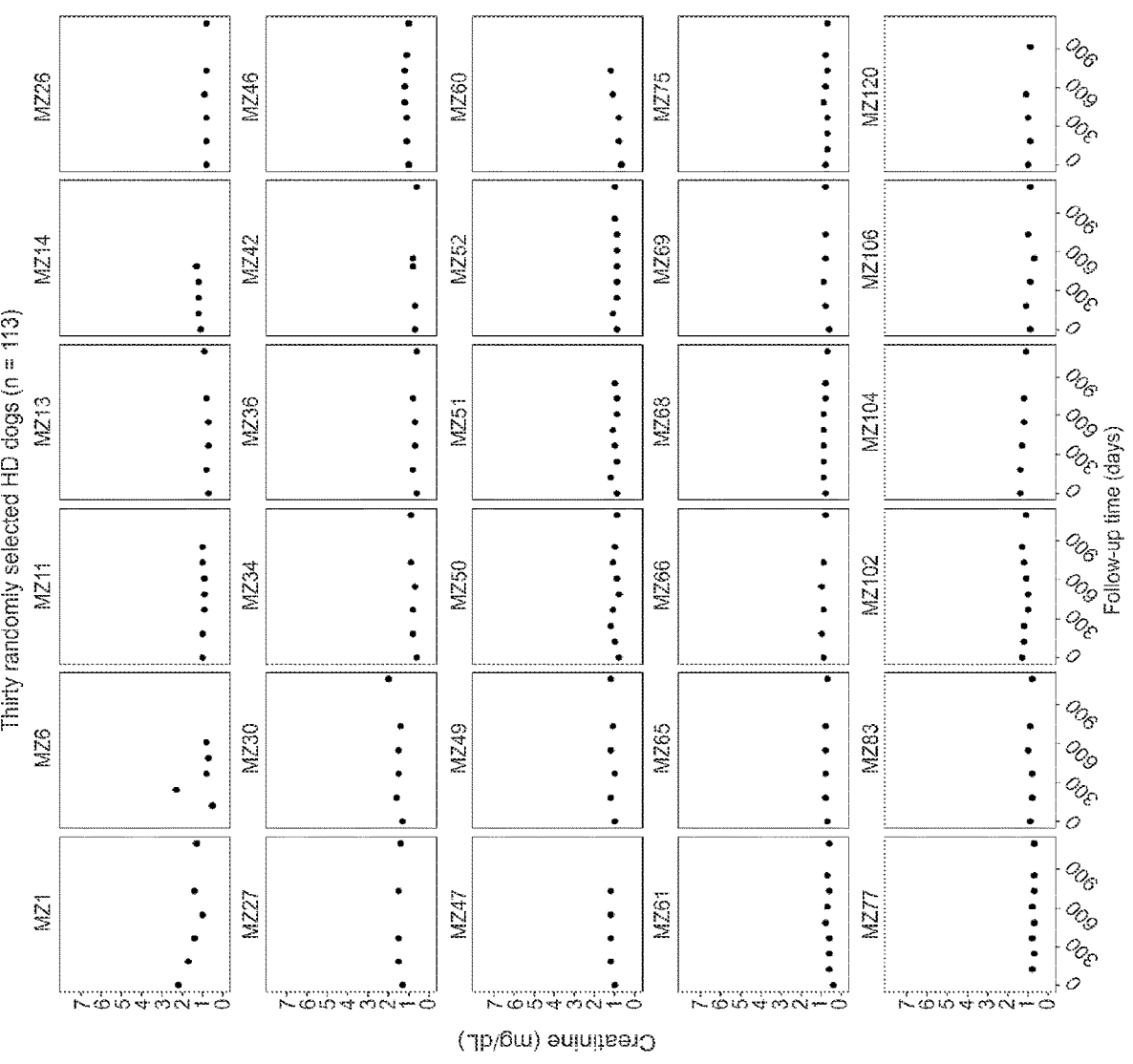
FIG. 15 shows representative serial sCreatinine observations in 30 dogs selected randomly from a cohort of 113 healthy dogs
Figure 18:
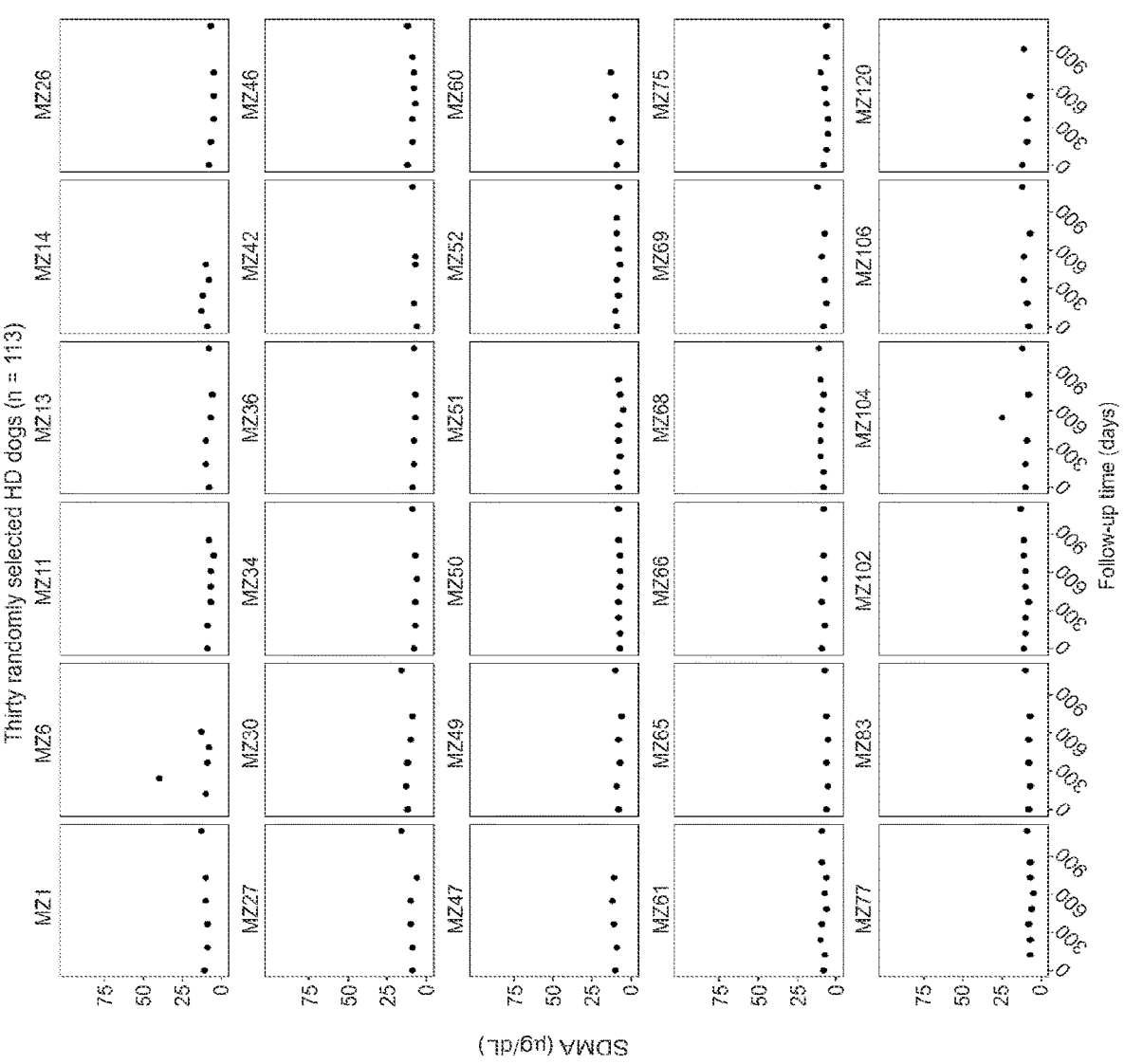
FIG. 18 shows representative serial observations in sSDMA in 30 dogs selected randomly from a cohort of 113 healthy dogs.

Functional marker sCreatinine remained stable in healthy dogs throughout >2 years of observation (Table 7 and FIG. 15). Similarly, functional marker sSDMA remained stable in health dogs over 1,096 days of observation (Table 8 and FIG. 18).

TABLE 7

| Median sCreatinine in the HD Cohort (n = 113). HD (n = 113) | |
| --- | --- |
| Start | 0.9 (IQR, 0.7-1.0) mg/dL |
| End | 0.8 (IQR, 0.7-1.0) mg/dL |
| Observation interval | 1,096 days (IQR, 1096-1096) |

TABLE 8

| Median sSDMA in HD Cohort (n = 113). HD (n = 113) | |
| --- | --- |
| Start | 9 (IQR, 8-11) µg/dL |
| End | 9 (IQR, 8-11) µg/dL |
| Observation interval | 1,096 days (IQR, 1096-1096) |

Figure 16:
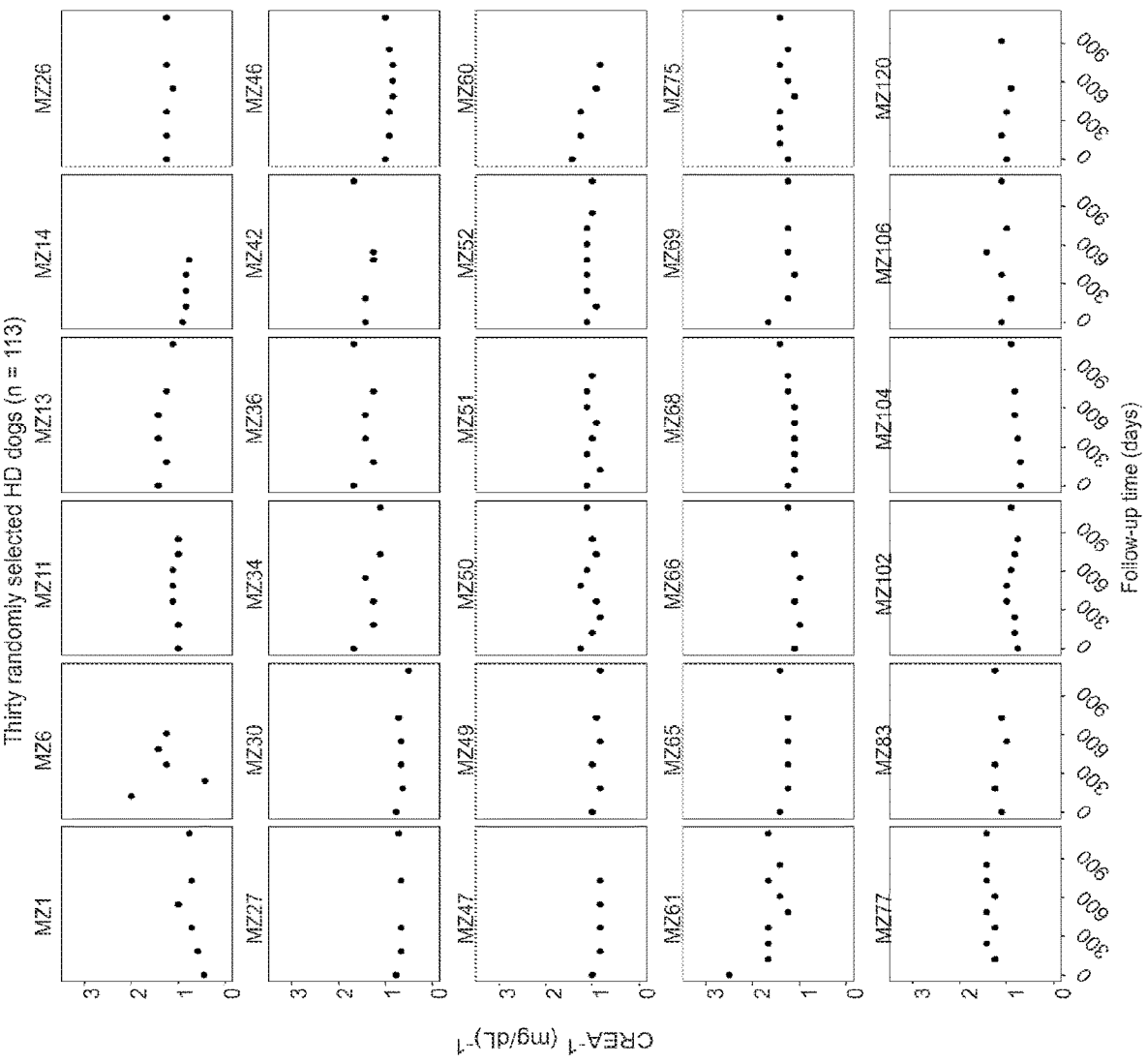
FIG. 16 shows representative serial changes in inverse creatinine in 30 dogs selected randomly from a cohort of 113 healthy dogs.
Figure 17:
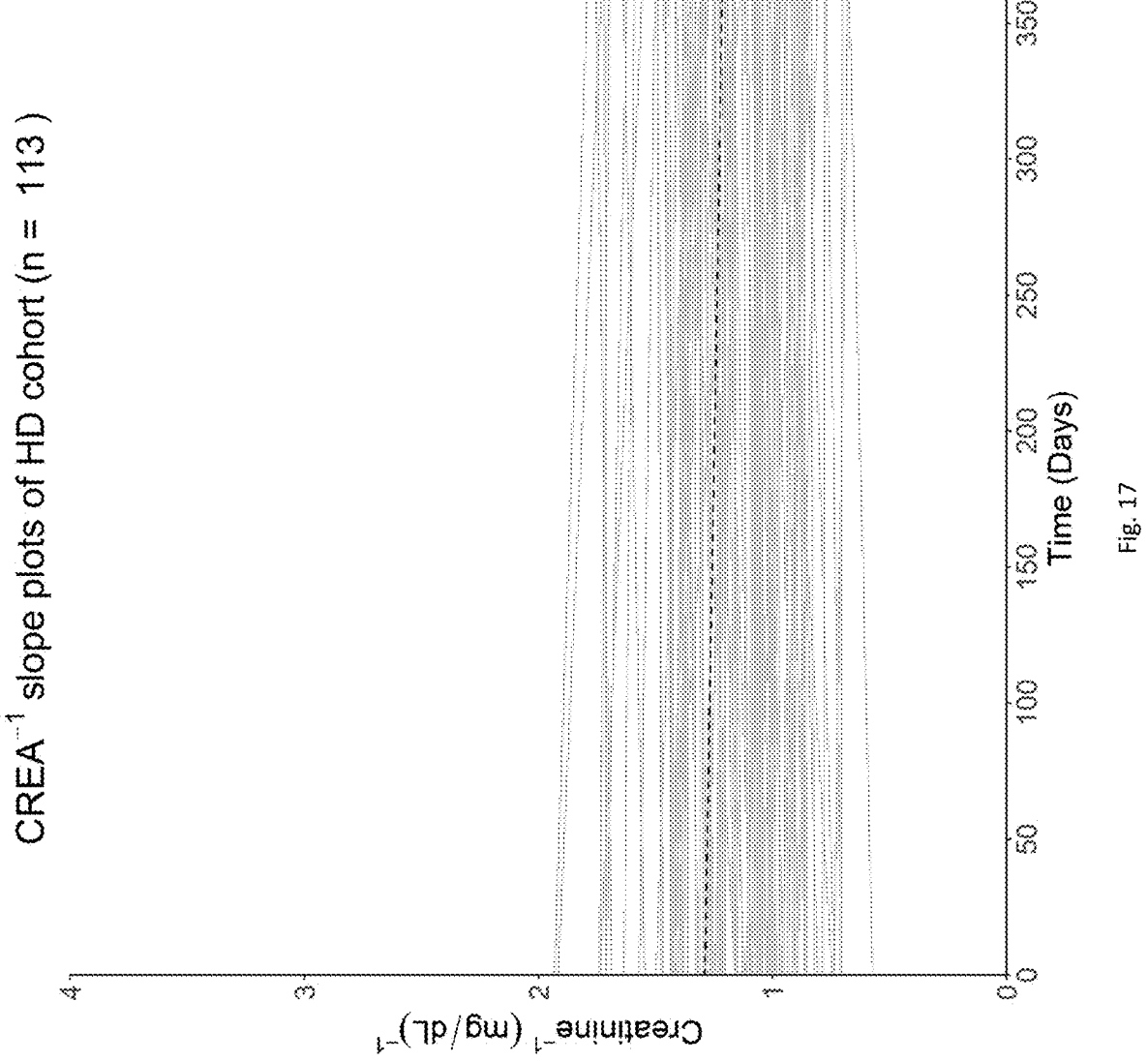
FIG. 17 shows inverse creatinine slope plots of HD Cohort.
Figure 19:
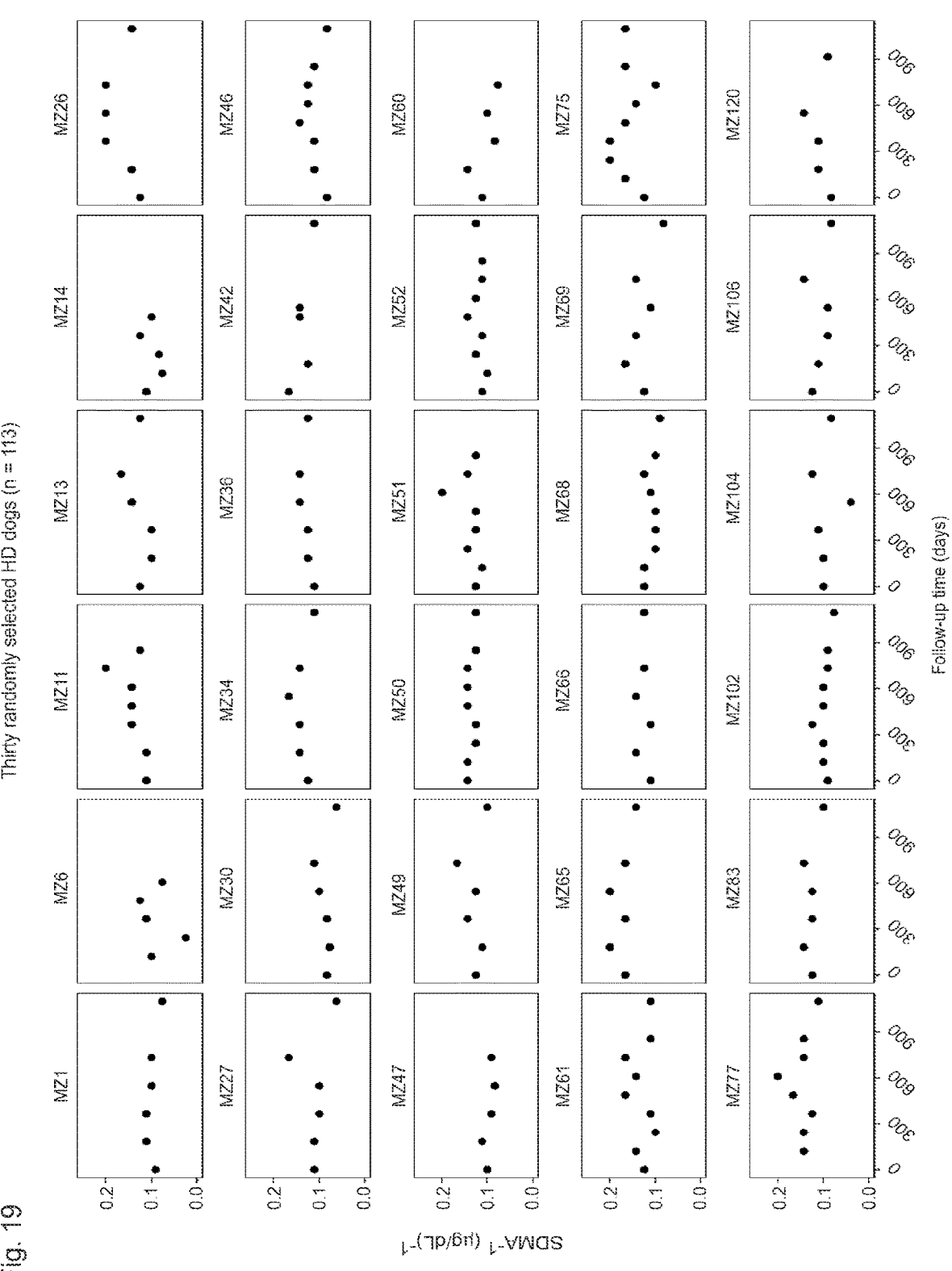
FIG. 19 shows serial changes in inverse SDMA in 30 dogs selected randomly and slopes from a cohort of 113 healthy dogs.
Figure 20:
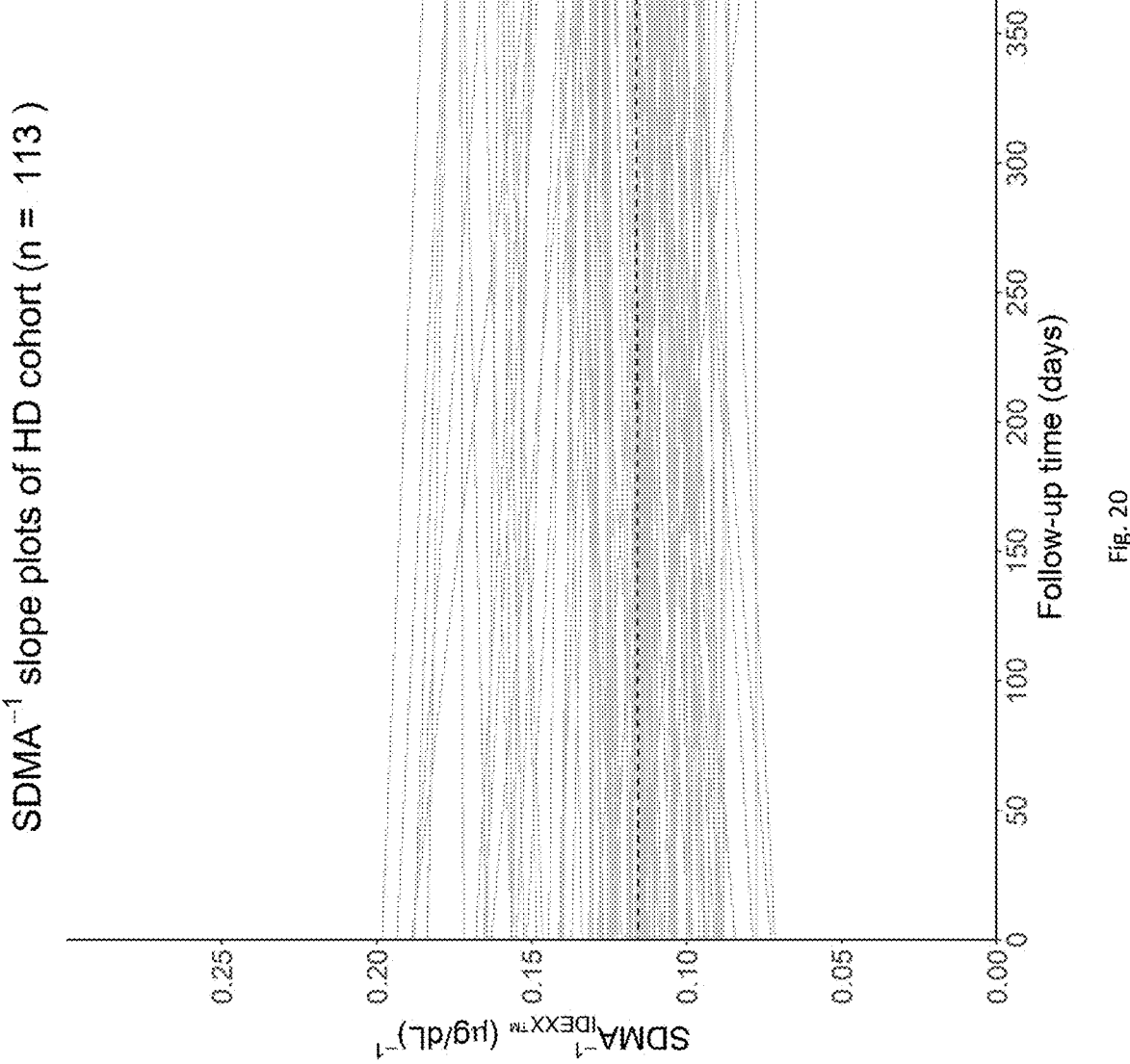
FIG. 20 shows inverse SDMA slope plots of HD Cohort.

1/creatinine remained stable in healthy dogs over time. The median slope (day) was 1/creatinine=0.00001436* [(mg/dl)–1/day]*(# days)+0.9324022. The median slope (week) was 1/creatinine=0.00010052*[(mg/dl)–1/week]*(# weeks)+0.9324022 (FIG. 16 and FIG. 17. Similarly, 1/SDMA remained stable in healthy dogs over time. The median slope (day) was 1/SDMA=0.00000175*[(µg/dl)–1/ day]*(# days)+0.1155601. The median slope (week) was 1/SDMA=0.00001225*[(µg/dl)–1/week]*(# weeks)+ 0.1155601 (FIG. 19 and FIG. 20).

Figure 21:
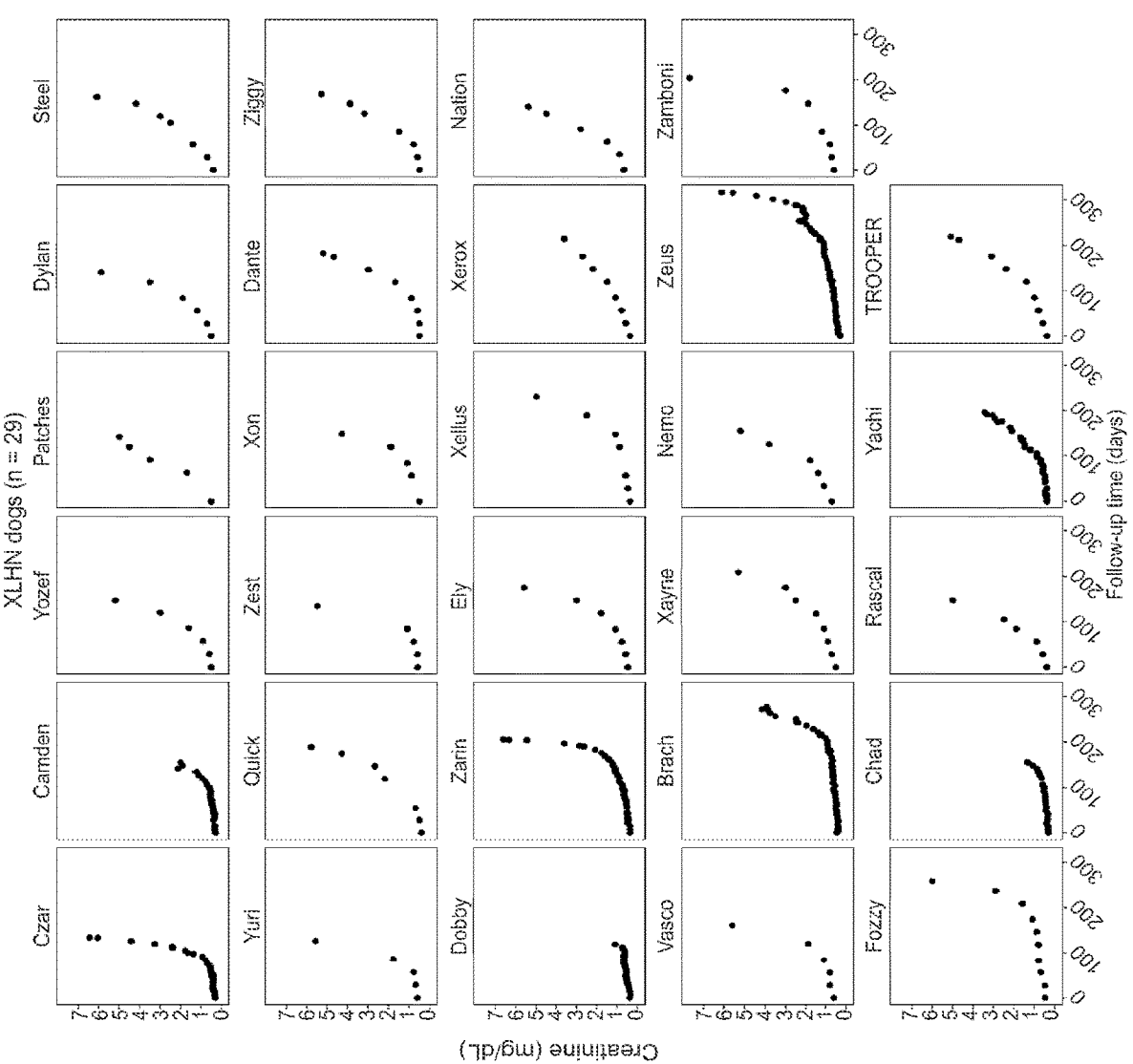
FIG. 21 shows serial observation in sCreatinine in XLHN cohort.
Figure 22:
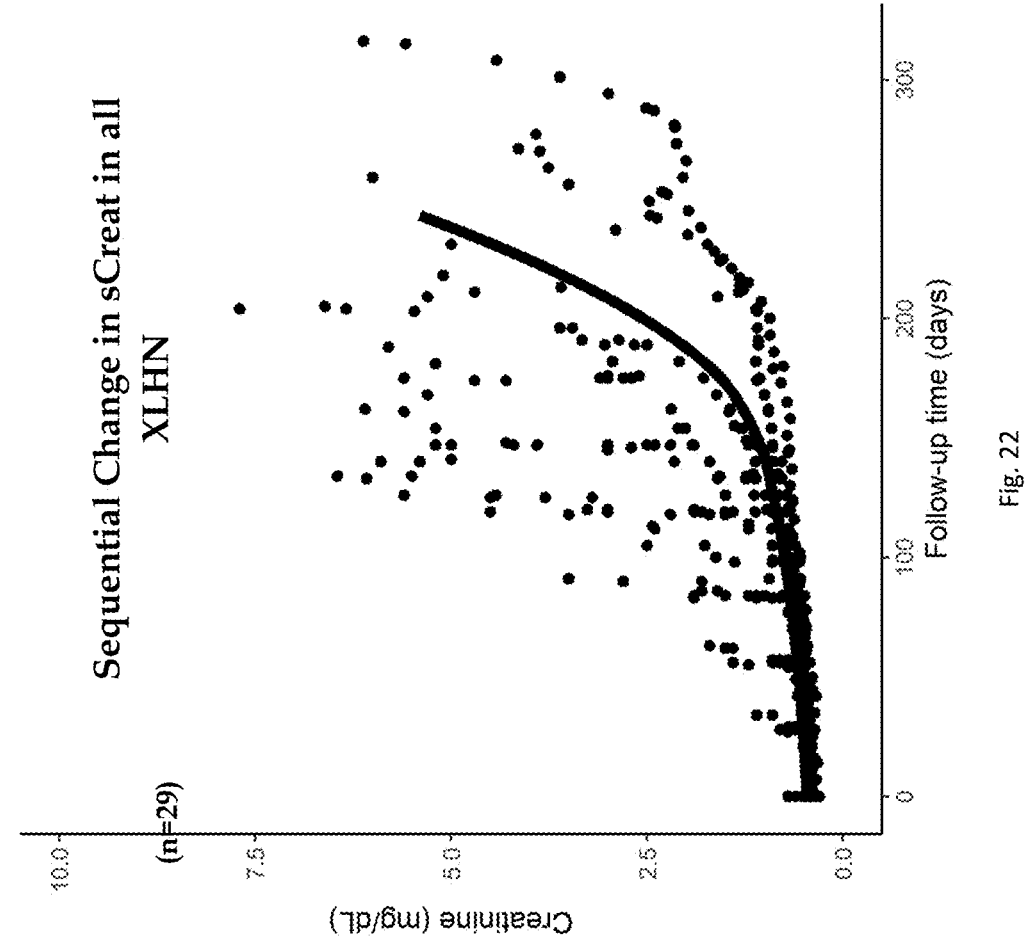
FIG. 22 shows sequential change in sCreatinine in XLHN cohort.
Figure 25:
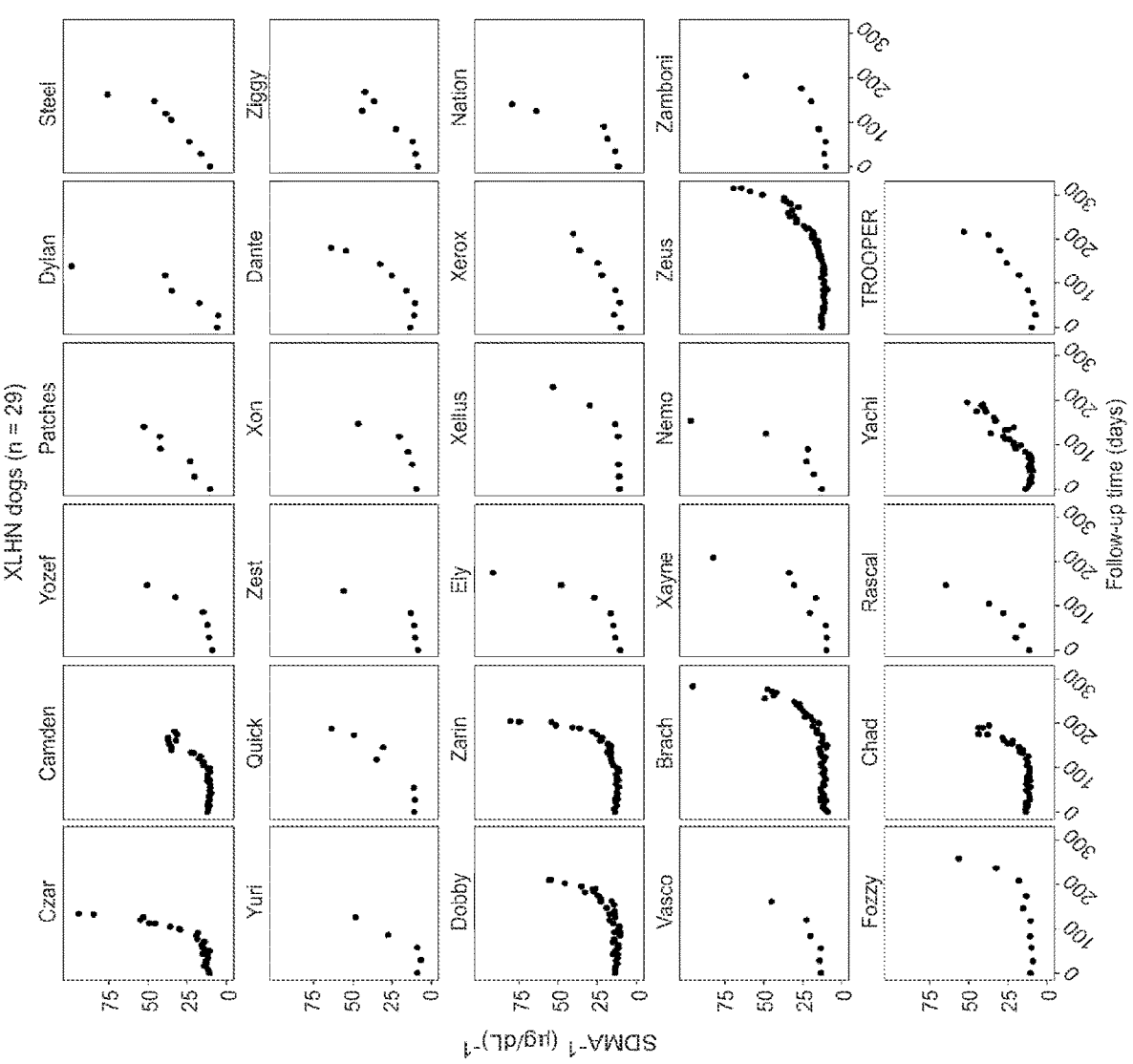
FIG. 25 shows serial observation in sSDMA in XLHN cohort.
Figure 26:
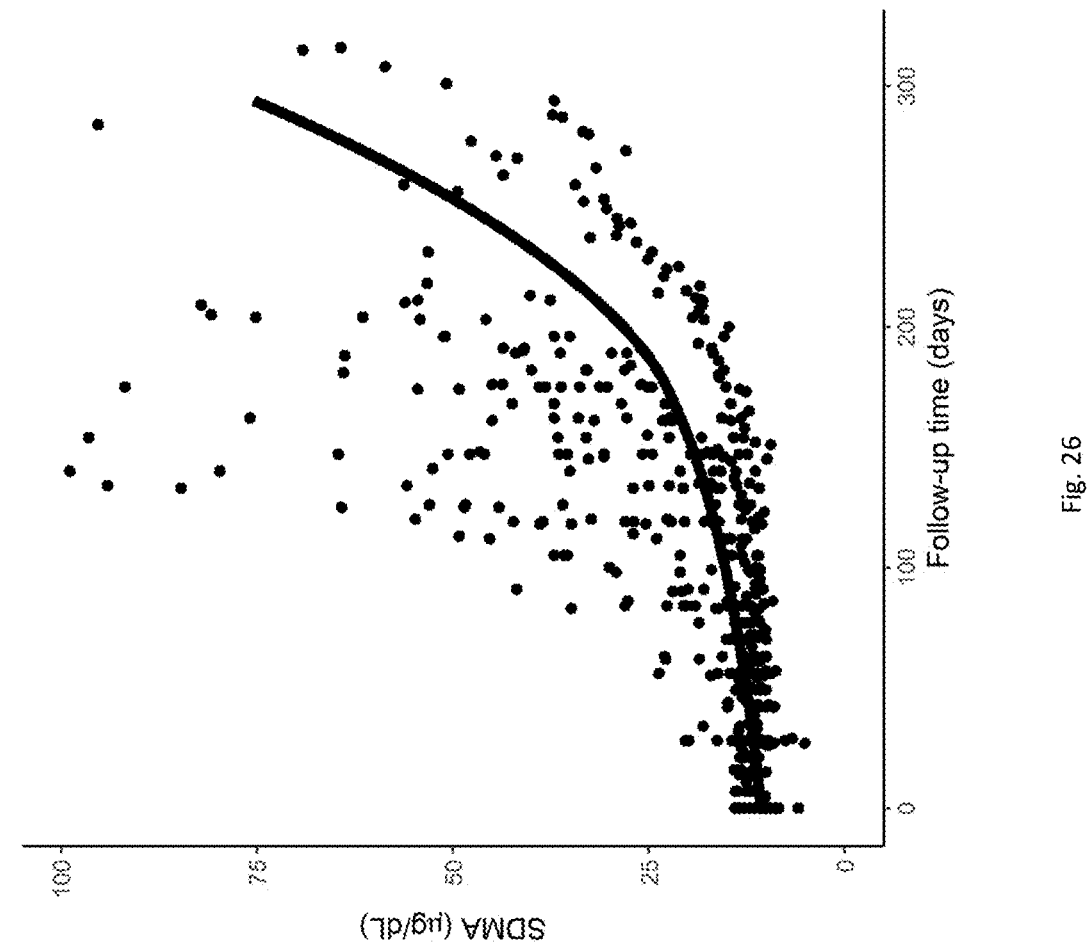
FIG. 26 shows sequential change in sSDMA in XLHN cohort.

In contrast to healthy dogs, functional marker sCreatinine demonstrated a progressive, exponential increase in XLHN cohort (FIG. 21, FIG. 22, and Table 9. Similarly, functional marker sSDMA demonstrated a progressive, exponential increase in XLHN cohort (FIG. 25, FIG. 26, and Table 10)

TABLE 9

| Median sCreatinine in the XLHN Cohort (n = 29). XLHN (n = 29) | |
| --- | --- |
| Start | 0.5 (IQR, 0.4-0.5) mg/dL |
| End | 5.4 (IQR, 5.1-5.9) mg/dL |
| Observation interval | 181 (IQR, 147-209) days |

TABLE 10

| Median sSDMA in XLHN Cohort (n = 29). XLHN (n = 29) | |
| --- | --- |
| Start | 10.6 (IQR, 9.8-12.9) µg/dL |
| End | 56.3 (IQR, 50.6-79.8) µg/dL |
| Observation interval | 181 (IQR, 147-209) days |

Figure 23:
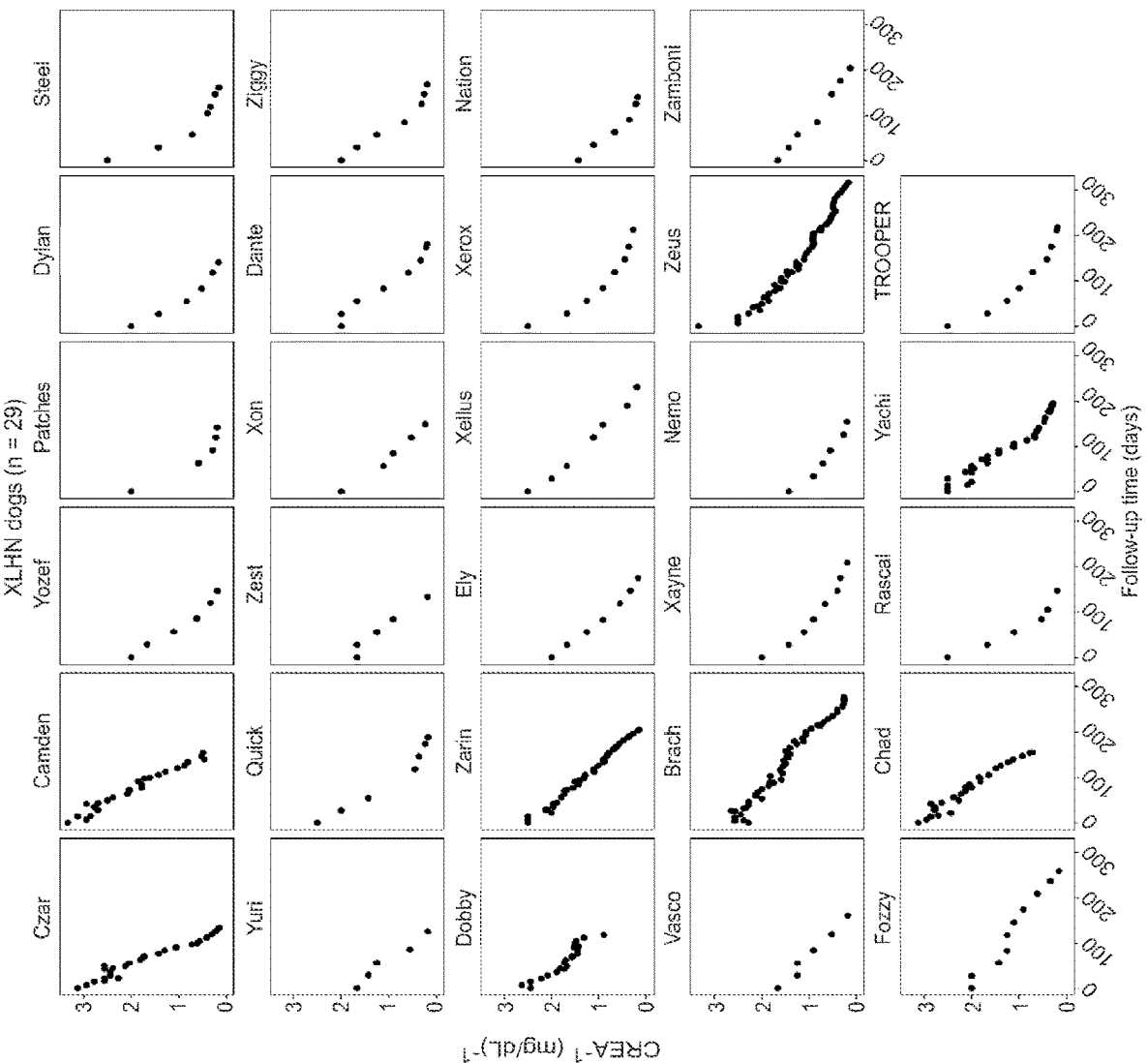
FIG. 23 shows serial changes in inverse creatinine in XLHN cohort.
Figure 24:
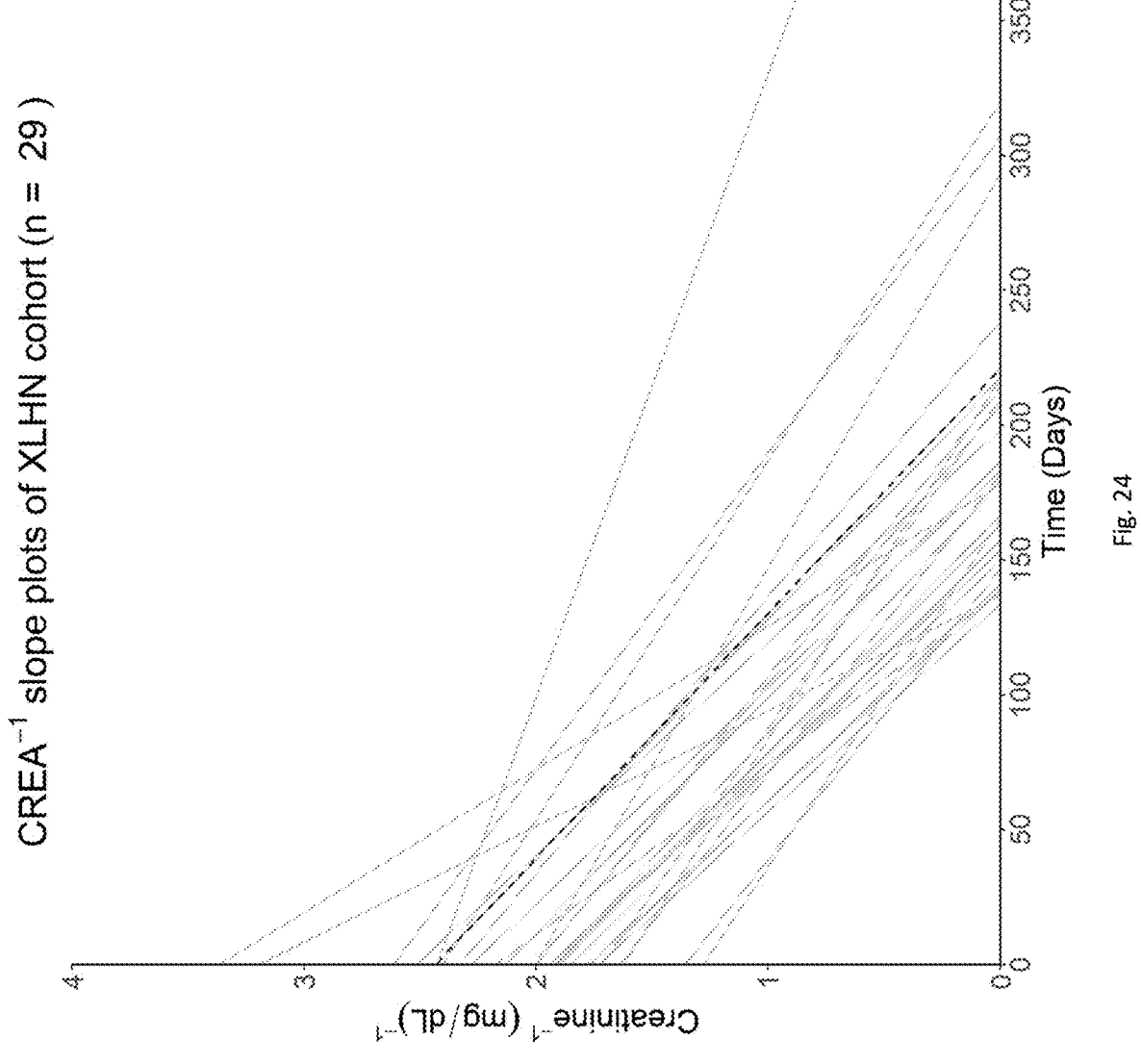
FIG. 24 shows inverse creatinine slope plots of XLHN cohort.
Figure 27:
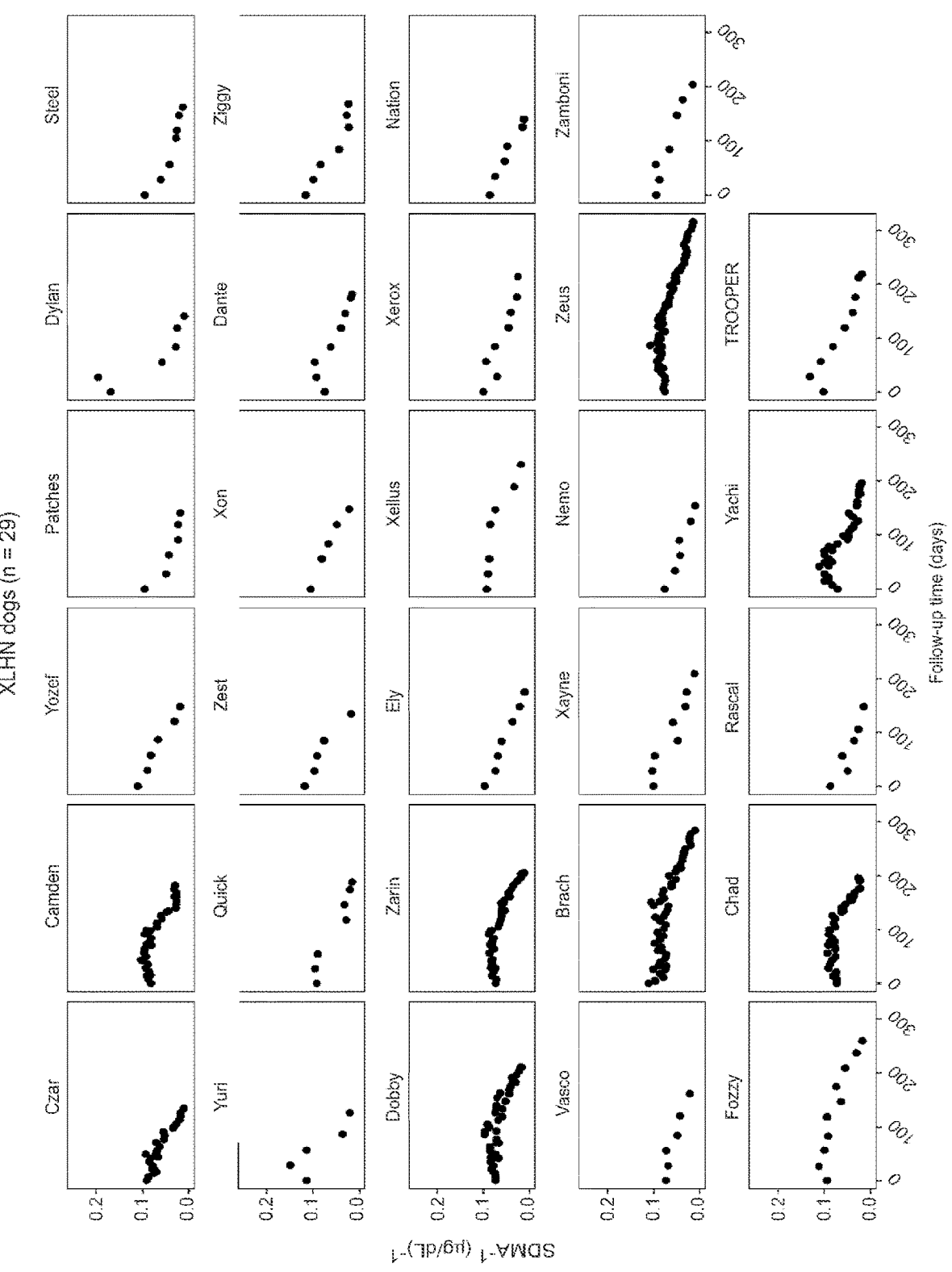
FIG. 27 shows serial changes in inverse SDMA in XLHN cohort.
Figure 28:
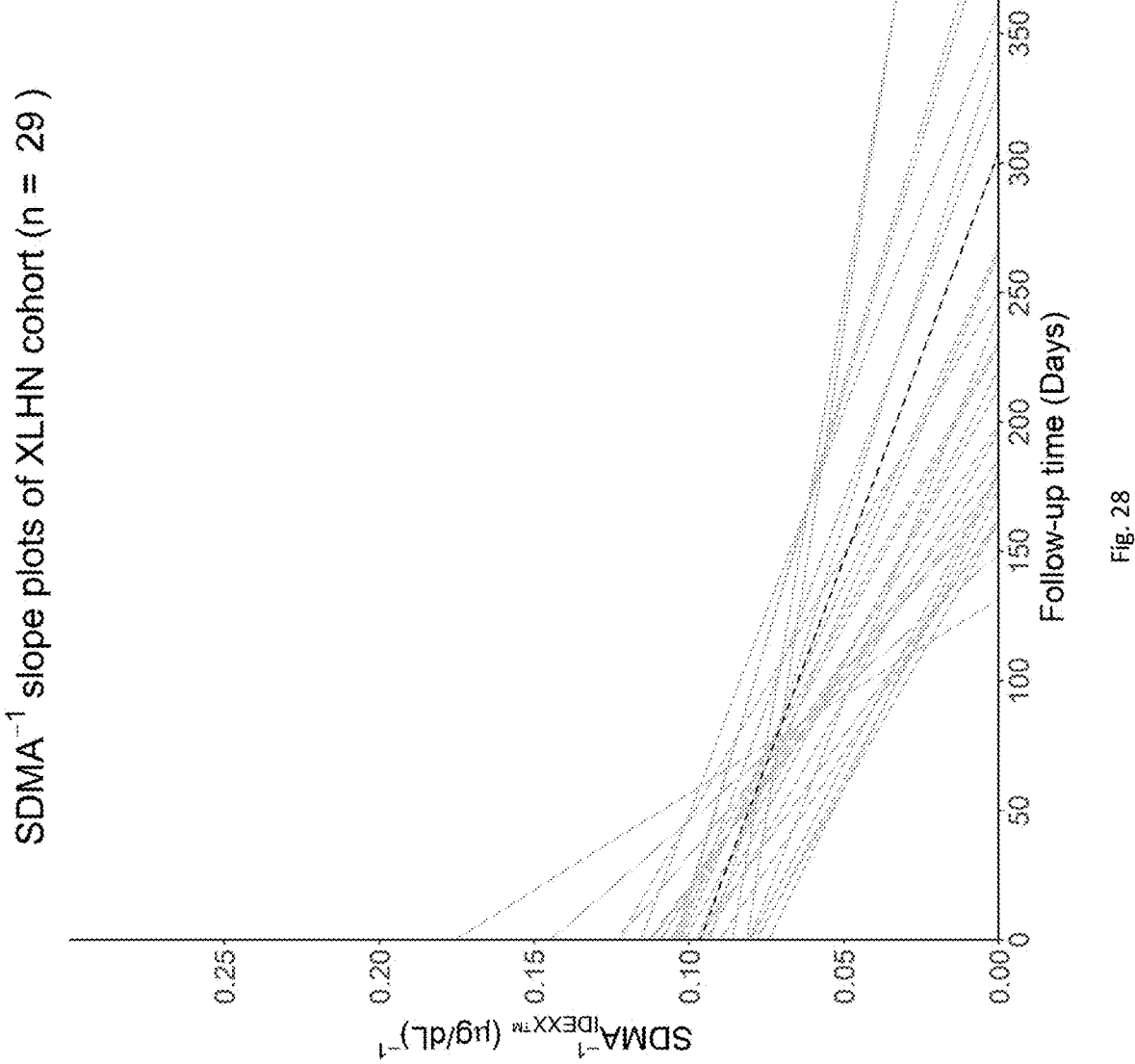
FIG. 28 shows inverse SDMA slope plots of XLHN cohort.

1/creatinine demonstrated a progressive linear decrease in all XLHN dogs over a median 181 days of observation. The median slope (day) was 1/creatinine=–0.01120215*[(mg/ dl)–1/day]*(# days)+2.435009. The median slope (week) was 1/creatinine=–0.07841505*[(mg/dl)–1/week]*(# weeks)+2.435009 (FIG. 23 and FIG. 24). Similarly, 1/SDMA demonstrated a progressive linear decrease in all XLHN dogs over a median 181 days of observation. The median slope (day) was 1/SDMA=–0.0004527534*[(µg/ dl)–1/day]*(# days)+0.07788298. The median slope (week) was 1/SDMA=–0.0031692738*[(µg/dl)–1/week]*(# weeks)+0.07788298 (FIG. 27 and FIG. 28).

Figure 29:
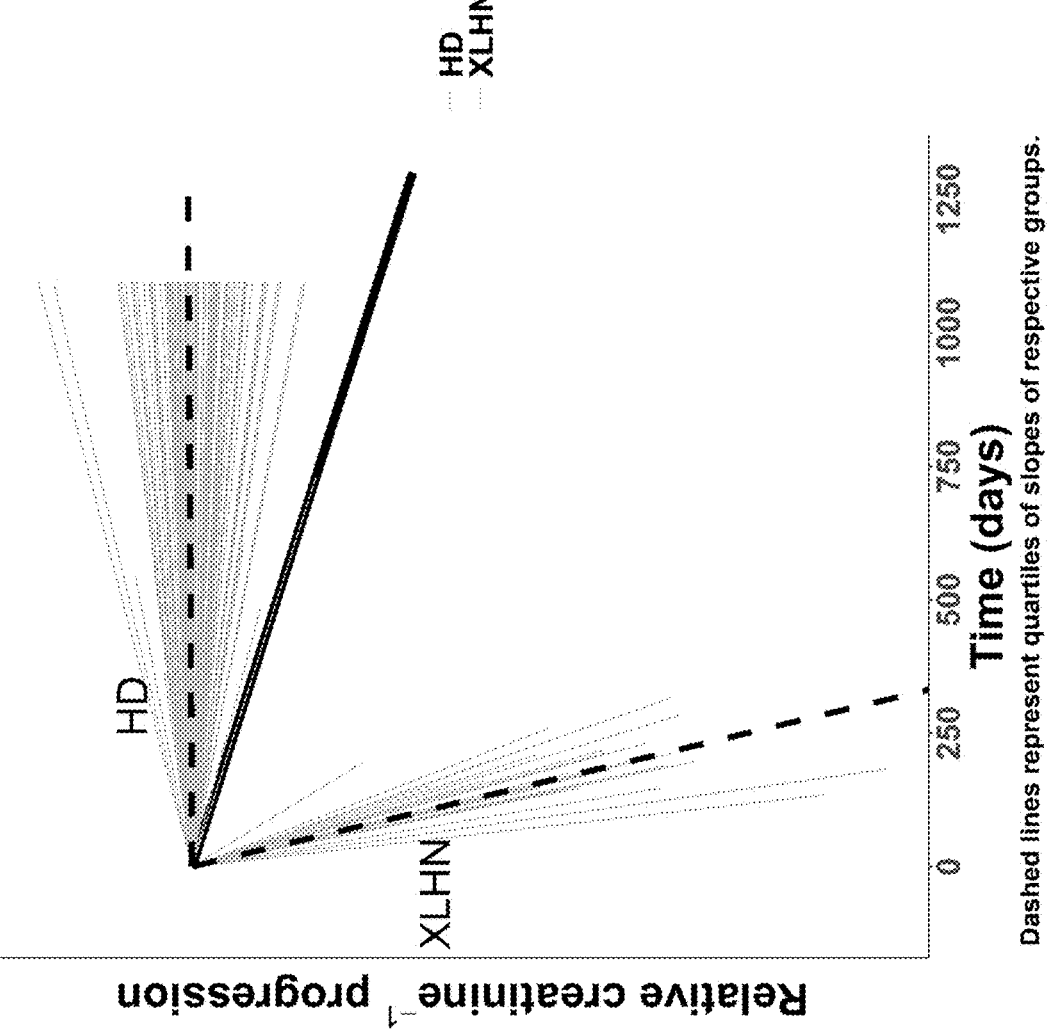
FIG. 29 shows inverse creatinine slope cutoff to distinguish stable kidney function in healthy dogs (HD) versus kidney dysfunction in progressive CKD resulting from X-linked hereditary nephropathy (XLHN).
Figure 30:
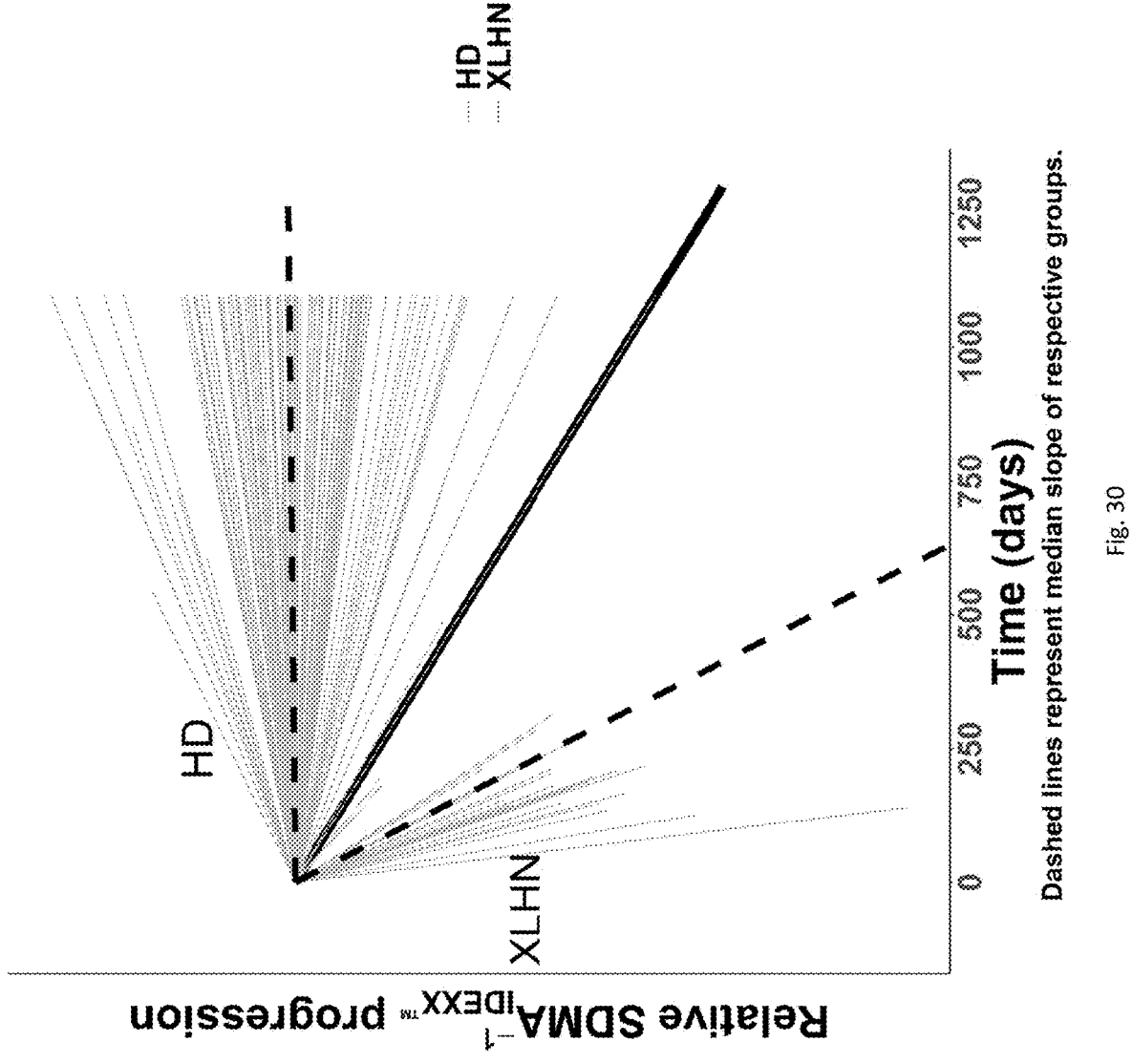
FIG. 30 shows inverse SDMA slope cutoff to distinguish stable kidney function in healthy dogs (HD) versus kidney dysfunction in progressive CKD resulting from X-linked hereditary nephropathy (XLHN).
Figure 31:
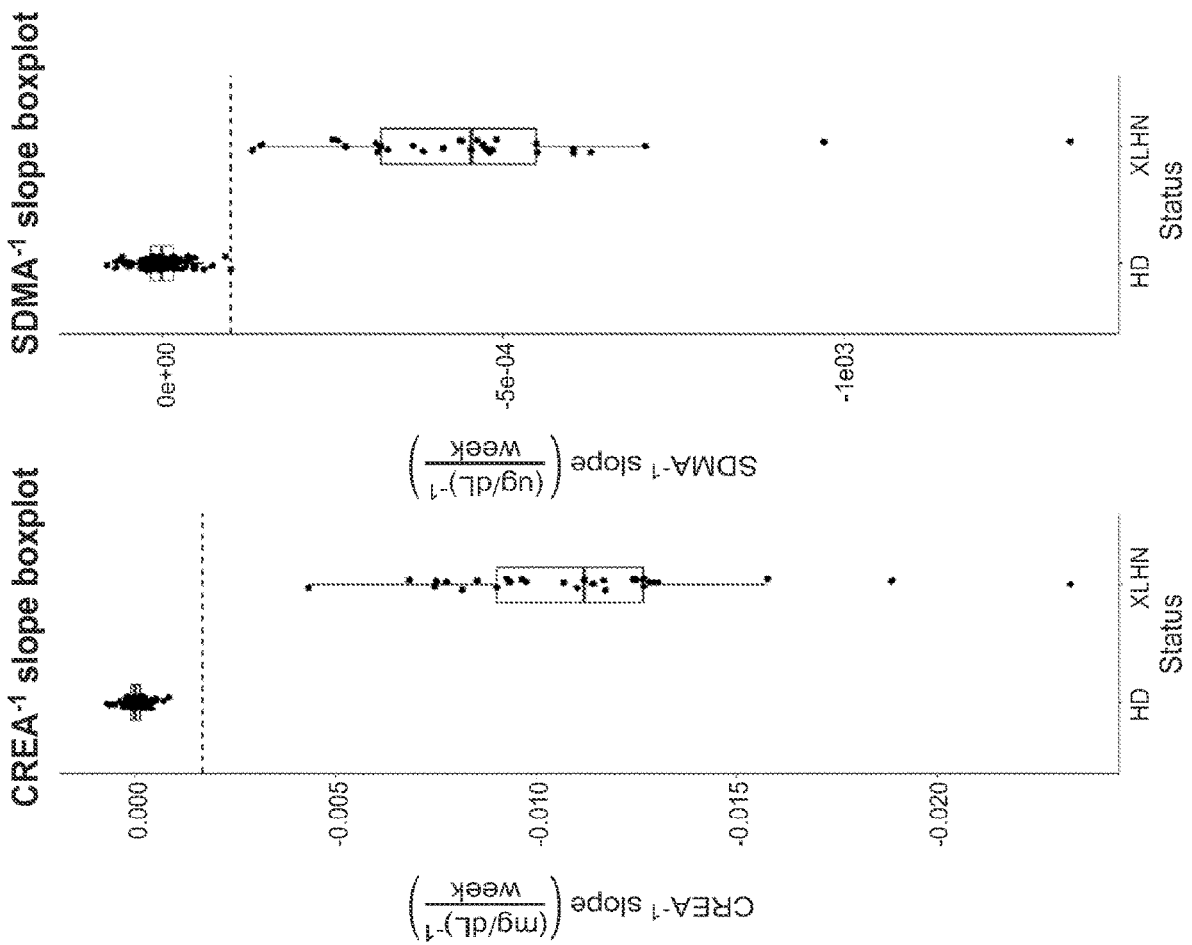
FIG. 31 shows box blots demonstrating slope cutoff (dotted line) to distinguish stable kidney function in healthy dogs (HD) versus kidney dysfunction in progressive CKD resulting from X-linked hereditary nephropathy (XLHN) in inverse creatinine (left panel) and in inverse SDMA (right panel).

The stable versus progressive slope cutoff was $-0.0117$ (mg/dL)$^{-1}$/week for 1/creatinine and $-0.0007$ (µg/dL)$^{-1}$/ week for SDMA® (FIG. 29, FIG. 30, and FIG. 31).

In the studied cohorts, stable kidney function in healthy dogs could be distinguished from progressive kidney dysfunction in XLHN by the slope of the 1/creatinine or 1/SDMA curves.

If extended to other populations of CKD, short-term (2-3 month) assessments of 1/creatinine or 1/SDMA slope may permit identification of dogs with stable vs progressive CKD.

Discrete values of 1/creatinine or 1/SDMA slope may serve as guidelines (cutoffs) to define kidney function as "stable" or "progressive" and direct appropriate therapies for each state.

What is claimed is:

1. A method for differentiating stable chronic kidney disease ("CKD") from progressive CKD in a subject diagnosed with CKD by:

(a) determining the amount of Cystatin B polypeptides, clusterin polypeptides, or both, in a sample from the subject at a single time point, (b) comparing the amount of the Cystatin B polypeptides, clusterin polypeptides, or both in the sample to a control sample or control standard, wherein increased levels of Cystatin B polypeptides or clusterin polypeptides, or both in the sample as compared to the control sample or control standard is an indication of progressive CKD; and where the subject is indicated as having progressive CKD, further comprising administering one or more treatments to the subject comprising: surgery for obstructed ureters, obstructive nephroliths or uroliths, dietary management, administration of enteric phosphate binders, antiproteinurics, administration of antihypertensives, fluid therapy to correct dehydration, management of acidosis, administration of diuretics, dialysis, correction of electrolyte abnormalities, administration of antiemetics, administration of antacids, administration of recombinant erythropoietin, holistic treatment, or combinations thereof to the subject.

2. The method of claim 1, wherein the subject is, prior to step (a), diagnosed with International Renal Interest Society CKD Stage I or CKD with a symmetric dimethylarginine (SDMA) value of up to 20 µg/dl.

3. The method of claim 1, further comprising determining the amount of Cystatin B polypeptides, clusterin polypeptides, or both, in a sample from the subject at 2, 3, 4, 5, or more additional time points.

4. The method of claim 1, wherein the amount of the Cystatin B polypeptides is determined using one or more antibodies or specific binding fragments that specifically bind a Cystatin B polypeptide.

5. The method of claim 1, wherein the amount of the clusterin polypeptides is determined using one or more antibodies or specific binding fragments that specifically bind a clusterin polypeptide.

6. The method of claim 1, wherein determining the amount of Cystatin B polypeptides or clusterin polypeptides in a sample from the subject comprises contacting the sample with one or more antibodies or specific binding fragments thereof that specifically bind a Cystatin B polypeptide or a clusterin polypeptide under conditions suitable for formation of complexes of the Cystatin B polypeptides or clusterin polypeptides and the one or more antibodies or specific binding fragments thereof, and detecting the complexes of Cystatin B polypeptides or clusterin polypeptides and the one or more antibodies or specific binding fragments thereof.

7. The method of claim 6, wherein the antibodies or specific binding fragments thereof are immobilized to a solid support.

8. The method of claim 6, wherein the antibodies or specific binding fragments thereof are conjugated to one or more labels.

9. The method of claim 6, further comprising contacting the complexes of the Cystatin B polypeptides or the clusterin polypeptides and the one or more antibodies or specific binding fragments thereof with an indicator agent.

10. The method of claim 1, wherein the subject is a non-human mammal.

11. The method of claim 10, wherein the non-human mammal is a canine or a feline.

12. The method of claim 1, wherein the sample is blood, serum, plasma, or urine.

13. The method of claim 1, wherein the amount of Cystatin B or clusterin polypeptides is determined by an immunoassay, a competitive immunoassay, a sandwich immunoassay, an enzyme-linked immunosorbent assay (ELISA), a turbidimetric immunoassay, a particle-enhanced turbidimetric immunoassay, a radioimmunoassay (RIA), or a western blot assay.

14. The method of claim 1, wherein determining the amount of Cystatin B or clusterin polypeptides comprises subjecting the sample to mass spectrometry, LC-MS, quantitative nuclear magnetic resonance (qNMR), amino acid analysis (AAA), chromatographic (HPLC) mass balance assay, or combinations thereof.

15. The method of claim 1, wherein the control sample or control standard is derived from normal, healthy subjects.

16. The method of claim 1, wherein the control sample is derived from subjects having stable CKD.

* * * * *